United States Patent
Watanabe et al.

(10) Patent No.: US 10,393,678 B2
(45) Date of Patent: Aug. 27, 2019

(54) X-RAY DEVICE AND MANUFACTURING METHOD OF STRUCTURE

(71) Applicants: NIKON CORPORATION, Tokyo (JP); NIKON METROLOGY NV, Leuven (BE)

(72) Inventors: Takashi Watanabe, Naka-gun (JP); Daniel Hilton, Aylesbury (GB); Sam Hawker, Berkhamstead (GB)

(73) Assignee: NIKON CORPORATION, Tokyo (JP)

( * ) Notice: Subject to any disclaimer, the term of this patent is extended or adjusted under 35 U.S.C. 154(b) by 784 days.

(21) Appl. No.: 14/935,837

(22) Filed: Nov. 9, 2015

(65) Prior Publication Data

US 2016/0139064 A1    May 19, 2016

Related U.S. Application Data

(63) Continuation of application No. PCT/JP2013/063221, filed on May 10, 2013.

(51) Int. Cl.
    *G01N 23/04*      (2018.01)
    *G01N 23/046*      (2018.01)
    (Continued)

(52) U.S. Cl.
    CPC ............ *G01N 23/046* (2013.01); *G01N 23/04* (2013.01); *G01N 23/06* (2013.01); *G01N 23/083* (2013.01);
    (Continued)

(58) Field of Classification Search
    CPC ...... G01N 23/04; G01N 23/046; G01N 23/06; G01N 23/083; G01N 23/087; G01V 5/0016; G01V 5/005; G01V 5/006; G01V 5/0066
    (Continued)

(56) References Cited

U.S. PATENT DOCUMENTS

| | | | | | |
|---|---|---|---|---|---|
| 4,422,177 A | * | 12/1983 | Mastronardi | ........ | A61B 6/0457 378/10 |
| 4,969,165 A | * | 11/1990 | Bernardi | .............. | G01N 23/046 378/13 |

(Continued)

FOREIGN PATENT DOCUMENTS

| | | |
|---|---|---|
| JP | 11-248459 | 9/1999 |
| JP | 2000-111500 A | 4/2000 |

(Continued)

OTHER PUBLICATIONS

International Search Report issued by the Japanese Patent Office in corresponding International Application No. PCT/JP2013/063221, dated Jul. 16, 2013 (6 pages).

(Continued)

*Primary Examiner* — Allen C. Ho
(74) *Attorney, Agent, or Firm* — Finnegan, Henderson, Farabow, Garrett & Dunner LLP

(57) ABSTRACT

Provided is a device capable of suppressing a drop in detection accuracy, and a manufacturing method of a structure. A detection device is a device that irradiates a subject with X-rays and detects the X-rays transmitting through the subject, and includes an X-ray source that emits X-rays, a table that holds the subject, a detector that detects at least a portion of the transmitted X-rays emitted from the X-ray source and transmitted through the subject, and a first guide device and a second guide device that guide movement of the table in a direction parallel to an optical axis of the X-ray source while supporting the table. In this detection device, a guide plane, which is parallel to the optical axis and is a plane to which the movement of the table is regulated, passes through the inside of a detection region of the transmitted X-rays of the detector.

8 Claims, 32 Drawing Sheets

(51) Int. Cl.
*G01N 23/06* (2018.01)
*G01N 23/083* (2018.01)
*G01N 23/087* (2018.01)
*G01V 5/00* (2006.01)

(52) U.S. Cl.
CPC ............ *G01N 23/087* (2013.01); *G01V 5/005* (2013.01); *G01V 5/0016* (2013.01); *G01V 5/0066* (2013.01); *G01N 2223/33* (2013.01); *G01N 2223/646* (2013.01)

(58) Field of Classification Search
USPC ........ 378/10, 51, 57, 58, 62, 20, 53–55, 205
See application file for complete search history.

(56) References Cited

U.S. PATENT DOCUMENTS

| | | | | |
|---|---|---|---|---|
| 4,989,225 | A * | 1/1991 | Gupta | G01N 23/046 378/10 |
| 5,012,498 | A * | 4/1991 | Cuzin | A61B 6/032 250/370.15 |
| 5,023,895 | A * | 6/1991 | McCroskey | G01N 23/046 378/10 |
| 5,119,408 | A * | 6/1992 | Little | G01N 23/046 378/10 |
| 5,615,244 | A * | 3/1997 | Dykster | G01N 23/04 378/177 |
| 5,648,996 | A * | 7/1997 | Gupta | G01N 23/04 378/11 |
| 5,740,221 | A * | 4/1998 | Norman | G01N 23/04 378/57 |
| 5,754,617 | A * | 5/1998 | Itoh | G01N 23/046 378/4 |
| 5,754,621 | A * | 5/1998 | Suzuki | G01N 23/04 378/51 |
| 5,933,473 | A * | 8/1999 | Kitaguchi | G01N 23/043 378/149 |
| 6,047,041 | A * | 4/2000 | Ellinger | G01N 23/04 378/57 |
| 6,104,776 | A * | 8/2000 | Oikawa | G01N 23/20025 378/10 |
| 6,485,176 | B1 * | 11/2002 | Chen | G01N 23/04 378/193 |
| 6,553,094 | B1 * | 4/2003 | Bernardi | G01N 23/046 378/21 |
| 6,643,351 | B2 * | 11/2003 | Morita | A61B 6/032 378/4 |
| 6,711,235 | B2 * | 3/2004 | Galish | G01N 23/04 378/147 |
| 7,016,465 | B2 * | 3/2006 | Kamegawa | G01N 23/046 378/19 |
| 7,110,489 | B2 * | 9/2006 | Roy | G01N 23/046 378/20 |
| 7,130,375 | B1 * | 10/2006 | Yun | G01N 23/04 378/79 |
| 7,139,363 | B2 * | 11/2006 | Misawa | A61B 6/4441 378/11 |
| 7,177,388 | B2 * | 2/2007 | Takagi | G01N 23/046 378/20 |
| 7,254,211 | B2 * | 8/2007 | Hunt | G01N 23/046 378/20 |
| 7,286,630 | B2 * | 10/2007 | Holt | A61B 6/032 378/20 |
| 7,341,376 | B2 * | 3/2008 | Birdwell | G01N 23/04 378/203 |
| 7,356,115 | B2 * | 4/2008 | Ford | G01N 23/046 378/4 |
| 7,386,090 | B2 * | 6/2008 | Schroeder | A61B 6/032 378/20 |
| 7,397,894 | B2 * | 7/2008 | Nakai | G01N 23/04 378/55 |
| 7,492,862 | B2 * | 2/2009 | Bendahan | G01V 5/0041 378/195 |
| 7,508,908 | B2 * | 3/2009 | Hu | G01N 9/24 378/54 |
| 7,539,283 | B2 * | 5/2009 | Bendahan | G01T 1/1603 378/44 |
| 7,551,714 | B2 * | 6/2009 | Rothschild | G01N 23/046 378/44 |
| 7,634,055 | B2 * | 12/2009 | Hu | G01N 23/10 378/53 |
| 7,647,189 | B2 * | 1/2010 | Kang | G01N 23/046 378/53 |
| 7,672,426 | B2 * | 3/2010 | Seppi | G01N 23/046 378/20 |
| 7,714,304 | B2 * | 5/2010 | Poglitsch | G01N 23/046 250/370.09 |
| 7,760,852 | B2 * | 7/2010 | Chen | A61B 6/587 378/19 |
| 7,775,715 | B2 * | 8/2010 | Warner | G01N 23/046 378/20 |
| 7,792,242 | B2 * | 9/2010 | Kamegawa | G01N 23/046 378/20 |
| 7,813,470 | B2 * | 10/2010 | Kuwabara | G01N 23/087 378/4 |
| 7,844,027 | B2 * | 11/2010 | Harding | G01V 5/00 378/20 |
| 7,876,875 | B2 * | 1/2011 | Warner | G01N 23/046 378/10 |
| 7,881,424 | B2 * | 2/2011 | Zhang | G01T 7/005 378/5 |
| 7,912,174 | B2 * | 3/2011 | Liu | G01N 23/046 378/10 |
| 7,945,017 | B2 * | 5/2011 | Chen | G01N 23/046 378/57 |
| 7,972,062 | B2 * | 7/2011 | Nicolosi | G21K 7/00 378/205 |
| 8,068,579 | B1 * | 11/2011 | Yun | G01N 23/046 378/21 |
| 8,121,247 | B2 * | 2/2012 | Kunzmann | G01N 23/046 378/19 |
| 8,160,342 | B2 * | 4/2012 | Khare | H04N 19/635 382/131 |
| 8,229,061 | B2 * | 7/2012 | Hanke | G01N 23/046 378/20 |
| 8,422,624 | B2 * | 4/2013 | Christoph | G01B 15/00 378/4 |
| 8,422,626 | B2 * | 4/2013 | Jin | G01N 23/046 378/10 |
| 8,437,447 | B2 * | 5/2013 | Muenker | G01N 23/046 378/21 |
| 8,467,496 | B2 * | 6/2013 | Ullberg | G01N 33/46 378/53 |
| 8,542,793 | B1 * | 9/2013 | Jin | G01N 23/046 378/4 |
| 8,600,002 | B2 * | 12/2013 | Hur | A61B 50/37 378/21 |
| 8,670,522 | B2 * | 3/2014 | Lee | G03B 35/04 378/41 |
| 8,705,693 | B2 * | 4/2014 | Hadland | G01N 23/046 378/21 |
| 8,804,905 | B2 * | 8/2014 | Christoph | A61B 6/583 378/19 |
| 8,861,673 | B2 * | 10/2014 | Michaels | G01B 15/045 378/4 |
| 8,983,030 | B2 * | 3/2015 | Ookawa | H05K 13/08 378/62 |
| 8,989,345 | B2 * | 3/2015 | Kim | G01N 9/24 378/207 |
| 9,025,724 | B2 * | 5/2015 | Lee | G01N 9/24 378/10 |
| 9,025,855 | B1 * | 5/2015 | Christoph | G01N 23/046 382/152 |
| 9,042,510 | B2 * | 5/2015 | Voland | G01N 23/046 378/4 |
| 9,146,327 | B2 * | 9/2015 | Suppes | G01T 7/005 |
| 9,170,216 | B2 * | 10/2015 | Ahn | G01N 23/046 |
| 9,234,855 | B2 * | 1/2016 | Watanabe | G01N 23/04 |
| 9,322,790 | B2 * | 4/2016 | Ookawa | G01N 23/043 |

(56) References Cited

U.S. PATENT DOCUMENTS

| | | | |
|---|---|---|---|
| 9,329,139 B2* | 5/2016 | Itou | G01N 23/043 |
| 9,341,546 B2* | 5/2016 | Stuke | G01M 17/013 |
| 9,347,894 B2* | 5/2016 | Sims | A61B 5/0035 |
| 9,459,217 B2* | 10/2016 | Wang | G01N 23/046 |
| 9,953,799 B2* | 4/2018 | Hakoda | B22D 46/00 |
| 10,190,997 B2* | 1/2019 | Aoki | G01N 23/083 |
| 2002/0154728 A1 | 10/2002 | Morita et al. | |
| 2004/0017882 A1 | 1/2004 | Misawa et al. | |
| 2009/0268869 A1 | 10/2009 | Hadland | |
| 2010/0220908 A1 | 9/2010 | Khare et al. | |
| 2011/0222650 A1 | 9/2011 | Muenker | |
| 2013/0083896 A1 | 4/2013 | Watanabe | |
| 2014/0283385 A1 | 9/2014 | Watanabe | |

FOREIGN PATENT DOCUMENTS

| | | |
|---|---|---|
| JP | 2003-240734 A | 8/2003 |
| JP | 2004-85221 | 3/2004 |
| JP | 2009-14710 | 1/2009 |
| JP | 2009-47551 | 3/2009 |
| JP | 2010-139454 | 6/2010 |
| JP | 2010-210389 | 9/2010 |
| WO | WO 2007/043974 A1 | 4/2007 |
| WO | WO 2012/057284 A1 | 5/2012 |
| WO | WO 2013/051594 A1 | 4/2013 |

OTHER PUBLICATIONS

Written Opinion of the International Searching Authority issued by the Japanese Patent Office in corresponding International Application No. PCT/JP2013/063221, dated Jul. 16, 2013 (11 pages).

Office Action issued by Japanese Patent Office in counterpart Japanese Patent Application No. JP2015-515765 dated Jun. 28, 2016, and English Translation thereof.

Office Action issued by the State Intellectual Property Office of the People's Republic of China dated Jul. 19, 2017 in a counterpart Application No. 201380076108.2, and English translation thereof.

Supplemental Extended European Search Report issued by the European Patent Office in counterpart European Application No. 13884256.2, dated Mar. 6, 2017 (17 pages).

Partial European Search Report issued by the European Patent Office in European Application No. 13884256.2, dated Dec. 13, 2016 (7 pages).

* cited by examiner

X-RAY DEVICE AND MANUFACTURING METHOD OF STRUCTURE

CROSS REFERENCE TO RELATED APPLICATIONS

This is the national stage of International Application No. PCT/JP2013/063221 filed on May 10, 2013. The contents of the aforementioned applications are incorporated herein by reference in its entirety.

BACKGROUND

The present invention relates to an X-ray device and a manufacturing method of a structure.

An X-ray device such as that disclosed in the Patent Document mentioned below, which irradiates an object with X-rays and detects transmitted X-rays that have been transmitted through the object, is known as a device that obtains information of the interior of the object in a non-invasive manner.

SUMMARY OF EMBODIMENTS

Technical Problem

In a detection device, it is necessary to improve the accuracy at which a measurement device, which measures the position in a movement direction of a table that moves while supporting the object, determines the position in the movement direction. If, in such a detection device, the position of a device that guides the table that moves while supporting the object is distanced from a detection position of a detector that detects the transmitted X-rays transmitted through the object, the positioning precision of the measurement position of the table may drop. The detection accuracy may drop as a result.

An aspect of the present teaching provides an X-ray device capable of suppressing a drop in detection accuracy, and a manufacturing method for a structure.

A first aspect of the present teaching provides an X-ray device configured to irradiate a measurement object with X-rays and detect X-rays transmitted through the measurement object, the X-ray device including: an X-ray source configured to emit X-rays from a light-emission point; a stage configured to support the measurement object; a detector configured to detect at least a portion of transmitted X-rays that have been emitted from the X-ray source and transmitted through the measurement object; a movement device configured to move one of the X-ray source, the stage, or the detector in a first direction as a mobile object in order to change at least one of a distance between the light-emission point and the measurement object or a distance between the light-emission point and the detector; and a first measurement device and a second measurement device each configured to measure a position of the mobile object in the first direction. Here, the first measurement device and the second measurement device are disposed along a second direction orthogonal to the first direction in a mobile region of the movement device.

A second aspect of the present teaching provides an X-ray device configured to irradiate a measurement object with X-rays and detect X-rays transmitted through the object, the device including: an X-ray source configured to emit X-rays from a light-emission point; a stage configured to support the measurement object; a detector configured to detect at least a portion of transmitted X-rays that have been emitted from the X-ray source and transmitted through the measurement object; and a guide device configured to define a guide plane serving as a plane of movement of at least one of the X-ray source, the stage, and the detector and guides the movement in order to change at least one of a distance between the light-emission point and the measurement object or a distance between the light-emission point and the detector. Here, a plane that includes the guide plane and is parallel to the guide plane is located within a region where the transmitted X-rays transmitted through the measurement object are detected by the detector.

A third aspect of the present teaching provides an X-ray device configured to irradiate a measurement object with X-rays and detects X-rays transmitted through the measurement object, the device including: an X-ray source configured to emits X-rays from a light-emission point; a stage configured to support the measurement object; a detector configured to detect at least a portion of transmitted X-rays that have been emitted from the X-ray source and transmitted through the measurement object; and a guide device configured to guides movement of at least one of the X-ray source, the stage, and the detector in a direction parallel to an axis that connects the light-emission point to the center of a light-receiving surface at which the detector receives the X-rays. Here, a plane that includes a guide plane that is a plane regulating the movement of the X-ray source, the stage, and the detector and that is parallel to the guide plane is located in the vicinity of the axis that connects the light-emission point to the center of the light-receiving surface at which the detector receives the X-rays.

A fourth aspect of the present teaching provides a manufacturing method of a structure, the method including: creating design information regarding a shape of a structure; manufacturing the structure on the basis of the design information; using the aforementioned X-ray device to measure the shape of the manufactured structure, the manufactured structure serving as the measurement object; and comparing shape information obtained from the measurement with the design information.

Exemplary Effects of Embodiments

According to an aspect of the present teaching, an X-ray device capable of suppressing a drop in detection accuracy, and a manufacturing method for a structure, can be provided.

DESCRIPTION OF EMBODIMENTS

Embodiments for carrying out the present teaching (embodiments) will be described in detail with reference to the drawings. The present teaching is not intended to be limited to the embodiments described hereinafter.

In the following descriptions, an XYZ orthogonal coordinate system is set, and positional relationships between elements will be described with reference to this XYZ orthogonal coordinate system. A predetermined direction in a horizontal plane is defined as a Z-axis direction, a direction orthogonal to the Z-axis direction in the horizontal plane is defined as an X-axis direction, and a direction orthogonal to both the Z-axis direction and the X-axis direction (in other words, a vertical direction) is defined as a Y-axis direction. Furthermore, rotation (tilt) directions relative to the X-axis, the Y-axis, and the Z-axis are defined as θX, θY, and θZ directions, respectively.

Figure 1:
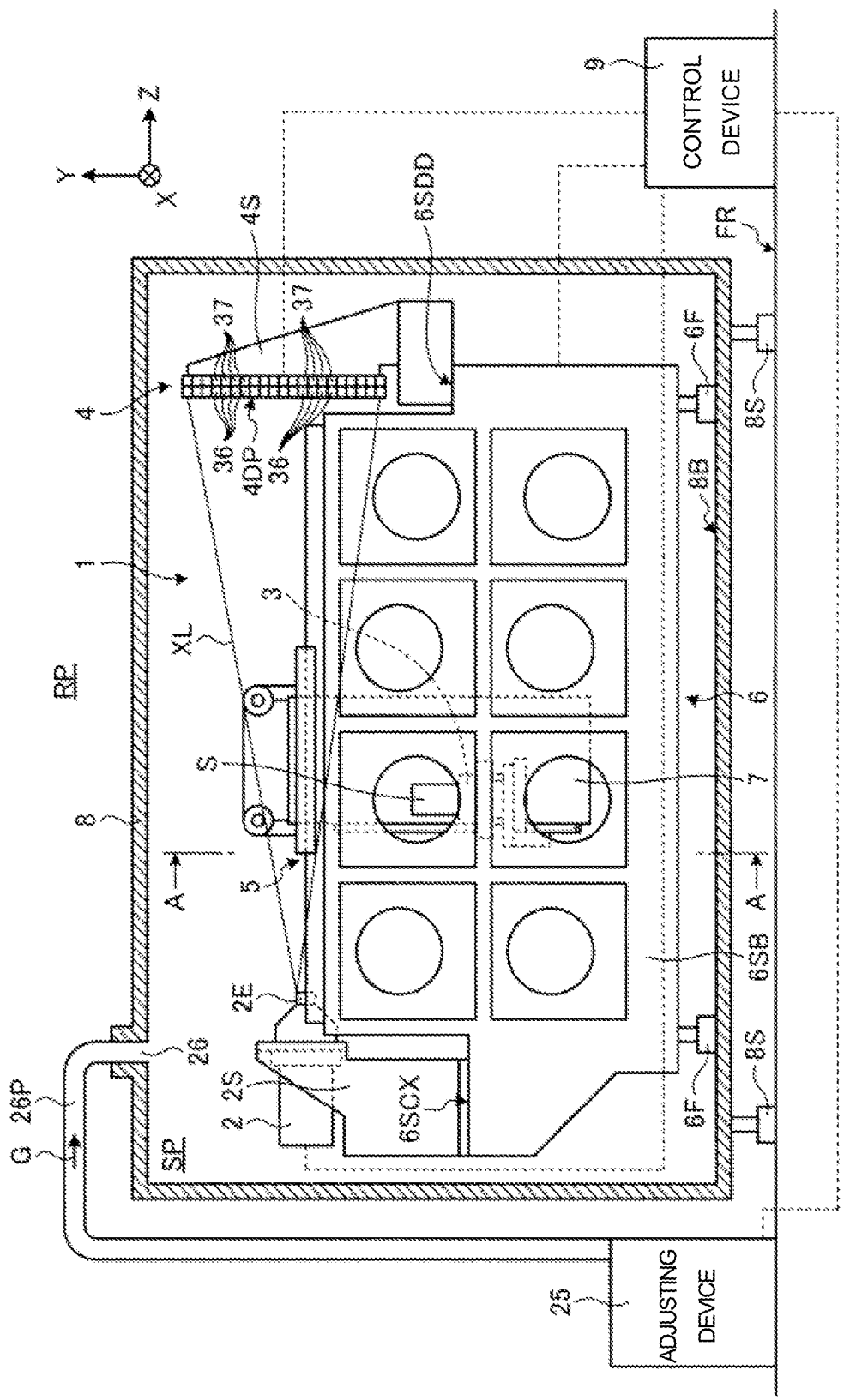
FIG. 1 is a diagram illustrating an example of a device according to an embodiment.
Figure 2:
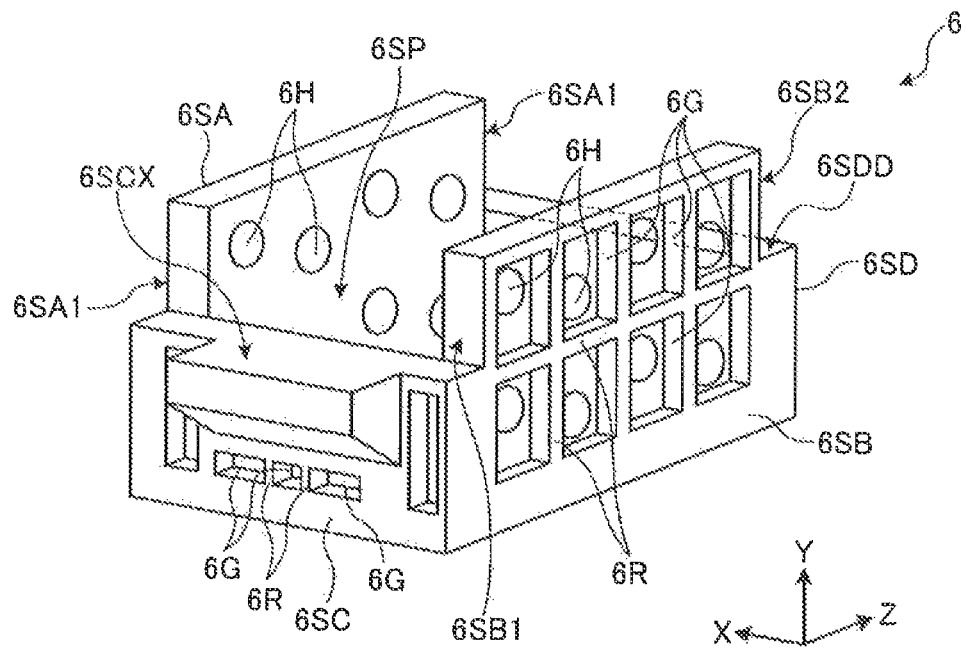
FIG. 2 is a perspective view illustrating an example of a support body in a device according to an embodiment.
Figure 3:
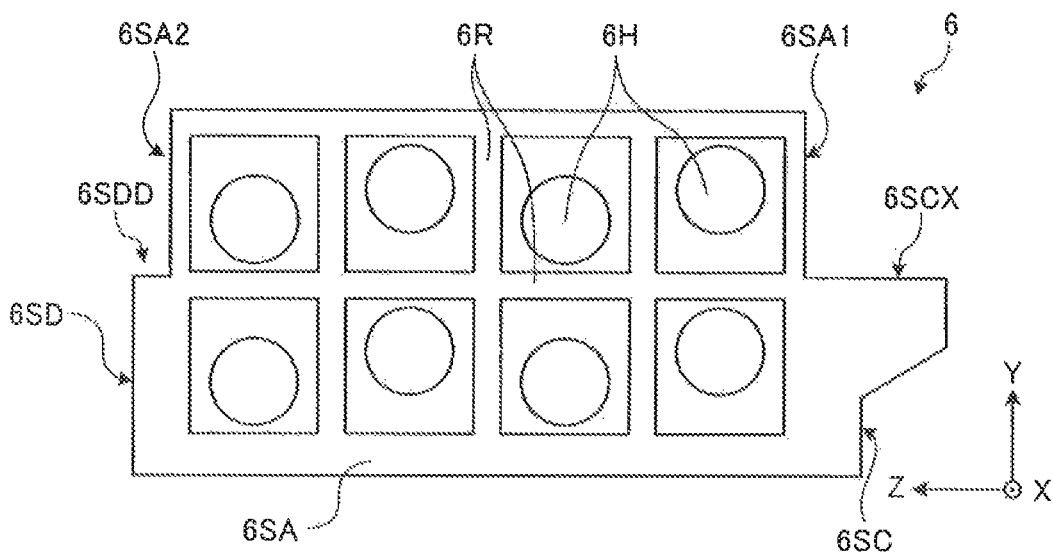
FIG. 3 is a side view illustrating a first side wall of the support body illustrated in FIG. 2.
Figure 4:
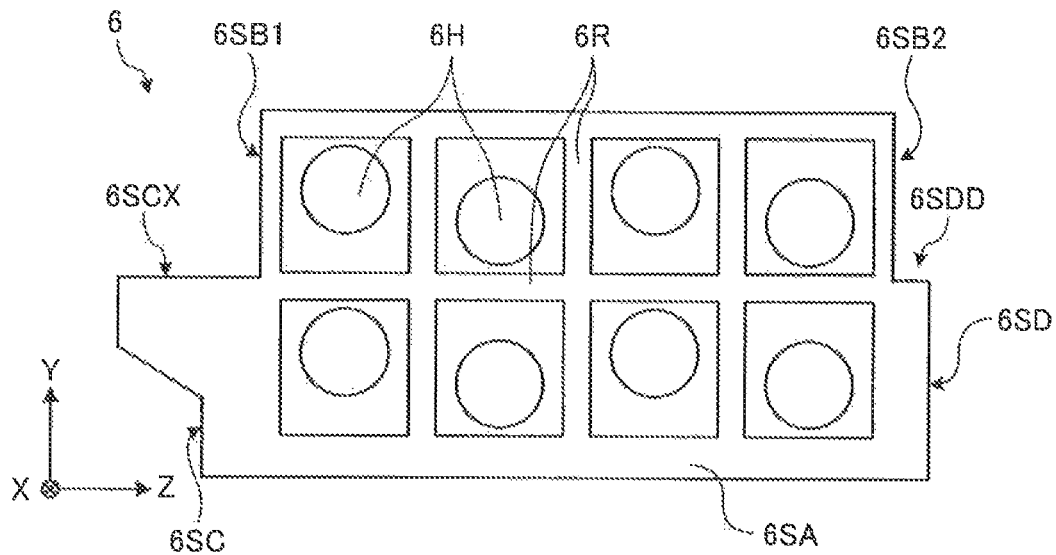
FIG. 4 is a side view illustrating a second side wall of the support body illustrated in FIG. 2.
Figure 5:
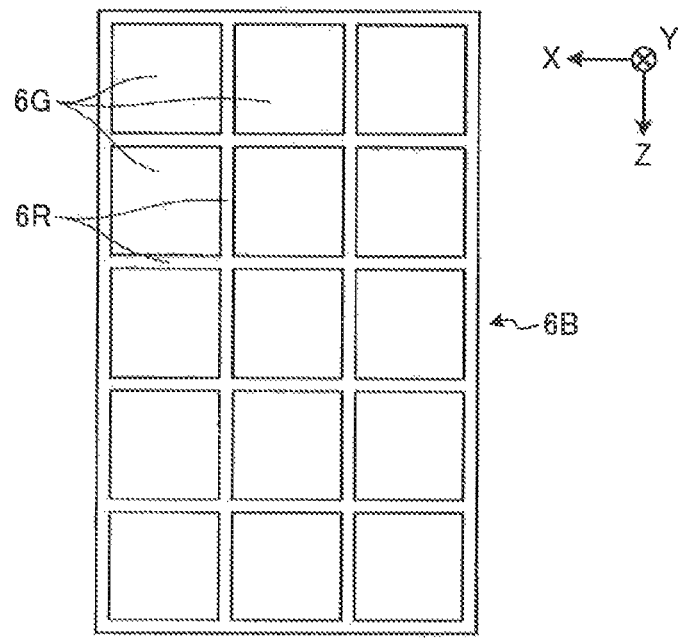
FIG. 5 is a bottom view illustrating an example of a support body in a device according to an embodiment.

FIG. 1 is a diagram illustrating an example of a device according to an embodiment. FIG. 2 is a perspective view illustrating an example of a support body in the device according to the embodiment. FIG. 3 is a side view illustrating a first side wall of the support body illustrated in FIG. 2. FIG. 4 is a side view illustrating a second side wall of the support body illustrated in FIG. 2. FIG. 5 is a bottom view illustrating an example of the support body in the device according to the embodiment. A detection device 1 according to the present embodiment, which serves as an X-ray device, irradiates a subject S, serving as a measurement object, with X-rays XL and detects transmitted X-rays transmitted through the subject S. The X-rays are electromagnetic waves having a wavelength of 1 pm to 30 nm, for example. The X-rays include at least one of ultrasoft X-rays at approximately 50 eV, soft X-rays at approximately 0.1 keV to 2 keV, X-rays from approximately 2 to 20 keV, and hard X-rays from approximately 20 to 100 keV.

In the present embodiment, the detection device 1 includes an X-ray CT scanning device that irradiates the subject S with X-rays, detects the transmitted X-rays transmitted through the subject S, and obtains information of the interior of the subject S (an internal structure, for example) in a non-invasive manner. In the present embodiment, the subject S includes industrial components such as mechanical components, or electronic components. The X-ray CT scanning device includes an industrial X-ray CT scanning device that scans an industrial component by irradiating the industrial component with X-rays.

As illustrated in FIG. 1, the detection device 1 includes an X-ray source 2 that emits the X-rays XL, a table 3 serving as a stage that supports the subject S, a detector 4 that detects at least a portion of the transmitted X-rays emitted from the X-ray source 2 and transmitted through the subject S supported by the table 3, and a guide device 5 that guides movement of the table 3 in a direction parallel to an optical axis of the X-rays XL while supporting the table 3. The direction parallel to the optical axis of the X-rays XL is the Z-axis direction. In the present embodiment, the table 3 is supported by a table support body 7. The table 3 may have any configuration that provides a function for supporting the subject S, and may further include a mechanism for moving in at least one of the X-axis direction, the Y-axis direction, the Z-axis direction, the θX direction, the θY direction, and the θZ direction. The guide device 5 guides movement of the table support body 7 in the direction parallel to the optical axis of the X-rays XL. According to such a structure, the table 3 is guided by the guide device 5 using the table support body 7, and moves in the direction parallel to the optical axis of the X-rays XL.

In the present embodiment, the detection device 1 includes a support body 6 to which the X-ray source 2, the detector 4, and the guide device 5 are attached. The X-ray source 2, the detector 4, and the guide device 5 are supported by the same support body 6. According to this configuration, the X-ray source 2, the detector 4, and the guide device 5 each move in the same manner together with the support body 6, and thus changes in positional relationships therebetween in the case where the orientations of those elements have changed can be reduced as compared to a case where those elements are attached to separate structures. As a result, the detection device 1 can suppress a drop in detection accuracy caused by changes in the positional relationships between the X-ray source 2, the detection device 4, and the guide device 5.

As illustrated in FIG. 2, the support body 6 includes a first side wall 6SA serving as a first support member, a second side wall 6SB serving as a second support member, and a base portion 6B serving as a third support member. The first side wall 6SA and the second side wall 6SB are connected by a third side wall 6SC provided on a first end portion 6SA1 and 6SB1 side thereof and serving as a fourth support member and a fourth side wall 6SD provided on a second end portion 6SA2 and 6SB2 side thereof and serving as a fifth support member. The first side wall 6SA, the second side wall 6SB, the third side wall 6SC, and the fourth side wall 6SD are plate-shaped or wall-shaped portions extending upright from the base portion 6B, which is a plate-shaped portion. To be more specific, the first side wall 6SA, the second side wall 6SB, the third side wall 6SC, and the fourth side wall 6SD extend upright from corner portions of the base portion 6B, which is rectangular in shape, as illustrated in FIG. 5. The first side wall 6SA, the second side wall 6SB, the third side wall 6SC, the fourth side wall 6SD, and the base portion 6B are all rectangular in shape when viewed from a direction orthogonal to the surface of those walls.

The first side wall 6SA and the second side wall 6SB oppose each other, and the wall surfaces thereof are parallel. The third side wall 6SC and the fourth side wall 6SD oppose each other, and the wall surfaces thereof are parallel. The wall surface of the first side wall 6SA and the wall surface of the second side wall 6SB are orthogonal to the wall surface of the third side wall 6SC and the wall surface of the fourth side wall 6SD. Devices included in the detection device 1, such as the table 3 that supports the subject S and a mechanism that rotates the table 3, moves the table 3 in the X-axis direction or the Z-axis direction, and the like, are disposed in a space 6SP surrounded by the base portion 6B, the first side wall 6SA, the second side wall 6SB, the third side wall 6SC, and the fourth side wall 6SD.

The third side wall 6SC has a first protrusion 6SCX that protrudes outward from itself, as illustrated in FIGS. 2, 3, and 4. Like the third side wall 6SC, the fourth side wall 6SD has a second protrusion 6SDD that protrudes outward from itself. As illustrated in FIG. 1, an X-ray source support member 2S that supports the X-ray source 2 is attached to the first protrusion 6SCX. A detector support member 4S that supports the detector 4 is attached to the second protrusion 6SDD. According to this configuration, the X-ray source 2 is attached to the first end portion 6SA1 and 6SB1 side of the first side wall 6SA and the second side wall 6SB. The detector 4 is attached to the second end portion 6SA2 and 6SB2 side of the first side wall 6SA and the second side wall 6SB.

As illustrated in FIGS. 2 to 5, each of the first side wall 6SA, the second side wall 6SB, the third side wall 6SC, the fourth side wall 6SD, and the base portion 6B has a plurality of lightening portions 6G that are thinner (smaller in the dimension orthogonal to the plate surface) than other areas. In the present embodiment, the lightening portions 6G are quadrangular in shape. The thickness of an area 6R between adjacent lightening portions 6G is greater than that of the lightening portions 6G, and furthermore is greater than the dimensions of the two adjacent lightening portions 6G. In this manner, the areas 6R between adjacent lightening portions 6G serve as ribs of the first side wall 6SA, the second side wall 6SB, the third side wall 6SC, the fourth side wall 6SD, and the base portion 6B. The areas 6R between adjacent lightening portions 6G will be called ribs 6R as appropriate hereinafter.

Because the first side wall 6SA, the second side wall 6SB, the third side wall 6SC, the fourth side wall 6SD, and the base portion 6B have the lightening portions 6G, an increase in the mass of the support body 6 can be suppressed. Furthermore, because the first side wall 6SA, the second side wall 6SB, the third side wall 6SC, the fourth side wall 6SD, and the base portion 6B have the ribs 6R, a drop in the strength of the support body 6 caused by providing the plurality of lightening portions 6G can be suppressed.

In the present embodiment, the support body 6 is formed from a material having a low coefficient of linear expansion. For example, an alloy called invariable steel (invar or super invar) obtained by adding 36% nickel to iron can be used as the material having a low coefficient of linear expansion. Such a material is generally expensive. As described earlier, in the present embodiment, the support body 6 has the lightening portions 6G, which makes it possible to reduce the amount of material used for the support body 6. Accordingly, in the case where a material that has a low coefficient of linear expansion and is therefore expensive is used for the support body 6, an increase in the manufacturing cost of the support body 6 is suppressed by providing a plurality of the lightening portions 6G in the support body 6.

As described earlier, the X-ray source 2, the detector 4, and the guide device 5 are attached to the support body 6. The table 3 that supports the subject S is supported by the support body 6 using the table support body 7 and the guide device 5. By manufacturing the support body 6 using a material having a low coefficient of linear expansion, the dimensions of the support body 6 are suppressed from changing due to temperature even if the ambient temperature around the support body 6 has risen when the shape of the subject S is measured by the detection device 1 or the like. Changes in the relative positional relationships between the X-ray source 2, the detector 4, the guide device 5, and the table 3, caused by thermal expansion in the support body 6, are kept to a minimum as a result. Accordingly, the detection device 1 can keep to a minimum a drop in the accuracy of measuring the shape of the subject S or the like.

In the present embodiment, the first side wall 6SA, the second side wall 6SB, the third side wall 6SC, the fourth side wall 6SD, and the base portion 6B are manufactured as an integrated structure through casting or the like. The support body 6 can be manufactured with ease as a result. Note that the support body 6 may be manufactured through a manufacturing method aside from casting.

As illustrated in FIGS. 2, 3, and 4, the first side wall 6SA and the second side wall 6SB have a plurality of through-holes 6H that pass therethrough in the direction orthogonal to the wall surfaces thereof. The through-holes 6H are provided in mutually different positions in the wall surfaces of the first side wall 6SA and the second side wall 6SB, and to be more specific, are provided in mutually different positions in the Y-axis direction and the Z-axis direction. According to this configuration, the space 6SP of the support body 6 can be easily accessed from the plurality of through-holes 6H. It is therefore easy to clean and maintain the devices included in the detection device 1 that are disposed in the space 6SP. In addition, because the plurality of through-holes 6H are provided in mutually different positions in the Y-axis direction and the Z-axis direction, different areas of an internal space SP can be easily accessed by using different through-holes 6H. Accordingly, even if the devices provided in the detection device 1 are disposed in different positions in the space 6SP, it is easy to clean and maintain those devices.

In the present embodiment, the detection device 1 is housed within a chamber member 8 that forms the internal space SP through which the X-rays XL emitted from the X-ray source 2 travel. In the present embodiment, the detection device 1 is disposed within the internal space SP. In the present embodiment, the detection device 1 includes a supply port 26 that supplies a temperature-controlled gas G to at least part of the X-ray source 2. The supply port 26 is disposed within the internal space SP.

As illustrated in FIG. 1, the support body 6 has a plurality of legs 6F.

The plurality of legs 6F are attached to the base portion 6B of the support body 6 illustrated in FIG. 2. The legs 6F make contact with a base portion 8B of the chamber member 8. A bottom surface of the support body 6, or in other words, a surface that opposes the base portion 8B of the chamber member 8, is separated from the base portion 8B of the chamber member 8 by the legs 6F. In other words, a space is formed between the bottom surface of the support body 6 and the base portion 8B of the chamber member 8. Note that at least part of the bottom surface of the support body 6 may make contact with the base portion 8B of the chamber member 8. The base portion 6B of the support body 6 is disposed on the base portion 8B side of the chamber member 8, which is where the support body 6 is to be placed. In other words, the base portion 6B serves as the placement location for the detection device 1. Although the support body 6 of the detection device 1 is placed on the base portion 8B of the chamber member 8 in the present embodiment, the method for installing the support body 6 is not limited thereto. For example, the support body 6 may be suspended from a placement target using suspension wires or the like. Each of the plurality of legs 6F of the support body 6 includes a vibration control mechanism for suppressing vibrations from outside the detection device 1 from reaching, for example, the X-ray source 2 via the chamber member 8. The vibration control mechanism uses air springs or springs formed from metal, for example.

The vibration control mechanism need not be provided in all of the plurality of legs 6F.

In the present embodiment, the chamber member 8 is placed upon a support surface FR. The support surface FR includes a floor surface in a factory or the like. The chamber member 8 is supported by a plurality of legs 8S. The chamber member 8 is placed upon the support surface FR using the legs 8S. In the present embodiment, the legs 8S separate a bottom surface of the chamber member 8 from the support surface FR. In other words, a space is formed between the bottom surface of the chamber member 8 and the support surface FR. Note that at least part of the bottom surface of the chamber member 8 may make contact with the support surface FR. In the present embodiment, the chamber member 8 contains lead. The chamber member 8 suppresses the X-rays XL in the internal space SP from escaping to an external space RP of the chamber member 8.

In the present embodiment, the chamber member 8 includes a member having a lower thermal conductivity than that of the chamber member 8. In the present embodiment, this member is disposed on an outer surface of the chamber member 8. This member suppresses a temperature of the internal space SP from the influence of a temperature (a temperature change) of the external space RP. In other words, this member functions as an insulating member that suppresses heat from the external space RP from reaching the internal space SP. This member contains plastic, for example. In the present embodiment, this member includes expanded polystyrene or iron, for example. For example, iron may be disposed on an inner side of the chamber member. In this case, the iron member is disposed in addition to the lead member of the chamber member 8, and thus the strength of the chamber member 8 can be reinforced. Note that the chamber member 8 and the iron member may be in direct contact, or at least part of the chamber member 8 may be in contact with the iron member.

The X-ray source 2 irradiates the subject S with the X-rays XL. The X-ray source 2 includes an emitting portion 2E that emits the X-rays XL. The X-ray source 2 forms a point-source X-ray. In the present embodiment, the emitting portion 2E includes a point-source X-ray. The X-ray source 2 irradiates the subject S with X-rays in a conical shape (a so-called cone beam). Note that the X-ray source 2 may be capable of adjusting the intensity of the X-rays XL emitted. In the case where the intensity of the X-rays XL emitted from the X-ray source 2 is adjusted, the intensity of the X-rays XL may be adjusted on the basis of X-ray absorption characteristics and the like of the subject S. Meanwhile, the shape in which the X-rays emitted from the X-ray source 2 spread out is not limited to a conical shape, and the X-rays may be in a fan shape (a so-called fan beam) as well.

The emitting portion 2E faces in a +Z direction. The +Z direction is a direction facing from the X-ray source 2 toward the detector 4. In the present embodiment, at least a portion of the X-rays XL emitted from the emitting portion 2E travel in the +Z direction within the internal space SP.

The supply port 26 supplies the temperature-controlled gas G to at least part of the X-ray source 2. In the present embodiment, the detection device 1 includes an adjusting device 25 that controls the temperature of the gas G. The adjusting device 25 operates under electrical power, for example. The supply port 26 supplies the gas G from the adjusting device 25 to the internal space SP. In the present embodiment, the adjusting device 25 is disposed in the external space RP of the chamber member 8. The adjusting device 25 is placed on the support surface FR. The adjusting device 25 is connected to a pipe 26P. The pipe 26P connects the adjusting device 25 to the internal space SP of the chamber member 8.

The pipe 26P opens into the internal space SP of the chamber member 8. This opening functions as the supply port 26 that supplies the gas G to the internal space SP. In the present embodiment, the adjusting device 25 takes in a gas from the external space RP, for example, and adjusts the temperature of that gas. The gas G whose temperature has been adjusted by the adjusting device 25 is sent to the supply port 26 via the pipe 26P. The supply port 26 is disposed so as to oppose at least part of the X-ray source 2. The supply port 26 supplies the gas G from the adjusting device 25 to at least part of the X-ray source 2.

The detector 4 is disposed further on the +Z side than the X-ray source 2 and the table 3 in the internal space SP. The detector 4 opposes the emitting portion 2E of the X-ray source 2. The position of the detector 4 is fixed to a predetermined position. However, the detector 4 may be mobile. The table 3 can move between the X-ray source 2 and the detector 4 within the internal space SP. The detector 4 includes a scintillator portion 36 having an incidence surface 4DP on which the X-rays XL from the X-ray source 2, including the transmitted X-rays transmitted through the subject S, are incident, and a light-receiving portion 37 that receives light produced by the scintillator portion 36. The incidence surface 4DP of the detector 4 opposes the subject S supported by the table 3. The incidence surface 4DP is a surface of the detector 4 on which the X-rays are incident. In the present embodiment, at least one of the X-rays XL emitted from the X-ray source 2 and the transmitted X-rays emitted from the X-ray source 2 and transmitted through the subject S are incident on the incidence surface 4DP.

The scintillator portion 36 includes a scintillation material that emits light at a different wavelength than the X-rays XL upon being irradiated with those X-rays. The light-receiving portion 37 includes a photoelectric amplifier. The photoelectric amplifier includes a photoelectric tube that converts light energy into electrical energy using a photoelectric effect. The light-receiving portion 37 amplifies the light produced by the scintillator portion 36, converts the light into an electrical signal, and outputs the signal. The detector 4 includes a plurality of the scintillator portions 36. The plurality of the scintillator portions 36 are arranged in an XY plane. The scintillator portions 36 are arranged in array form. The detector 4 includes a plurality of the light-receiving portions 37 so that each is connected to a respective one of the plurality of scintillator portions 36. The detector 4 may directly convert the incident X-rays into an electrical signal without converting the X-rays into light.

Operations of the detection device 1 are controlled by a control device 9. The control device 9 controls operations of the X-ray source 2, computes the shape of the subject S from a result of the detector 4 detecting the transmitted X-rays transmitted through the subject S, controls the movement of the table 3, controls the operations of the adjusting device 25, and the like, for example. The control device 9 is a computer, for example.

Figure 6:
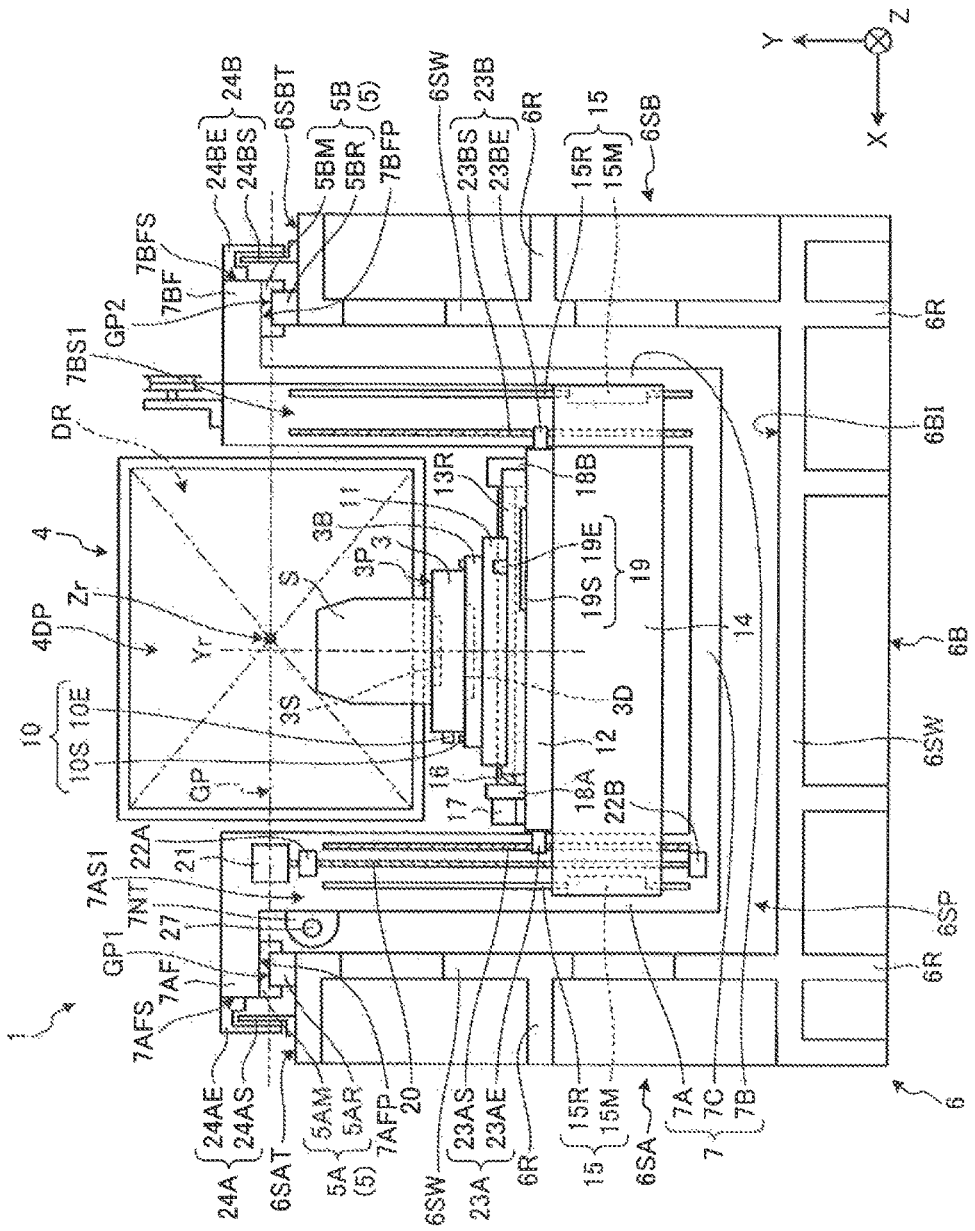
FIG. 6 is a diagram taken from A-A arrows indicated in FIG. 1.
Figure 7:
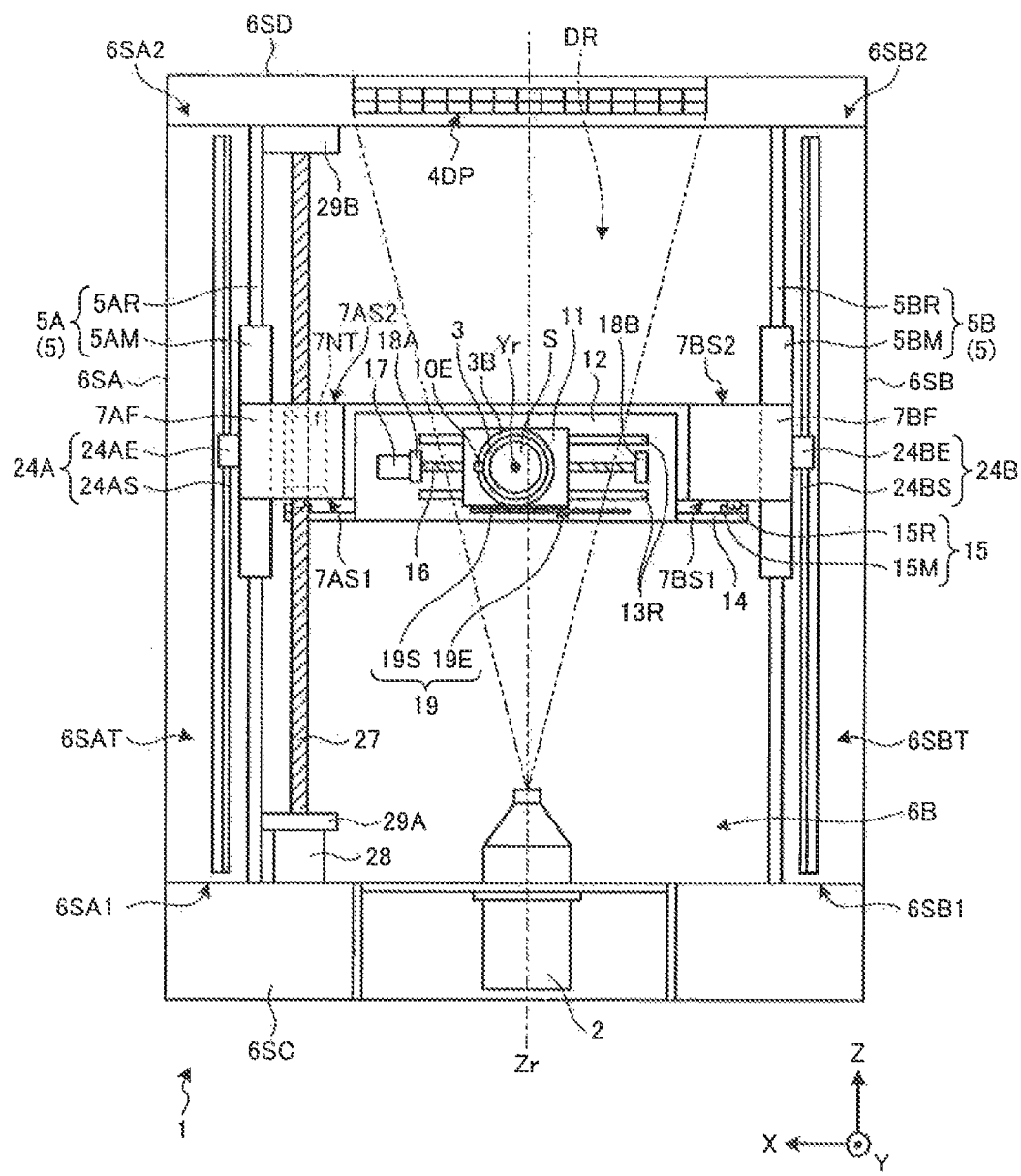
FIG. 7 is a top view of a detection device.
Figure 8:
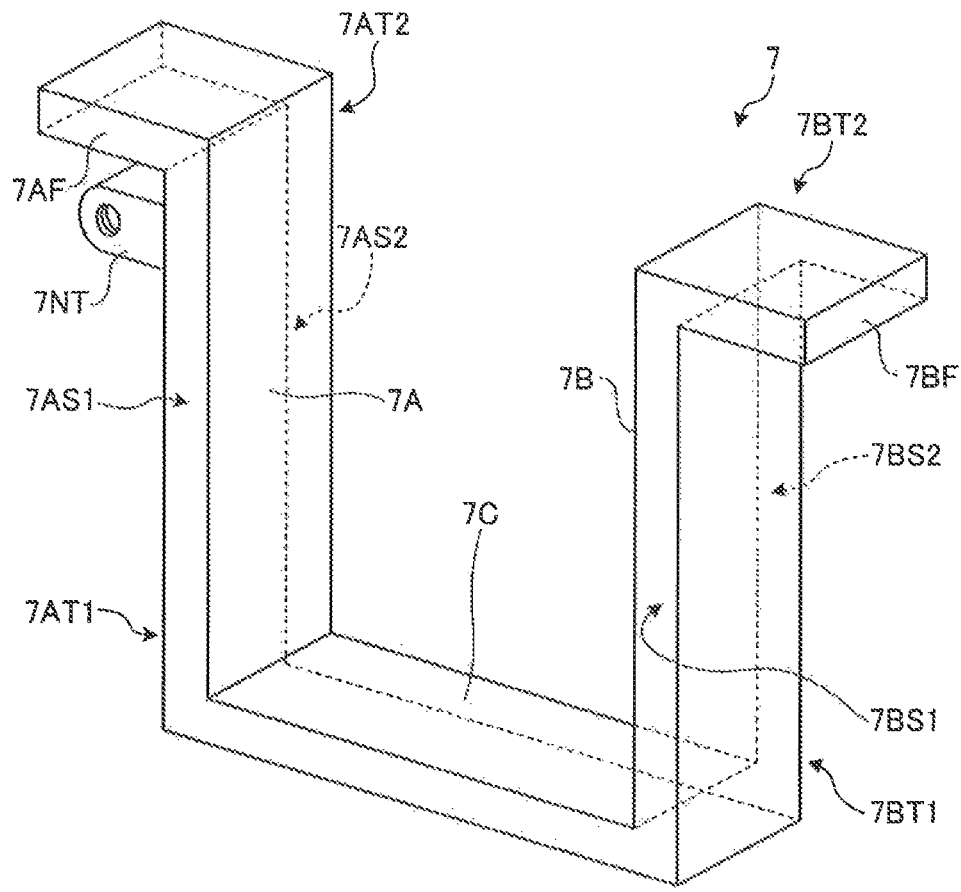
FIG. 8 is a perspective view illustrating a table support body provided in a detection device.

FIG. 6 is a diagram taken from A-A arrows indicated in FIG. 1. FIG. 7 is a top view of the detection device. FIG. 8 is a perspective view illustrating the table support body provided in the detection device. Reference numeral Zr in FIGS. 6 and 7 indicates the optical axis of the X-ray source 2. In the present embodiment, the optical axis Zr is parallel to the Z-axis. The same applies in the following examples. As illustrated in FIGS. 6 and 7, the table 3 is supported by a table main body 3B. The table 3 includes a support mechanism (also called an object support mechanism) 3S for supporting the subject S. The support mechanism 3S employs a system that suctions an object to be supported using negative pressure, for example. The support mechanism 3S is not limited to a suction system, and may employ a system that grasps the object to be supported using a member, for example. In the table 3, a surface on which the support mechanism 3S is provided and on which the support mechanism 3S supports the subject S serves as a support surface 3P. In the present embodiment, the optical axis of the X-ray source 2 is a line that connects an emission point of the X-rays emitted from the X-ray source 2 to a center of the plurality of light-receiving portions 37 of the detector 4. The center of the plurality of light-receiving portions 37 of the detector 4 is, in FIG. 1, a point where center lines of the X-axis direction and the Y-axis direction intersect with each other.

The table main body 3B supports the table 3 and is anchored to an attachment target area of the table 3. The table main body 3B includes a rotational driving device 3D for rotating around an axis Yr that is orthogonal to the support surface 3P of the table 3. The axis Yr that is orthogonal to the support surface 3P of the table 3 will be called a table rotation axis Yr as appropriate hereinafter. The table rotation axis Yr is an axis parallel to the Y-axis, and thus the table 3 rotates in the θY direction. The rotational driving device 3D includes an electric motor, for example, and rotates the table 3 under rotational force from the electric motor.

The table 3 includes a rotary encoder 10 for measuring a rotation amount (position in the θY direction) of the table 3. The rotary encoder 10 includes, for example, a scale member 10S provided on the table main body 3B and an encoder head 10E that is provided on the table 3 and detects points on the scale member 10S. According to this configuration, the rotary encoder 10 measures the rotation amount of the table 3 relative to the table main body 3B. The control device 9 illustrated in FIG. 1 controls the rotation amount of the table 3 by controlling operations of the rotational driving device 3D on the basis of the rotation amount of the table 3 measured by the rotary encoder 10, for example.

The table main body 3B is attached to a first mobile member 11. The first mobile member 11 is supported by rails 13R, serving as a guide member, that is attached to a base 12. The base 12 is attached to a second mobile member 14. The second mobile member 14 is attached to the table support body 7 using guide mechanisms 15 provided between the table support body 7 and the second mobile member 14. In this manner, the table 3 is supported by the table support body 7 by the table main body 3B, the first mobile member 11, the rails 13R, the base 12, the second mobile member 14, and the guide mechanisms 15.

As illustrated in FIG. 7, the base 12 includes a plurality (two, in the present embodiment) of rails 13R and 13R disposed at a predetermined interval and substantially parallel to each other, on the first mobile member 11 side. The two rails 13R and 13R extend in the X-axis direction. The first mobile member 11 is guided by the rails 13R and 13R and moves along the rails 13R and 13R in the X-axis direction. The first mobile member 11 has a screw shaft 16 screwed into a nut provided in the first mobile member 11. The screw shaft 16 is attached to an output shaft of an actuator 17. In the present embodiment, the actuator 17 is an electric motor. The actuator 17 rotates the screw shaft 16. The screw shaft 16 is rotatably supported by shaft receivers 18A and 18B, which are supported by the base 12. In the present embodiment, the screw shaft 16 is supported by the shaft receivers 18A and 18B so that the axis line of the screw shaft 16 is substantially parallel to the X-axis.

When the actuator 17 rotates, the screw shaft 16 also rotates. The screw shaft 16 is screwed into the nut provided in the first mobile member 11, and thus when the screw shaft 16 rotates, the first mobile member 11 moves in the X-axis direction. In the present embodiment, a ball is disposed between the nut provided in the first mobile member 11 and the screw shaft 16. In other words, the first mobile member 11 moves in the X-axis direction using a ball screw mechanism. At this time, as described earlier, the two rails 13R and 13R guide the movement of the first mobile member 11 in the X-axis direction.

The movement amount (position in the X-axis direction) of the first mobile member 11 is detected by a linear encoder 19. The linear encoder 19 includes an encoder head 19E and a linear scale 19S. The linear scale 19S is attached to the base 12 on the first mobile member 11 side thereof. The encoder head 19E is attached to the first mobile member 11 at a position that opposes the linear scale 19S. The linear encoder 19 measures the movement amount of the first mobile member 11 relative to the base 12 in the X-axis direction. The control device 9 illustrated in FIG. 1 controls the movement amount of the first mobile member 11 by controlling operations of the actuator 17 on the basis of the movement amount of the first mobile member 11 measured by the linear encoder 19, for example. In other words, the control device 9 controls the movement amount of the table 3 in the X-axis direction on the basis of the movement amount of the first mobile member 11 measured by the linear encoder 19.

As illustrated in FIGS. 6 and 7, the second mobile member 14 attached to the base 12 is attached to and supported by the table support body 7 using a plurality (two, in the present embodiment) of guide mechanisms 15 and 15. Each guide mechanism 15 includes a rail 15R serving as a guide member and a movement member 15M. The movement member 15M is attached to the rail 15R, and movement thereof is guided by the rail 15R in the direction in which the rail 15R extends. According to this structure, the second mobile member 14 can move in a direction orthogonal to the support surface 3P of the table 3. The rail 15R is attached to the table support body 7.

As illustrated in FIGS. 6 and 8, the table support body 7 includes a first member 7A, a second member 7B, and a third member 7C. The first member 7A is disposed on the first side wall 6SA side of the support body 6. The second member 7B is disposed on the second side wall 6SB side of the support body 6. As illustrated in FIG. 8, the third member 7C connects a first end portion 7AT1 of the first member 7A and a first end portion 7BT1 of the second member 7B. In the present embodiment, the first member 7A, the second member 7B, and the third member 7C are all plate-shaped members. Plate surfaces of the first member 7A and the second member 7B oppose each other.

The first member 7A, the second member 7B, and the third member 7C are disposed onside of a detection region DR, which serves as a region where the transmitted X-rays transmitted through the subject S are detected by the detector 4. Relative to the detector 4, the first member 7A, the second member 7B, and the third member 7C are disposed on the outside of the incidence surface 4DP of the detector 4, as illustrated in FIGS. 6 and 7. According to this structure, the table support body 7 can avoid interfering with the detection region DR, and thus the entire detection region DR of the detection device 1 can be used. The detection region DR will be described later.

In the present embodiment, the table support body 7 is manufactured through a manufacturing method such as casting or forging, for example, so that the first member 7A, the second member 7B, and the third member 7C are a single integrated structure. The table support body 7 can be manufactured with ease as a result. The table support body 7 manufactured as a single integrated structure through the aforementioned manufacturing method can have a greater level of rigidity and strength than in the case where the first member 7A, the second member 7B, and the third member 7C are manufactured as separate components and are assembled using fastening members such as bolts. Note that this does not preclude the table support body 7 from being manufactured using a manufacturing method aside from casting or forging.

In the present embodiment, the table support body 7 is manufactured from a material having a low coefficient of linear expansion (invariable steel, for example), in the same manner as the aforementioned support body 6. The material having a low coefficient of linear expansion is as described earlier. By manufacturing the table support body 7 using a material having a low coefficient of linear expansion, the dimensions of the table support body 7 are suppressed from changing due to temperature even if the ambient temperature around the table support body 7 has risen when the shape of the subject S is measured by the detection device 1 or the like. As a result, positional skew of the subject S caused by thermal expansion of the table support body 7 can be kept to a minimum. Accordingly, the detection device 1 can keep to a minimum a drop in the accuracy of measuring the shape of the subject S or the like.

One of the two rails 15R and 15R is attached to a side portion 7AS1 of the first member 7A of the table support body 7. The other rail 15R is attached to a side portion 7BS1 of the second member 7B of the table support body 7. The side portion 7AS1 of the first member 7A and the side portion 7BS1 of the second member 7B are side portions located on the X-ray source 2 side, as illustrated in FIG. 7. Rather than being attached to the side portions 7AS1 and 7AS2 on the X-ray source 2 side, the two rails 15R and 15R may be attached to a side portion 7AS2 on the detector 4 side of the first member 7A and a side portion 7BS2 on the detector 4 side of the second member 7B, which are indicated in FIG. 7.

The rail 15R attached to the first member 7A and the rail 15R attached to the second member 7B are disposed so as to be substantially parallel. The two rails 15R and 15R extend in the Y-axis direction. The second mobile member 14 includes the movement members 15M and 15M that are attached to and guided by the respective rails 15R and 15R. According to this configuration, the second mobile member 14 is guided by the rails 15R and 15R using the movement members 15M and 15M and moves in the Y-axis direction along the rails 15R and 15R.

As illustrated in FIG. 6, the second mobile member 14 has a screw shaft 20 screwed into a nut provided in the first mobile member 11. The screw shaft 20 is attached to an output shaft of an actuator 21. The actuator 21 and the screw shaft 20 constitute a movement mechanism that moves the table 3 parallel to a direction orthogonal to the support surface 3P of the table 3 on which the subject S is supported. In the present embodiment, the actuator 21 is an electric motor. The actuator 21 rotates the screw shaft 20. The screw shaft 20 is rotatably supported by shaft receivers 22A and 22B supported by the table support body 7, and more specifically, supported by the first member 7A of the table support body 7. In the present embodiment, the screw shaft 20 is supported by the shaft receivers 22A and 22B so that the axis line of the screw shaft 20 is substantially parallel to the Y-axis.

When the actuator 21 rotates, the screw shaft 20 also rotates. The screw shaft 20 is screwed into the nut provided in the second mobile member 14, and thus when the screw shaft 20 rotates, the second mobile member 14 moves in the Y-axis direction. In the present embodiment, a ball is disposed between the nut provided in the second mobile member 14 and the screw shaft 20. In other words, the second mobile member 14 moves in the Y-axis direction using a ball screw mechanism. At this time, as described earlier, the two rails 15R and 15R guide the movement of the second mobile member 14 in the Y-axis direction.

The table support body 7 includes a plurality (two, in the present embodiment) of linear encoders 23A and 23B. The number of the linear encoders 23A and 23B the table support body 7 includes is not limited, and one, or three or more, may be provided. The movement amount (position in the Y-axis direction) of the second mobile member 14 is detected by at least one of the linear encoder 23A and the linear encoder 23B. The linear encoder 23A includes an encoder head 23AE and a linear scale 23AS serving as a first scale. The linear encoder 23B includes an encoder head 23BE and a linear scale 23BS serving as a second scale. The linear scale 23AS is attached to the side portion 7AS1 of the first member 7A of the table support body 7. The linear scale 23BS is attached to the side portion 7BS1 of the second member 7B of the table support body 7. The linear scale 23AS can be used to measure the length of the first member 7A, and the linear scale 23BS can be used to measure the length of the second member 7B.

The encoder head 23AE is attached in a position, on the base 12 supported by the second mobile member, that opposes the linear scale 23AS attached to the first member 7A. The encoder head 23BE is attached in a position, on the base 12 supported by the second mobile member, that opposes the linear scale 23BS attached to the second member 7B. The linear encoders 23A and 23B measure the movement amount of the base 12 and the second mobile member 14 relative to the table support body 7 in the Y-axis direction. The control device 9 illustrated in FIG. 1 controls the movement amount of the base 12 and the second mobile member 14 by controlling operations of the actuator 21 on the basis of the movement amount of the base 12 and the second mobile member 14 measured by at least one of the linear encoder 23A and the linear encoder 23B, for example. In other words, the control device 9 controls the movement amount of the table 3 in the Y-axis direction on the basis of the movement amount of the base 12 and the second mobile member 14 measured by the linear encoder 23A and the like.

In the present embodiment, at least one of the two linear encoders 23A and 23B included in the table support body 7 can measure the length, in the Y-axis direction, of at least one of the first member 7A and the second member 7B of the table support body 7. In this case, the linear scale 23AS is used to measure the length of the first member 7A, and specifically the length thereof in the Y-axis direction, and the linear scale 23BS is used to measure the length of the second member 7B, and specifically the length thereof in the Y-axis direction. In the present embodiment, a length in the Y-axis direction is a length in a direction parallel to the table rotation axis Yr.

The lengths of the first member 7A and the second member 7B in the Y-axis direction change depending on the mass of the subject S supported by the table 3. Accordingly, extension of the first member 7A and the second member 7B in the Y-axis direction (extension toward the base portion 6B of the support body 6) caused by the subject S is found by measuring the length, in the Y-axis direction, of at least one of the first member 7A and the second member 7B while the table 3 is supporting the subject S. The control device 9 operates the actuator 21 and moves the table 3 in the direction opposite from the base portion 6B of the support body 6 by an amount equivalent to the stated extension measured by at least one of the two linear encoders 23A and 23B. Doing so makes it possible to correct the extension of the first member 7A and the second member 7B in the Y-axis direction caused by the mass of the subject S supported by the table 3, and thus positional skew of the subject S in the Y-axis direction caused by the mass of the subject S can be corrected and the position of the table 3 in the Y-axis direction can be controlled. As a result, the detection device 1 can suppress a drop in the accuracy of measuring the shape of the subject S or the like.

In the case where the lengths of the first member 7A and the second member 7B in the Y-axis direction are found, at least one of the two linear encoders 23A and 23B may measure the length of the first member 7A or the second member 7B in the Y-axis direction. In the case where the lengths of the first member 7A and the second member 7B in the Y-axis direction are found, a tilt of the table 3 central to the Z-axis (a tilt of the table 3 relative to the XY plane) is found by using both of the linear encoders 23A and 23B. By using measurement values from the two linear encoders 23A and 23B, the control device 9 can more accurately find positional skew of the subject S in the Y-axis direction caused by the mass of the subject S itself and control the position of the table 3 in the Y-axis direction. As a result, the detection device 1 can suppress a drop in the accuracy of measuring the shape of the subject S or the like.

Even in the case where the position of the base 12 in the Y direction is detected and the position of the table 3 in the Y-axis direction is controlled, the tilt of the table 3 central to the Z-axis (the tilt of the table 3 relative to the XY plane) is found by using the two linear encoders 23A and 23B. By using measurement values from the two linear encoders 23A and 23B, the control device 9 can more accurately find positional skew of the subject S in the Y-axis direction caused by the mass of the subject S itself and control the position of the table 3 in the Y-axis direction. As a result, the control device 9 can accurately control the position of the subject S in the Y-axis direction. In this manner, it is preferable that the detection device 1 include the linear encoders 23A and 23B in the first member 7A and the second member 7B, respectively, of the table support body 7, and that the control device 9 control and correct the position of the table 3 in the Y-axis direction on the basis of measurement results from both.

As illustrated in FIG. 6, the table support body 7 is attached to and supported by the support body 6 using a first guide device 5A, which is a part of the guide device 5 illustrated in FIG. 1, and a second guide device 5B, which is also a part of the guide device 5. The first guide device 5A includes a rail 5AR serving as a guide member, and a movement member 5AM that is guided in the direction in which the rail 5AR extends. The second guide device 5B includes a rail 5BR serving as a guide member, and a movement member 5BM that is guided in the direction in which the rail 5BR extends.

As illustrated in FIG. 8, the table support body 7 has a first flange portion 7AF on a second end portion 7AT2 side of the first member 7A, which is the opposite side from the third member 7C, and a second flange portion 7BF on a second end portion 7BT2 side of the second member 7B, which is the opposite side from the third member 7C. The first flange portion 7AF protrudes from the end portion 7AT2 of the first member 7A in the opposite direction from the second member 7B, in the X-axis direction. The second flange portion 7BF protrudes from the end portion 7BT2 of the second member 7B in the opposite direction from the first member 7A, in the X-axis direction.

When the table support body 7 is disposed in the internal space SP of the support body 6, the first flange portion 7AF protrudes to a position that overlaps with an end surface 6SAT of the first side wall 6SA on the side opposite from the base portion 6B of the support body 6, and the second flange portion 7BF protrudes to a position that overlaps with an end surface 6SBT of the second side wall 6SB on the side opposite from the base portion 6B of the support body 6. The end surface 6SAT of the first side wall 6SA and the base portion 6B of the support body 6 are connected by a wall portion 6SW of the first side wall 6SA. The end surface 6SBT of the second side wall 6SB and the base portion 6B of the support body 6 are connected by a wall portion 6SW of the second side wall 6SB. The wall portion 6SW rises, from a base surface 6BI serving as a surface of the base portion 6B on the side thereof where the first side wall 6SA and the second side wall 6SB are located, in a direction substantially orthogonal to the base surface 6BI. Note that the ribs 6R rise from the wall surface of the wall portion 6SW in a direction substantially orthogonal to the wall surface.

The rail 5AR of the first guide device 5A is attached to the end surface 6SAT of the first side wall 6SA. The rail 5BR of the second guide device 5B is attached to the end surface 6SBT of the second side wall 6SB. As illustrated in FIGS. 6 and 7, the end surface 6SAT of the first side wall 6SA and the end surface 6SBT of the second side wall 6SB are disposed with the optical axis Zr located therebetween. In other words, the end surface 6SAT of the first side wall 6SA and the end surface 6SBT of the second side wall 6SB are disposed on either side of the optical axis Zr. Accordingly, the first guide device 5A whose rail 5AR is attached to the end surface 6SAT of the first side wall 6SA and the second guide device 5B whose rail 5BR is attached to the end surface 6SBT of the second side wall 6SB are disposed on either side of the optical axis Zr. Furthermore, as illustrated in FIG. 6, in the present embodiment, the first guide device 5A and the second guide device 5B are disposed on the outside of the detection region DR.

The first guide device 5A is disposed between the first flange portion 7AF of the table support body 7 and the end surface 6SAT of the first side wall 6SA. The second guide device 5B is disposed between the second flange portion 7BF of the table support body 7 and the end surface 6SBT of the second side wall 6SB. The first member 7A and the second member 7B extend from the first guide device 5A and the second guide device 5B toward the installation location side of the detection device 1, or in other words, toward the base portion 6B of the support body 6. The third member 7C connects the first member 7A and the second member 7B on the installation location side, or in other words, on the side of the base portion 6B of the support body 6. According to this configuration, the table support body 7 is supported by the support body 6 at two locations in the direction in which the third member 7C extends, or in other words, in the direction from the first member 7A toward the second member 7B or the opposite direction therefrom. That is, the table support body 7 is attached to and supported by the support body 6 through a dual-sided support structure. Accordingly, the table support body 7 can experience less warping under loads than in the case where the table support body 7 is supported by the support body 6 using a single-sided support structure. The table support body 7 supports the table 3, which supports the subject S, and thus reducing warping on the table support body 7 under loads also makes it possible to reduce positional skew of the subject S supported by the table 3. As a result, the detection device 1 can suppress a drop in the detection accuracy.

The rail 5AR of the first guide device 5A is provided in a position that overlaps with the wall portion 6SW of the first side wall 6SA. The rail 5BR of the second guide device 5B is provided in a position that overlaps with the wall portion 6SW of the second side wall 6SB. According to this structure, loads on the table support body 7, the table 3, and the like transmitted to the support body 6 from the rail 5AR of the first guide device 5A and the rail 5BR of the second guide device 5B are received by the wall portions 6SW of the first side wall 6SA and the second side wall 6SB and are then transmitted to the base portion 6B of the support body 6. In the detection device 1, the wall portions 6SW are present between the rails 5AR and 5BR and the base portion 6B, and thus positional skew of the first guide device 5A and the second guide device 5B in the Y-axis direction is suppressed.

As illustrated in FIG. 6, the ribs 6R rise from the wall portion 6SW of the base portion 6B in a direction substantially orthogonal to the wall surface thereof. In the present embodiment, the ribs 6R of the base portion 6B, and the wall portion SW of the first side wall 6SA and the wall portion 6SW of the second side wall 6SB, are provided in overlapping positions with the wall portion 6SW of the base portion 6B located therebetween. According to this structure, warping of the wall portion 6SW of the base portion 6B caused by loads transmitted from the wall portion 6SW of the first side wall 6SA and the wall portion 6SW of the second side wall 6SB to the wall portion 6SW of the base portion 6B is kept to a minimum by the ribs 6R of the base portion 6B provided on the opposite side from the first side wall 6SA and the second side wall 6SB. Positional skew of the first guide device 5A and the second guide device 5B in the Y-axis direction is suppressed as a result.

The rail 5AR of the first guide device 5A and the rail 5BR of the second guide device 5B extend in a direction parallel to the optical axis Zr, as illustrated in FIG. 7. The movement member 5AM of the first guide device 5A is integrated with the rail 5AR, and the movement of the movement member 5AM is then guided by the rail 5AR. The movement member 5BM of the second guide device 5B is integrated with the rail 5BR, and the movement of the movement member 5BM is then guided by the rail 5BR. In other words, the movement member 5AM and the movement member 5BM are guided by the rail 5AR and the rail 5BR in the direction parallel to the optical axis Zr.

As illustrated in FIG. 6, the movement member 5AM of the first guide device 5A is attached to a surface 7AFP on the third member 7C side of the first flange portion 7AF provided in the first member 7A of the table support body 7. The movement member 5BM of the second guide device 5B is attached to a surface 7BFP on the third member 7C side of the second flange portion 7BF provided in the second member 7B of the table support body 7. The rails 5AR and 5BR of the first guide device 5A and the second guide device 5B are attached to the support body 6 as described earlier, and thus the table support body 7 is attached to the support body 6 using the first guide device 5A and the second guide device 5B. Movement of the first member 7A of the table support body 7 parallel to the optical axis Zr is guided by the first guide device 5A. Movement of the second member 7B of the table support body 7 parallel to the optical axis Zr is guided by the second guide device 5B. As a result, the table support body 7 can move in a direction parallel to the optical axis Zr using the first guide device 5A and the second guide device 5B.

As described earlier, the table 3 is attached to the table support body 7 using the first mobile member 11 and the second mobile member 14. Accordingly, the table 3 is attached to the support body 6 using the table support body 7. The table 3 can therefore move, via the table support body 7, in a direction parallel to the optical axis Zr using the first guide device 5A and the second guide device 5B. In other words, the first guide device 5A is disposed on the outside of the detection region DR, and guides the movement of the table 3 in a direction parallel to the optical axis Zr while supporting the table 3. The second guide device 5B is disposed on the outside of the detection region DR in a different position than the first guide device 5A, and guides the movement of the table 3 in a direction parallel to the optical axis Zr while supporting the table 3.

As illustrated in FIG. 6, the first guide device 5A includes a first guide plane GP1 that is parallel to the optical axis Zr and regulates the movement of at least one of the X-ray source 2, the table 3, and the detector 4. The second guide device 5B includes a second guide plane GP2 that is parallel to the optical axis Zr and regulates the movement of at least one of the X-ray source 2, the table 3, and the detector 4. In the present embodiment, at least one of the X-ray source 2 and the detector 4 may be mobile. In this case, the movement of at least one of the X-ray source 2 and the detector 4 may be guided by the first guide device 5A and the second guide device 5B. Taking a plane that passes through at least part of the first guide plane GP1 and at least part of the second guide plane GP2 as a guide plane GP, the guide plane GP passes through the detection region DR for the transmitted X-rays detected by the detector 4. In the present embodiment, the guide plane GP passes through the detection region DR in a direction orthogonal to the support surface 3P of the table 3 on which the subject S is supported. In the example illustrated in FIG. 6, the guide plane GP is a plane parallel to and including the first guide plane GP1 and the second guide plane GP2. The guide plane GP is a plane that regulates the movement of the table 3. The guide plane GP will be described later.

As illustrated in FIGS. 6 and 7, the table support body 7 has a screw shaft 27 screwed into a nut 7NT provided in the table support body 7. Although the nut 7NT is provided in the first member 7A of the table support body 7 in the present embodiment as illustrated in FIGS. 6 and 8, the nut 7NT may be provided in the second member 7B or the third member 7C. The screw shaft 27 is attached to an output shaft of an actuator 28 illustrated in FIG. 7. In the present embodiment, the actuator 28 is an electric motor. The actuator 28 rotates the screw shaft 27. The screw shaft 27 is rotatably supported by shaft receivers 29A and 29B supported by the support body 6, and more specifically, supported by the first side wall 6SA of the support body 6. In the present embodiment, the screw shaft 27 is supported by the shaft receivers 29A and 29B so that the axis line of the screw shaft 27 is substantially parallel to the optical axis Zr.

When the actuator 28 rotates, the screw shaft 27 also rotates. The screw shaft 27 is screwed into the nut 7NT provided in the table support body 7, and thus when the screw shaft 27 rotates, the table support body 7 moves in the optical axis Zr direction. In the present embodiment, a ball is disposed between the nut 7NT provided in the table support body 7 and the screw shaft 27. In other words, the table support body 7 moves in the optical axis Zr direction using a ball screw mechanism. At this time, as described earlier, the two rails 5AR and 5BR guide the movement of the table support body 7 in the optical axis Zr direction.

The support body 6 includes a plurality (two, in the present embodiment) of linear encoders 24A and 24B. The number of the linear encoders 24A and 24B the support body 6 includes is not limited, and one, or three or more, may be provided. The movement amount (position in the optical axis Zr direction) of the table support body 7 is detected by at least one of the linear encoder 24A and the linear encoder 24B. The linear encoder 24A includes an encoder head 24AE and a linear scale 24AS. The linear encoder 24B includes an encoder head 24BE and a linear scale 24BS.

The linear scale 24AS serving as a first scale and the linear scale 24BS serving as a second scale each has a pattern arranged in a first direction (the optical axis Zr direction, in the present embodiment). The linear scale 24AS is anchored to the end surface 6SAT of the first side wall 6SA included in the support body 6. The linear scale 24BS serving as the second scale is anchored to the end surface 6SBT of the second side wall 6SB included in the support body 6. The encoder head 24AE, which serves as a first measurement device, detects the pattern of the linear scale 24AS and measures the position of the table support body 7, serving as a mobile device, in the first direction (the optical axis Zr direction, in the present embodiment). The encoder head 24BE, which serves as a second measurement device, detects the pattern of the linear scale 24BS and measures the position of the table support body 7, serving as a movement device, in the first direction. In the present embodiment, the encoder heads 24AE and 24BE are disposed in a second direction (the X-axis direction, in the present embodiment) that is orthogonal to the first direction (the optical axis Zr direction, in the present embodiment) in a mobile region of the movement device. The encoder head 24AE is attached to a side surface 7AFS on the side of the first flange portion 7AF of the table support body 7 that is opposite from the second flange portion 7BF. The encoder head 24BE is attached to a side surface 7BFS on the side of the second flange portion 7BF of the table support body 7 that is opposite from the first flange portion 7AF. In this manner, the encoder heads 24AE and 24BE are supported by the table support body 7 serving as a movement device. In addition, in the present embodiment, the encoder heads 24AE and 24BE are disposed with the optical axis Zr located therebetween. The two linear encoders 24A and 24B are disposed on either side of the optical axis Zr, on the outside of the detection region DR. In other words, the two linear encoders 24A and 24B are disposed on the outside of the detection region DR and on either side of the detection region DR.

The linear encoders 24A and 24B measure the movement amount of the table support body 7 relative to the support body 6 in the optical axis Zr direction. The control device 9 illustrated in FIG. 1 controls the movement amount of the table support body 7 by controlling operations of the actuator 28 on the basis of the movement amount of the table support body 7 measured by at least one of the linear encoder 24A and the linear encoder 24B, for example. In other words, the control device 9 controls the movement amount of the table 3 in the optical axis Zr direction on the basis of the movement amount of the table support body 7 measured by the linear encoder 24A and the like.

In the case where the position of the table 3 in the optical axis Zr is controlled by detecting the position of the table support body 7 in the optical axis Zr direction, a tilt of the table support body 7 central to the table rotation axis Yr or the Y-axis (a tilt of the table support body 7 relative to the ZY plane) is found by using both of the two linear encoders 24A and 24B disposed on the outside of the detection region DR with the detection region DR located therebetween. By using measurement values from the two linear encoders 24A and 24B, the control device 9 can more accurately find positional skew of the subject S in the optical axis Zr direction caused by the tilt of the table support body 7 central to the table rotation axis Yr or the Y-axis and control the position of the table 3. As a result, the control device 9 can accurately control the position of the subject S in the optical axis Zr direction. In this manner, it is preferable that the detection device 1 include the linear encoders 24A and 24B on either side of the optical axis Zr, and that the control device 9 control the position of the table 3 in the optical axis Zr direction on the basis of measurement results from the two.

Figure 9:
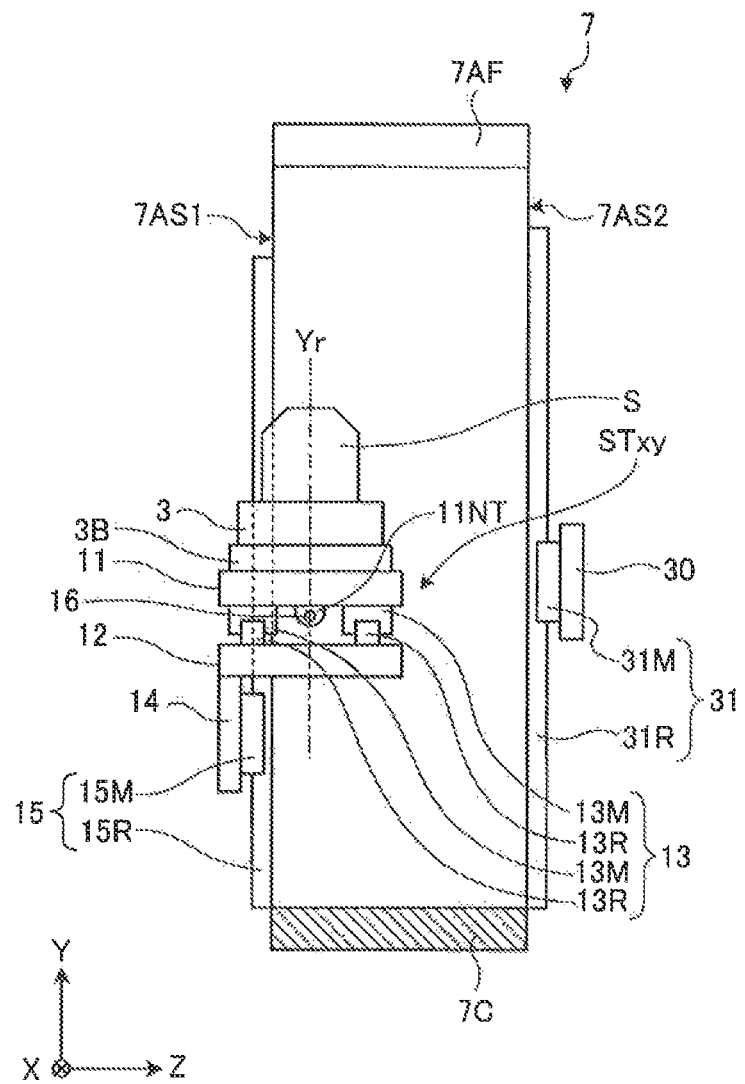
FIG. 9 is a diagram illustrating a structure for moving in a direction of a table rotation axis.
Figure 10:
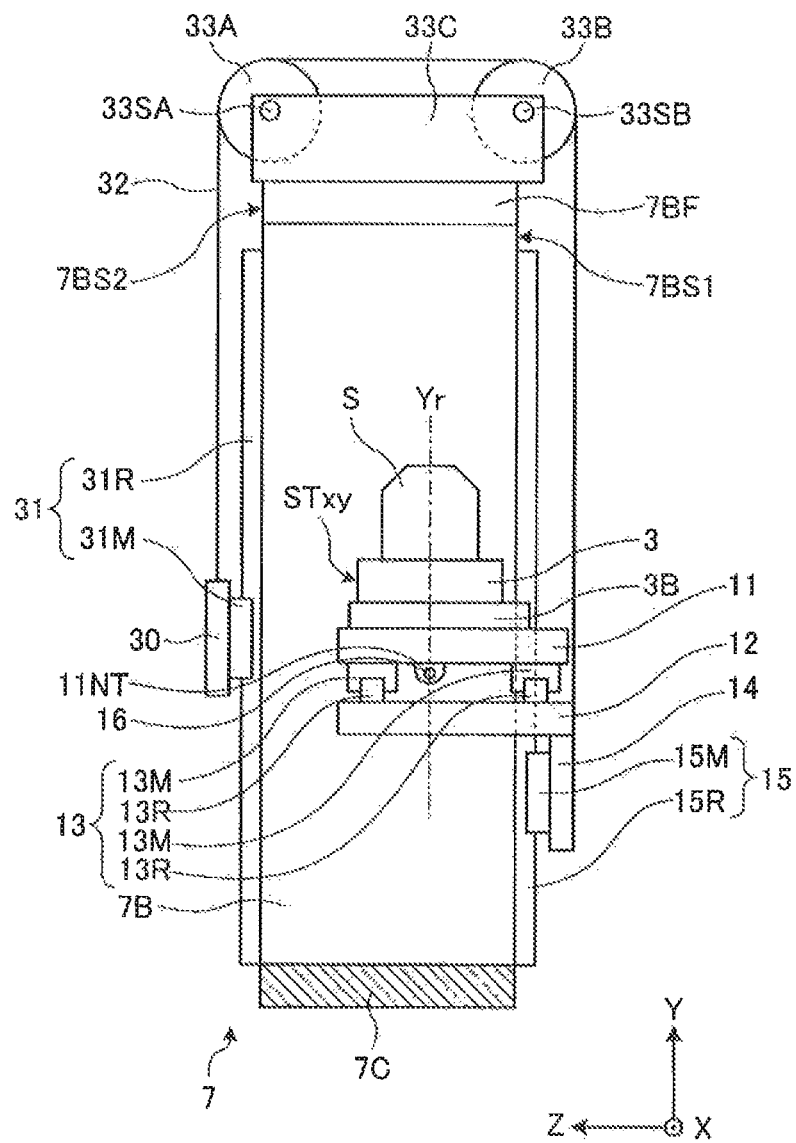
FIG. 10 is a diagram illustrating a structure for moving in a direction of a table rotation axis.

FIGS. 9 and 10 are diagrams illustrating a structure for moving in a direction of the table rotation axis. As described earlier, in the present embodiment, the table 3 and the table main body 3B are supported by the table support body 7 using the first mobile member 11, the base 12, and the second mobile member 14. The second mobile member 14 is supported by the side portion 7AS1 of the first member 7A and the side portion 7BS1 of the second member 7B of the table support body 7, using the guide mechanisms 15; accordingly, the table 3 moves along the first member 7A and the second member 7B.

The table 3 includes the table main body 3B, the first mobile member 11, a nut 11NT attached to the first mobile member 11 and into which the screw shaft 16 is screwed, the base 12, the rails 13R, and movement members 13M, and moves in the Y-axis direction along the first member 7A and the second member 7B along with an XY movement mechanism STxy that includes two guide mechanisms 13, the second mobile member 14, and the like attached to the base 12. In the present embodiment, the table support body 7 includes a counterweight 30 in order to reduce the burden on the actuator 21 that moves those elements. The counterweight 30 is disposed on the side portion 7AS2 and 7BS2 side of the first member 7A and the second member 7B, which is the side opposite from the side portions 7AS1 and 7BS1.

The counterweight 30 is attached to the first member 7A and the second member 7B by guide mechanisms 31 and 31 that are attached to the side portions 7AS2 and 7BS2 of the first member 7A and the second member 7B, respectively. Rails 31R and 31R serving as guide members provided in the guide mechanisms 31 are attached to the side portion 7AS2 of the first member 7A and the side portion 7BS2 of the second member 7B, respectively. The rails 31R and 31R extend in the direction in which the first member 7A and the second member 7B extend, or in other words, extend from the first flange portion 7AF and the second flange portion 7BF toward the third member 7C along the first member 7A and the second member 7B. Mobile members 31M and 31M integrated with and guided by the rails 31R and 31R are attached to the counterweight 30. According to this structure, the counterweight 30 is guided by the guide mechanisms 31 and 31 and moves along the first member 7A and the second member 7B.

The XY movement mechanism STxy and the counterweight 30 are connected by a suspension wire 32. As illustrated in FIG. 10, the suspension wire 32 passes along the second flange portion 7BF side of the second member 7B and connects the XY movement mechanism STxy and the counterweight 30. Two pulleys 33A and 33B and a pulley support body 33C that supports the pulleys are attached to the second flange portion 7BF of the second member 7B. The pulleys 33A and 33B are attached to the pulley support body 33C by shafts 33SA and 33SB, respectively. The suspension wire 32 that connects the XY movement mechanism STxy and the counterweight 30 is stretched upon the pulleys 33A and 33B.

The mass of the counterweight 30 and the mass of the XY movement mechanism STxy are substantially equal. Accordingly, the XY movement mechanism STxy and the counterweight 30, which are respectively disposed on the side portion 7AS1 and 7BS1 side and the side portion 7AS2 and 7BS2 side of the first member 7A and the second member 7B and are connected by the suspension wire 32, have balanced masses. As such, when moving the XY movement mechanism STxy in the Y-axis direction, that mechanism can be moved with a small amount of force. As a result, the power for moving the XY movement mechanism STxy is reduced, which reduces the burden on the actuator 21 illustrated in FIG. 6. Furthermore, because only a small amount of power is needed to move the XY movement mechanism STxy, a small, low-output actuator can be used as the actuator 21.

Figure 11:
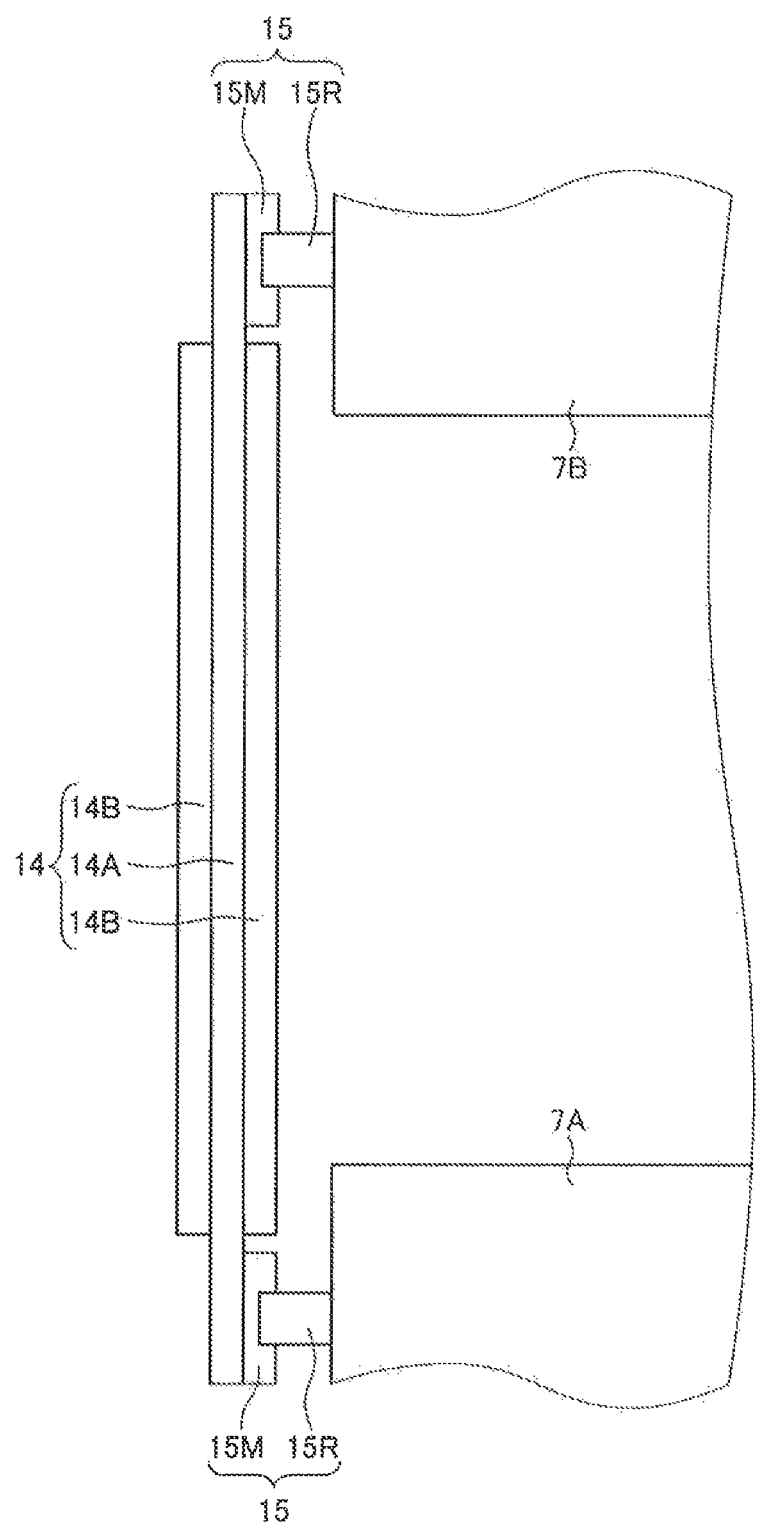
FIG. 11 is a diagram illustrating a second mobile member that supports a table.

FIG. 11 is a diagram illustrating the second mobile member that supports the table. The second mobile member 14 that supports the table 3 is a plate-shaped member that moves along the first member 7A and the second member 7B of the table support body 7. The second mobile member 14 includes a first plate-shaped member 14A and second plate-shaped members 14B and 14B. The movement members 15M and 15M of the guide mechanisms 15 and 15 are attached to the first plate-shaped member 14A. The rails 15R and 15R of the guide mechanisms 15 and 15 are attached to the first member 7A and the second member 7B, respectively. In other words, the first plate-shaped member 14A is attached to the first member 7A and the second member 7B by the guide mechanisms 15 and 15. The first plate-shaped member 14A moves along the first member 7A and the second member 7B by the guide mechanisms 15 and 15.

In the present embodiment, the first plate-shaped member 14A is manufactured from a material having a low coefficient of linear expansion (invariable steel, in the present embodiment), in the same manner as the support body 6 and the table support body 7. Such a material is expensive, as mentioned earlier. As such, in the present embodiment, a second plate-shaped member 14B that is manufactured from a different material from the first plate-shaped member 14A is combined with the first plate-shaped member 14A and the combination is used as the second mobile member 14 in order to reduce the amount of material having a low coefficient of linear expansion that is used. Specifically, a pair, or in other words, two second plate-shaped members 14B and 14B are attached to either side of the first plate-shaped member 14A. Accordingly, the pair of second plate-shaped members 14B and 14B sandwich the first plate-shaped member 14A from both sides thereof.

By doing so, the required strength and rigidity is ensured for the second mobile member 14 while keeping the first plate-shaped member 14A thin. In the present embodiment, the second plate-shaped members 14B and 14B are manufactured from a steel material such as carbon steel, or stainless steel. Such a steel material is cheaper than a nickel-based alloy, which is the material of the first plate-shaped member 14A. Such a steel material also has high strength and rigidity. Accordingly, by using a steel material such as carbon steel, or stainless steel for the second plate-shaped members 14B and 14B, it is easy to ensure the required strength and rigidity for the second mobile member 14 even if the thickness of the second plate-shaped members 14B and 14B is reduced. As a result, an increase in the mass of the second mobile member 14 can be suppressed, and the required strength and rigidity for the second mobile member 14 can be ensured. The cost of manufacturing the second mobile member 14 can also be suppressed.

The material of the second plate-shaped members 14B and 14B has a different coefficient of linear expansion from the material of the first plate-shaped member 14A. Specifically, the material of the second plate-shaped members 14B and 14B has a higher coefficient of linear expansion than the material of the first plate-shaped member 14A. In the present embodiment, a second plate-shaped member 14B may be attached to one surface of the first plate-shaped member 14A. However, because there is a difference between the coefficients of linear expansion of the first plate-shaped member 14A and the second plate-shaped member 14B, the second mobile member 14 may warp due to changes in temperature if the second plate-shaped member 14B, whose coefficient of linear expansion is higher than the first plate-shaped member 14A, is attached to one surface of the first plate-shaped member 14A. Accordingly, in the present embodiment, the second plate-shaped members 14B and 14B are attached to both sides of the first plate-shaped member 14A. According to this structure, warping (deformation) in the second mobile member 14 caused by changes in temperature is suppressed, and positional skew in the table 3 and the subject S supported thereon is suppressed.

It is preferable that the pair of second plate-shaped members 14B and 14B be manufactured from the same material. It is further preferable that the pair of second plate-shaped members 14B and 14B have the same shape and dimensions. By doing so, expansion/contraction of the second plate-shaped members 14B and 14B caused by changes in temperature can be kept substantially equal on both sides of the first plate-shaped member 14A, which makes it possible to further suppress warping (deformation) in the second mobile member 14.

Figure 12:
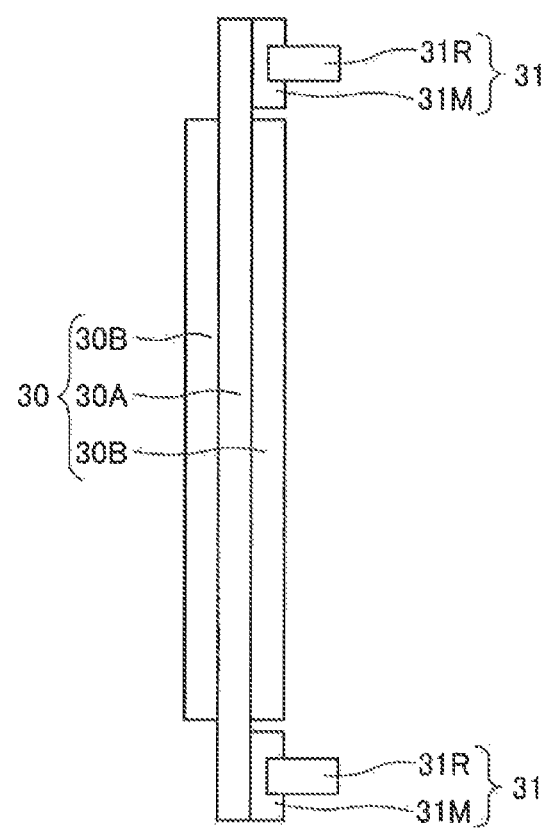
FIG. 12 is a diagram illustrating a counterweight.

FIG. 12 is a diagram illustrating the counterweight. The counterweight 30 is a structure in which both sides of a first plate-shaped member 30A are sandwiched between a pair, or in other words, two second plate-shaped members 30B. The movement members 31M that are guided by the rail 31R of the guide mechanism 31 are attached to the first plate-shaped member 30A. Accordingly, deformation of the first plate-shaped member 30A caused by changes in temperature is kept to a minimum, and thus the first plate-shaped member 30A is manufactured from a material having a low coefficient of linear expansion (invariable steel, in the present embodiment).

As mentioned earlier, the material having a low coefficient of linear expansion is expensive, and thus manufacturing the counterweight 30 entirely from a material having a low coefficient of linear expansion increases the manufacturing cost of the counterweight 30. Accordingly, the second plate-shaped members 30B, which are manufactured from a cheaper material than the first plate-shaped member 30A, are attached to the first plate-shaped member 30A. At this time, sandwiching the first plate-shaped member 30A between the pair of second plate-shaped members 30B and 30B, which are manufactured from the same material, makes it possible to ensure the same deformation in the second plate-shaped members 30B on both sides of the first plate-shaped member 30A. As a result, warping (deformation) in the counterweight 30 caused by changes in temperature can be suppressed while ensuring the counterweight 30 fulfills its function.

The manufacturing cost of the counterweight 30 can also be suppressed. It is further preferable that the pair of second plate-shaped members 30B and 30B have the same shape and dimensions. By doing so, expansion/contraction of the second plate-shaped members 30B and 30B caused by changes in temperature can be kept equal on both sides of the first plate-shaped member 30A, which makes it possible to further suppress warping (deformation) in the counterweight 30.

Figure 13:
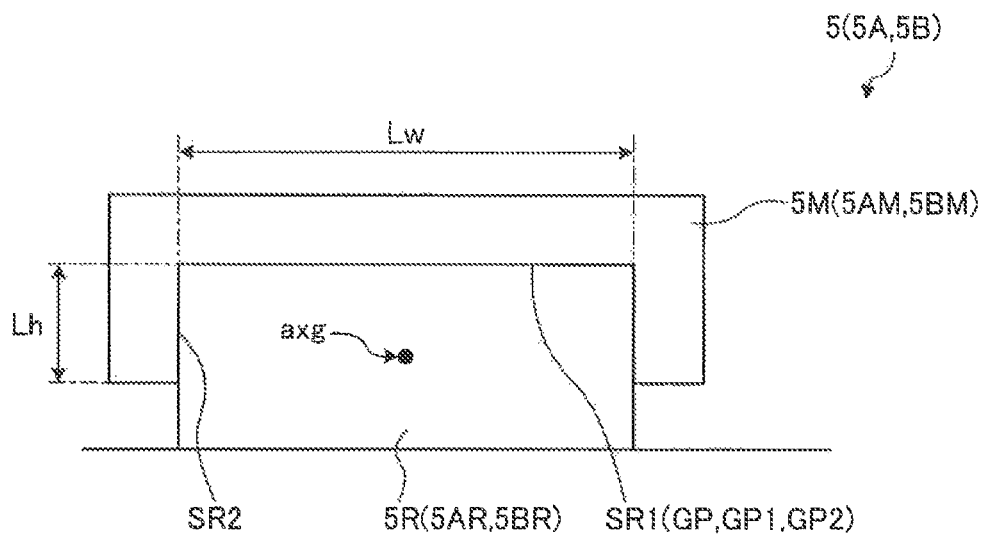
FIG. 13 is a diagram illustrating a guide plane of a guide device.
Figure 14:
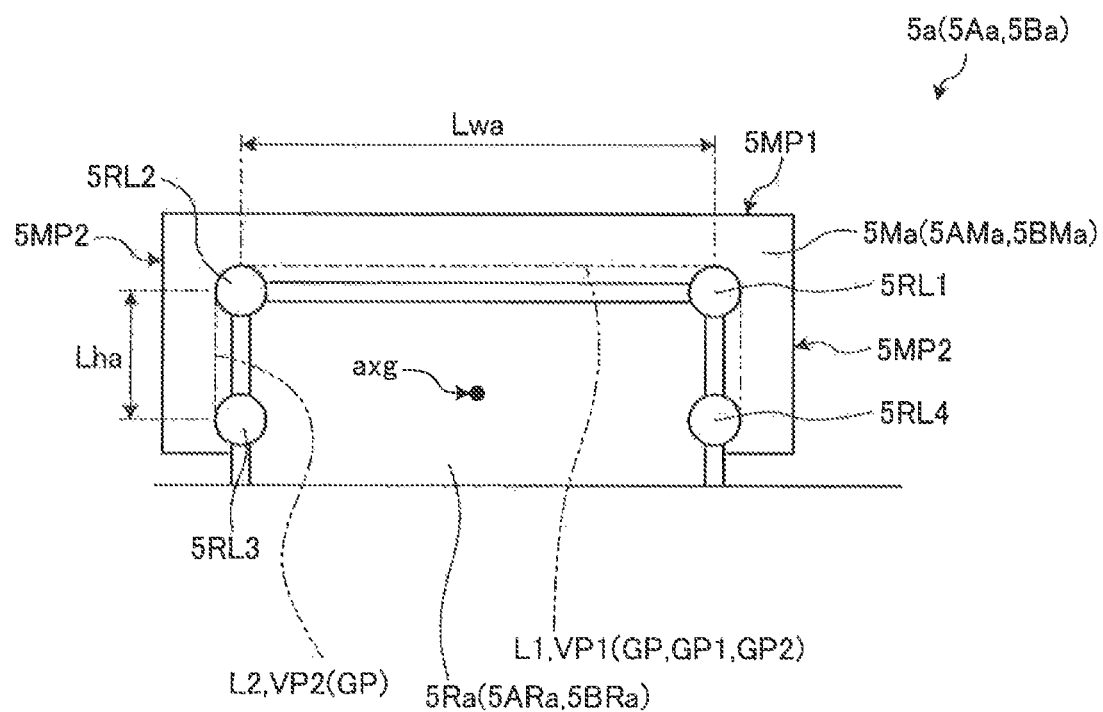
FIG. 14 is a diagram illustrating a guide plane of a guide device.
Figure 15:
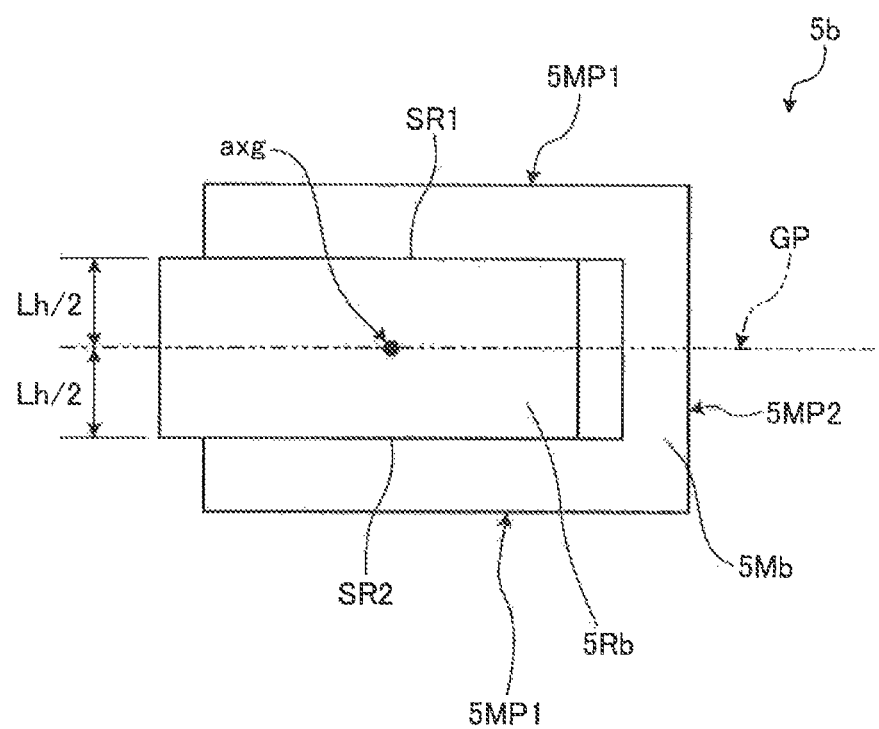
FIG. 15 is a diagram illustrating a guide plane of a guide device.

FIGS. 13, 14, and 15 are diagrams illustrating the guide plane of the guide device. FIGS. 13 and 14 are cross-sections obtained by cutting along a plane orthogonal to a movement direction of movement members 5M and 5Ma, or in other words, orthogonal to a direction in which rails 5R and 5Ra extend (called horizontal cross-sections as appropriate hereinafter). In the present embodiment, the guide device 5 that guides the movement in the optical axis Zr direction of the table 3 supported by the table support body 7 illustrated in FIGS. 6, 7, 8, and so on, or in other words, the first guide device 5A and the second guide device 5B, as illustrated in FIGS. 6 and 13, each has a first guide plane GP1 and a second guide plane GP2. The first guide plane GP1 and the second guide plane GP2 are planes that regulate the movement of the movement members 5AM and 5BM. In the case where both the first guide device 5A and the second guide device 5B guide the movement of the table 3 by the table support body 7 as illustrated in FIGS. 6, 7, and the like, the first guide plane GP1 and the second guide plane GP2 serve as planes that regulate the movement of the table 3 (the same applied hereinafter).

In the guide device 5 illustrated in FIG. 13, or in other words, the first guide device 5A and the second guide device 5b, the rails 5R (5AR and 5BR) and the movement members 5M (5AM and 5BM) make contact with each other. The guide device 5 has two contact surfaces, namely a contact surface SR1 and a contact surface SR2, between the movement members 5M and the rails 5R. The contact surface SR1 has a greater contact surface area with the movement members 5M and the rails 5R than the contact surface SR2. Accordingly, a contact length Lw of the contact surface SR1 in the horizontal cross-section is greater than a contact length Lh of the contact surface SR2 (Lw>Lh). Consider a case where the movement members 5M tilt central to an axis axg parallel to the movement direction of the movement members 5M, or in other words, parallel to the direction in which the rails 5R extend (called a guide axis as appropriate hereinafter). The effect of suppressing this tilt is greater for the contact surface SR1, whose contact length Lw in the horizontal cross-section is greater than the contact length Lh of the contact surface SR2, than for the contact surface SR2. In the present embodiment, the guide device 5, the guide planes GP of the first guide device 5A and the second guide device 5B, and the first guide plane GP1 and the second guide plane GP2 refer to the contact surface SR1, which has a greater effect of suppressing tilt of the movement members 5M, 5AM, and 5BM central to the guide axis axg. A guide device 5a illustrated in FIG. 14, or in other words, a first guide device 5Aa and a second guide device 5Ba, have rolling members (balls, in the present example) 5RL1, 5RL2, 5RL3, and 5RL4 interposed between rails 5Ra (SARa and SBRa) and movement members 5Ma (SAMa and SBMa). The movement members 5Ma are guided by the rails 5Ra using the rolling members 5RL1, 5RL2, 5RL3, and 5RL4. The rails 5Ra are rectangular in shape when viewed in the horizontal cross-section.

The rolling member 5RL1 and the rolling member 5RL2 are provided adjacent to each other on the long side of the rails 5Ra, when viewed as the horizontal cross-section. Meanwhile, the rolling member 5RL2 and the rolling member 5RL3 are provided adjacent to each other, and the rolling member 5RL1 and the rolling member 5RL4 are provided adjacent to each other, on the short side of the rails 5Ra when viewed as the horizontal cross-section. Consider, in the horizontal cross-section, a line segment L1 that connects an area that is a contact area between the rolling member 5RL1 and the movement member 5Ma, and is closest to the broader surface (called a first surface as appropriate hereinafter) 5MP1 of the movement member 5Ma, with an area that is a contact area between the rolling member 5RL2 and the movement member 5Ma, and is closest to the first surface 5MP1. A plane formed by extending this line segment L1 parallel to the guide axis axg will be called a plane VP1.

Next, consider, in the horizontal cross-section, a line segment L2 that connects an area that is a contact area between the rolling member 5RL2 (or the rolling member 5RL1) and the movement member 5Ma, and is closest to the narrower surface (called a second surface as appropriate hereinafter) 5MP2 of the movement member 5Ma, with an area that is a contact area between the rolling member 5RL3 (or the rolling member 5RL4) and the movement member 5Ma, and is closest to the second surface 5MP2. A plane formed by extending this line segment L2 parallel to the guide axis axg will be called a plane VP2.

The plane VP1 and the plane VP2 are planes in which the rails 5Ra regulate the movement of the movement members 5Ma. In an area where the movement members 5Ma overlap with the rails 5Ra, the plane VP1 has a greater surface area than the plane VP2. Accordingly, the length of the plane VP1 in the horizontal cross-section, or in other words, a length Lwa of the line segment L1, is greater than the length of the plane VP2 in the horizontal cross-section, or in other words, a length Lha of the line segment L2 (Lwa>Lha).

Consider a case where the movement member 5Ma tilts central to the guide axis axg of the guide device 5a. The effect of suppressing this tilt is greater for the plane VP1, whose contact length Lwa in the horizontal cross-section is greater than the contact length Lha of the plane VP2, than for the plane VP2. In the present embodiment, the guide device 5a, the guide planes GP of the first guide device 5Aa and the second guide device 5Ba, and the first guide plane GP1 and the second guide plane GP2 refer to the plane VP1, which has a greater effect of suppressing tilt of the movement member 5Ma central to the guide axis axg.

The guide device 5b illustrated in FIG. 15 has the two contact surfaces SR1 and SR2 disposed parallel to and opposing each other. The contact surfaces SR1 and SR2 are surfaces that make contact with the rail 5Rb and the movement member 5Mb. The first surface 5MP1, which is the broader surface of the movement member 5Mb, is the surface on the contact surface SR1 and SR2 side. The second surface 5MP2, which is the narrower surface of the movement member 5Mb, is a surface that makes contact with the pair of first surfaces 5MP1 and 5MP1. In the guide device 5b, a structure is attached to the second surface 5MP2. In the case of the guide device 5b having the two contact surfaces SR1 and SR2, a plane that is parallel to the two contact surfaces SR1 and SR2 and present in a position equally distant from the respective contact surfaces SR1 and SR2 is the guide plane GP. The distance from each of the contact surfaces SR1 and SR2 to the guide plane GP is Lh/2. The guide plane GP also passes through the guide axis axg.

In the present embodiment, the guide plane GP passes through the detection region DR in a direction orthogonal to the support surface 3P of the table 3 on which the subject S is supported, as illustrated in FIG. 6. When the detection device 1 is installed, the support surface 3P of the table 3 is orthogonal to the vertical direction, or in other words, to direction in which gravity acts. As such, when the relationship between the guide plane GP and the detection region DR is set as mentioned earlier, the direction of a load such as the table 3, the table support body 7, and the like is orthogonal to the guide plane GP. Such being the case, it is preferable that the first guide device 5A and the second guide device 5B receive the aforementioned load at an area where the rails 5AR and 5BR and the movement members 5AM and 5BM overlap over a greater surface area.

Figure 16:
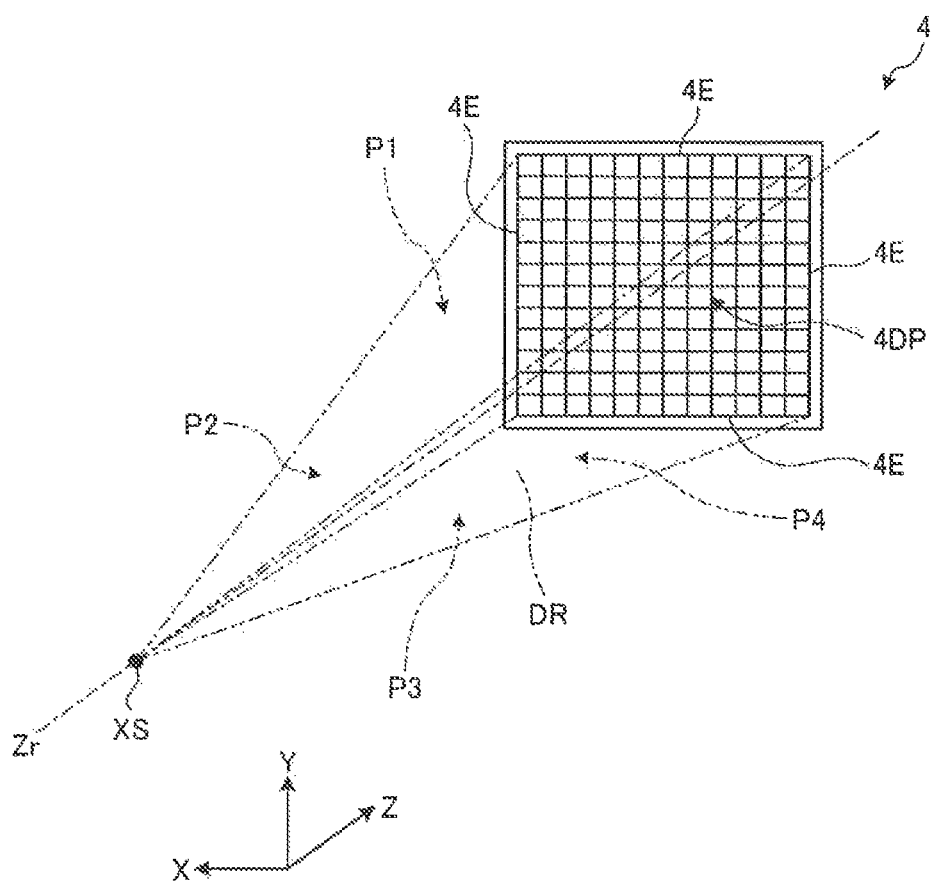
FIG. 16 is a diagram illustrating a detection region.
Figure 17:
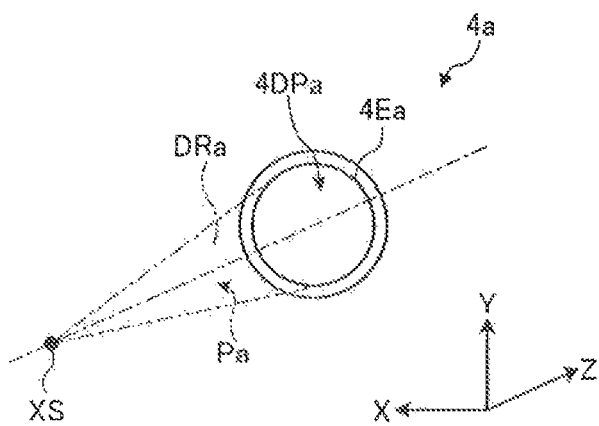
FIG. 17 is a diagram illustrating a detection region.

FIGS. 16 and 17 are diagrams illustrating the detection region. FIG. 16 illustrates the detection region DR in the case where the incidence surface 4DP of the detector 4 is rectangular (including a square). FIG. 17 illustrates the detection region DR in the case where an incidence surface 4DPa of a detector 4a is circular. In the case where the incidence surface 4DP of the detector 4 is rectangular, the detection region DR is a region surrounded by the incidence surface 4DP and planes P1, P2, P3, and P4 formed by connecting a light-emission region (focal point) XS of the X-ray source 2 illustrated in FIG. 1 and the like with outer edges 4E of the incidence surface 4DP at which the detector 4 receives the X-rays. In this case, the detection region DR has a quadrangular cone shape with the incidence surface 4DP serving as the base plane and the light-emission region XS serving as the apex.

In the case where, as illustrated in FIG. 17, the incidence surface 4DPa of the detector 4a is circular, the detection region DRa is a region surrounded by the incidence surface 4DPa and a plane Pa formed by connecting the light-emission region XS of the X-ray source 2 illustrated in FIG. 1 and the like with an outer edge 4Ea of the incidence surface 4DPa at which the detector 4 receives the X-rays. In this case, the detection region DRa has a circular cone shape with the incidence surface 4DPa serving as the base plane and the light-emission region XS serving as the apex. The incidence surface 4DP may be a polygon aside from a rectangle, such as a triangle, a hexagon, or the like, and the incidence surface 4DPa may has an elliptical shape or the like instead of being circular.

Figure 18:
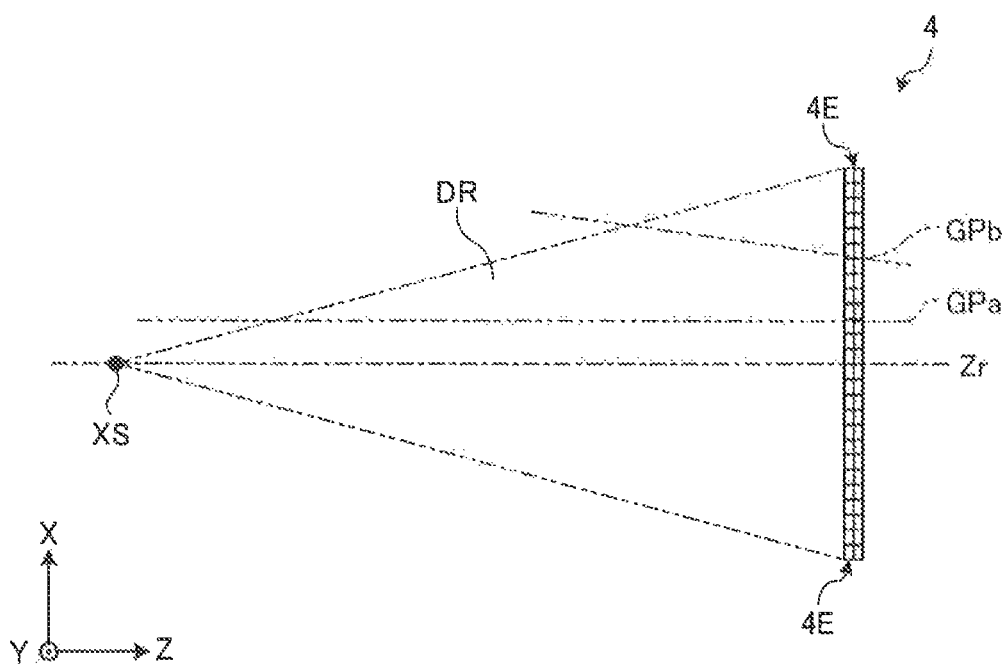
FIG. 18 is a diagram illustrating a relationship between a detection region and a guide plane.

FIG. 18 is a diagram illustrating a relationship between the detection region and the guide plane. In the present embodiment, as illustrated in FIG. 6, the first guide device 5A and the second guide device 5B are disposed with the optical axis Zr located therebetween, and the substantially U-shaped table support body 7 is supported by the support body 6. In this case, the guide plane GP is a plane that passes through at least part of the first guide plane GP1 of the first guide device 5A and at least part of the second guide plane GP2 of the second guide device 5B. In the detection device 1 illustrated in FIG. 6, the first guide plane GP1 and the second guide plane GP2 are in the same position in the table rotation axis Yr direction or the Y-axis direction. In this case, the guide plane GP is a plane that is parallel to and includes the first guide plane GP1 of the first guide device 5A and the second guide plane GP2 of the second guide device 5B. In other words, the guide plane GP is a plane that passes through the entirety of the first guide plane GP1 and the second guide plane GP2. The first guide plane GP1 and the second guide plane GP2 are as described using FIGS. 13 and 14.

In the detection device 1 illustrated in FIG. 6, the guide plane GP (or a plane that includes the guide plane GP and is parallel to the guide plane GP) passes through the detection region DR for the transmitted X-rays in the detector 4, and furthermore contains the optical axis Zr and is parallel to the optical axis Zr. It is sufficient for the guide plane GP to pass through the detection region DR. As long as this condition is met, the optical axis Zr need not be contained, as with a guide plane GPa illustrated in FIG. 18, or the guide plane GP need not be parallel to the optical axis Zr, as with a guide plane GPb.

Figure 19:
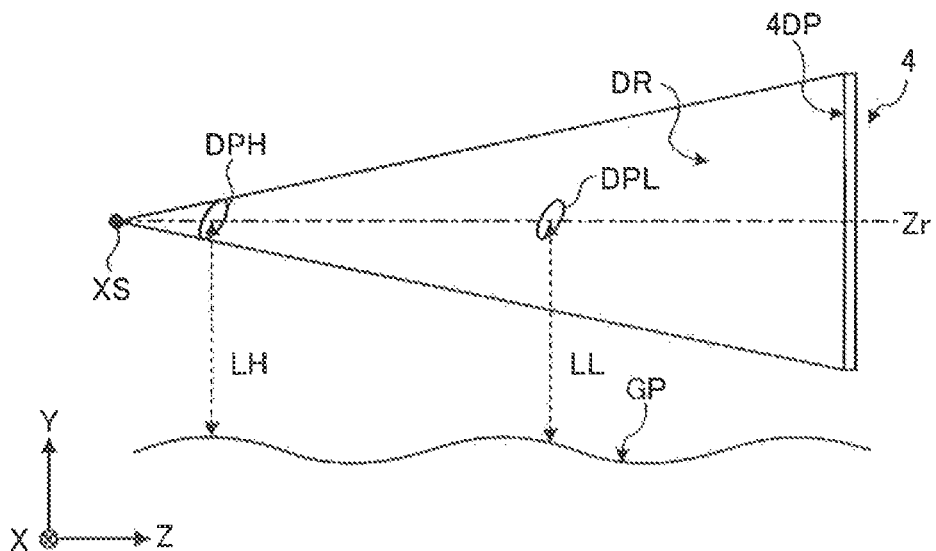
FIG. 19 is a diagram illustrating a relationship between a detection region and a guide plane according to a comparative example.
Figure 20:
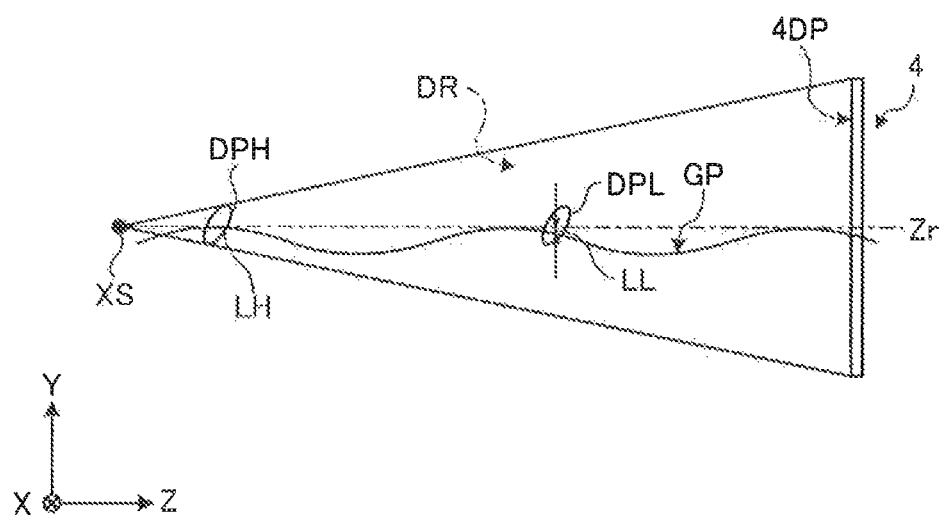
FIG. 20 is a diagram illustrating a relationship between a detection region and a guide plane according to an embodiment.

FIG. 19 is a diagram illustrating a relationship between a detection region and a guide plane according to a comparative example. FIG. 20 is a diagram illustrating a relationship between the detection region and the guide plane according to the present embodiment. Reference numerals DPH and DPL in FIGS. 19 and 20 indicate detection centers of the incidence surface 4DP of the detector 4. In this example, the detection centers DPH and DPL are present on the optical axis Zr. A distance (minimum distance) from the guide plane GP to the detection center DPH is represented by LH, and a distance (minimum distance) from the guide plane GP to the detection center DPL is represented by LL.

In the comparative example, the guide plane GP is located outside of the detection region DR, and the two do not intersect. In the present embodiment, the guide plane GP passes through the detection region DR. Furthermore, in the present embodiment, the guide plane GP contains the optical axis Zr and is positioned so as to be parallel to the optical axis Zr. FIGS. 18 and 19 illustrate the guide plane GP in an enlarged manner. The guide plane GP is defined by the movement member 5AM and 5BM-side surfaces of the rails 5AR and 5BR in the first guide device 5A and the second guide device 5B. The surfaces of the rails 5AR and 5BR may have dimensions and shapes that deviate from the design values thereof due to processing error or the like. As such, the guide plane GP defined by the surfaces of the rails 5AR and 5BR is a flat plane at the macro level, but is not a flat plane at the micro level. Accordingly, the Y-axis direction position of the guide plane GP varies along the Z-axis direction at the micro level, as indicated in FIGS. 19 and 20.

The guide plane GP is a plane that regulates the movement of the movement members 5AM and 5BM, the table support body 7 attached thereto, and the table 3 supported by the table support body 7. If the Y-axis direction position of the guide plane GP varies along the Z-axis direction, the support surface 3P of the table 3, indicated in FIG. 6 and whose movement is defined by the guide plane GP, will tilt central to the X-axis, or in other words, will slant relative to the XZ plane. As a result, the subject S supported by the support surface 3P of the table 3 will also tilt central to the X-axis. The detection centers DPH and DPL pass through the subject S supported on the support surface 3P or the table 3. Accordingly, if the subject S tilts central to the X-axis, the position of the subject S will be skewed from the original position, which results in a drop in the detection accuracy of the detection device 1 illustrated in FIG. 6.

Based on the Abbe principle, positional skew of the subject S caused by slanting of the support surface 3P of the table 3 will increase as the distances LH and LL between the guide plane GP and the detection centers DPH and DPL increase. The distances LH and LL from the guide plane GP to the detection centers DPH and DPL are lower in the present embodiment than in the comparative example. Accordingly, the present embodiment can ensure less positional skew in the subject S caused by the Y-axis direction position of the guide plane GP varying along the Z-axis direction than the comparative example. As a result, the present embodiment can suppress a drop in the detection accuracy of the detection device 1.

In the present embodiment, the guide plane GP passes through the detection region DR. In this case, the guide plane GP may pass through positions where the encoder heads 24AE and 24BE of the linear encoders 24A and 24B read the linear scales 24AS and 24BS (called encoder reading positions hereinafter as appropriate). By doing so, error arising when the encoder heads 24AE and 24BE read the linear scales 24AS and 24BS, caused by the encoder reading positions being distant from the guide plane GP, can be reduced. Accordingly, the detection device 1 can suppress a drop in accuracy when the control device 9 controls the movement of the table support body 7 on the basis of the measurement results from the encoder heads 24AE and 24BE. As a result, the detection device 1 can suppress a drop in the detection accuracy.

Figure 21:
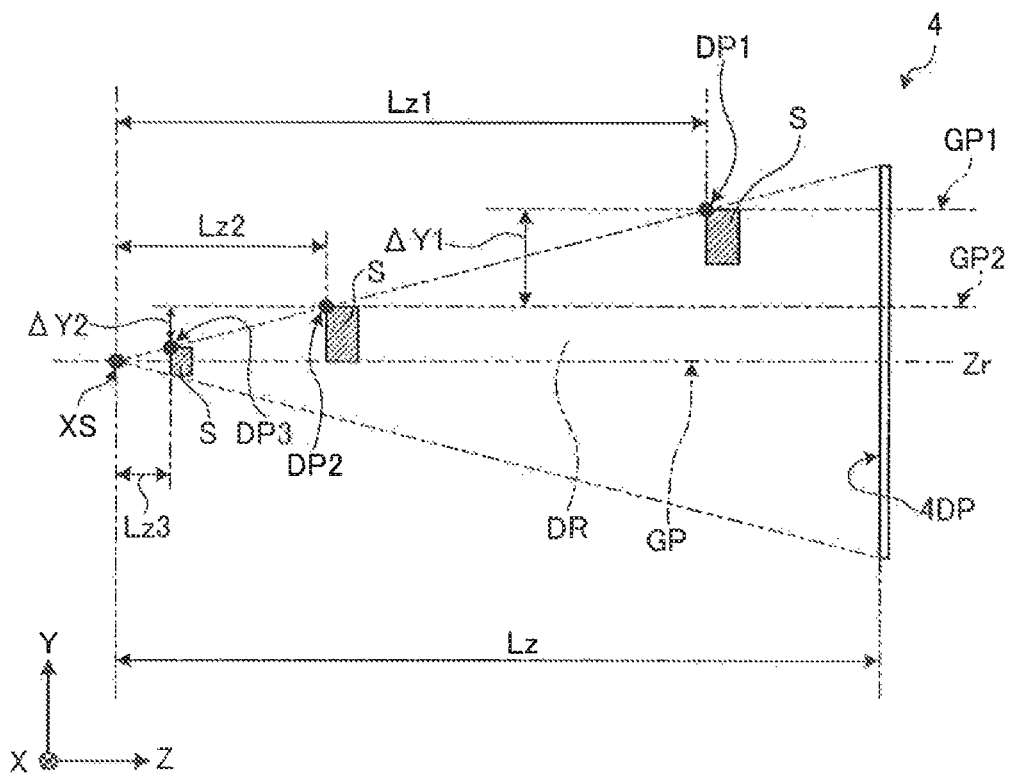
FIG. 21 is a diagram illustrating a relationship between a detection region and a guide plane according to an embodiment.

FIG. 21 is a diagram illustrating a relationship between the detection region and the guide plane according to the present embodiment. In the example illustrated in FIG. 21, a distance between the light-emission region XS of the X-ray source 2 and the incidence surface 4DP of the detector 4 in the optical axis Zr direction is indicated by Lz. In the present embodiment, it is sufficient for the guide plane GP to pass through the detection region DR. In the example illustrated in FIG. 20, the guide plane GP contains the optical axis Zr and is positioned parallel to the optical axis Zr, but it is not necessary for the guide plane GP to be positioned in this manner as long as the guide plane GP passes through the detection region DR. The guide planes GP1 and GP2 illustrated in FIG. 21 are parallel to the optical axis Zr but do not contain the optical axis Zr. This positioning is also possible because the guide planes GP1 and GP2 pass through the detection region DR.

The detector 4 cannot detect objects outside of the detection region DR. As such, in the case of the guide plane GP1, when detecting the subject S present in the range of a distance Lz1 from the light-emission region XS of the X-ray source 2, the detection center is in a position relatively far from the guide plane GP1. For example, in the case of the guide plane GP1, the subject S is present within the detection region DR when the detector 4 detects the subject S present at a position DP1 at a distance of Lz1 from the light-emission region XS. As such, because the distance from the guide plane GP1 to the measurement center can be set to 0, positional skew of the subject S caused by the Y-axis direction position of the guide plane GP1 varying along the Z-axis direction can be suppressed.

In the case of the guide plane GP1, it is necessary for the subject S to be present within the detection region DR when the detector 4 detects the subject S present at a position DP2 at a distance of Lz2 from the light-emission region XS. As such, because it is necessary for the distance from the guide plane GP1 to the measurement center to be at least $\Delta Y1$, positional skew of the subject S caused by the Y-axis direction position of the guide plane GP1 varying along the Z-axis direction may increase. In other words, in the case of the guide plane GP1, positional skew of the subject S can be effectively suppressed in a region from distances Lz-Lz1 from the incidence surface 4DP of the detector 4.

The guide plane GP2 is closer to the optical axis Zr than the guide plane GP1. For example, in the case of the guide plane GP2, the subject S is present within the detection region DR when the detector 4 detects the subject S present at the position DP2 at a distance of Lz2 (<Lz1) from the light-emission region XS. As such, because the distance from the guide plane GP2 to the measurement center can be set to 0, positional skew of the subject S caused by the Y-axis direction position of the guide plane GP2 varying along the Z-axis direction can be kept lower than in the case of the guide plane GP1.

In the case of the guide plane GP2, the subject S is present outside of the detection region DR when the detector 4 detects the subject S present at a position DP3 at a distance of Lz3 that is closer to the light-emission region XS than the distance Lz2. Accordingly, a distance of at least ΔY2 is necessary from the guide plane GP2 to the measurement center. As a result, it is possible that the positional skew in the subject S caused by the Y-axis direction position of the guide plane GP2 varying along the Z-axis direction will not be sufficiently suppressed. In other words, in the case of the guide plane GP2, positional skew of the subject S can be effectively suppressed in a region from distances Lz-Lz2 from the incidence surface 4DP of the detector 4.

By setting the guide plane GP to contain the optical axis Zr and to be parallel to the optical axis Zr, the distance from the guide plane GP to the measurement center can be set to 0 when the detector 4 detects the subject S present at the position DP3 at a distance of Lz3 from the light-emission region XS. As a result, positional skew in the subject S caused by the Y-axis direction position of the guide plane GP varying along the Z-axis direction can be kept lower than in the case of the guide plane GP2. In other words, in the case where the guide plane GP contains the optical axis Zr and is parallel to the optical axis Zr, positional skew of the subject S can be effectively suppressed in a region up to a distance Lz from the incidence surface 4DP of the detector 4, or in other words, theoretically within the entire detection region DR.

In this manner, by bringing the guide plane GP closer to the optical axis Zr, positional skew of the subject S can be effectively suppressed in a region relatively far from the incidence surface 4DP of the detector 4. The greater the distance from the incidence surface 4DP of the detector 4 is, the larger the image of the subject S based on the transmitted X-rays detected by the detector 4 will be. In other words, the detection device 1 can detect (measure) an image of the subject S at a high rate of magnification. Accordingly, bringing the guide plane GP closer to the optical axis Zr makes it possible for the detection device 1 to detect (measure) an image of the subject S from a low rate of magnification to a high rate of magnification, and is therefore preferable. In other words, it is preferable that the guide plane GP be in approximately the same position as the optical axis Zr or substantially in the same position as the optical axis Zr, and further preferable that the guide plane GP be in the same position as the optical axis Zr. Note that the guide plane GP may be arranged in the case where the detection region DR has an area that is broader by approximately 10%. An area, relative to the Y-axis, of approximately 5%, 10%, and 15% of the detection region DR, central to the optical axis Zr, may be taken as a region near the optical axis Zr. Meanwhile, the vicinity of the X-ray source 2 central to the optical axis Zr may be taken as an area of approximately 5%, relative to the Y-axis, and the vicinity of the incidence surface 4DP may be taken as an area of approximately 15%. In other words, the area of a range in the vicinity along the Z-axis direction may be varied.

Figure 22:
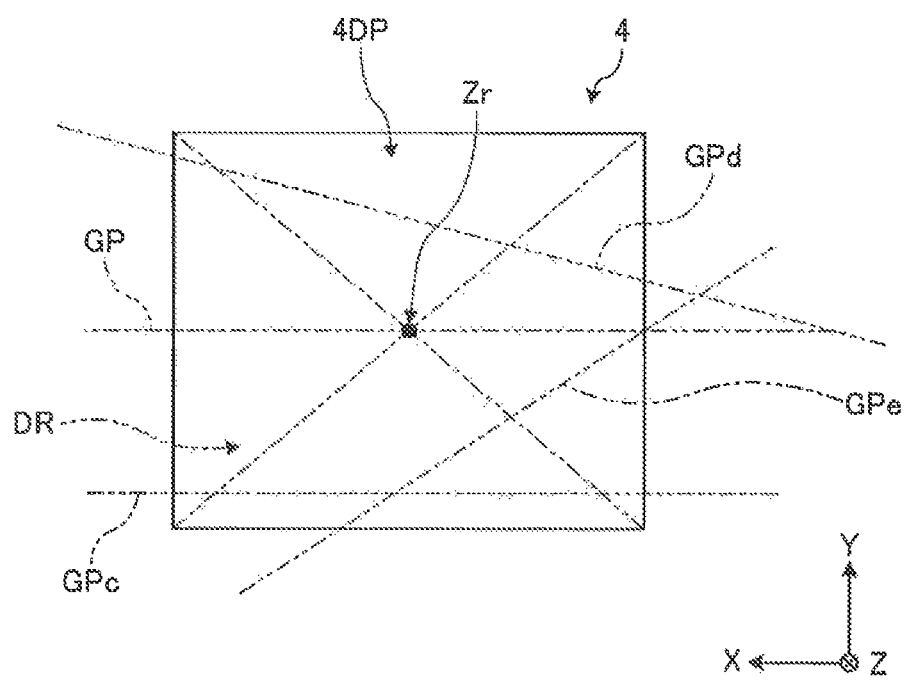
FIG. 22 is a diagram illustrating a variation on a relationship between a detection region and a guide plane according to an embodiment.

FIG. 22 is a diagram illustrating a variation on the relationship between the detection region and the guide plane according to the present embodiment. In FIG. 22, a plurality of guide planes GP, GPc, GPd, and GPe that pass through the detection region DR are illustrated. The guide plane GP contains the optical axis Zr and is parallel to the optical axis Zr. The guide plane GPc is parallel to the optical axis Zr and the X-axis but does not contain the optical axis Zr. The guide planes GPd and GPe are parallel to the optical axis Zr, but do not contain the optical axis Zr, and furthermore intersect with the X-axis. The guide planes GPd and GPe transect the incidence surface 4DP of the detector 4 diagonally. In this manner, as long as the guide planes GP, GPc, GPd, and GPe pass through the detection region DR, positional skew of the subject S caused by the Y-axis direction position of the guide planes GP, GPc, GPd, and GPe varying along the Z-axis direction can be effectively suppressed.

Figure 23:
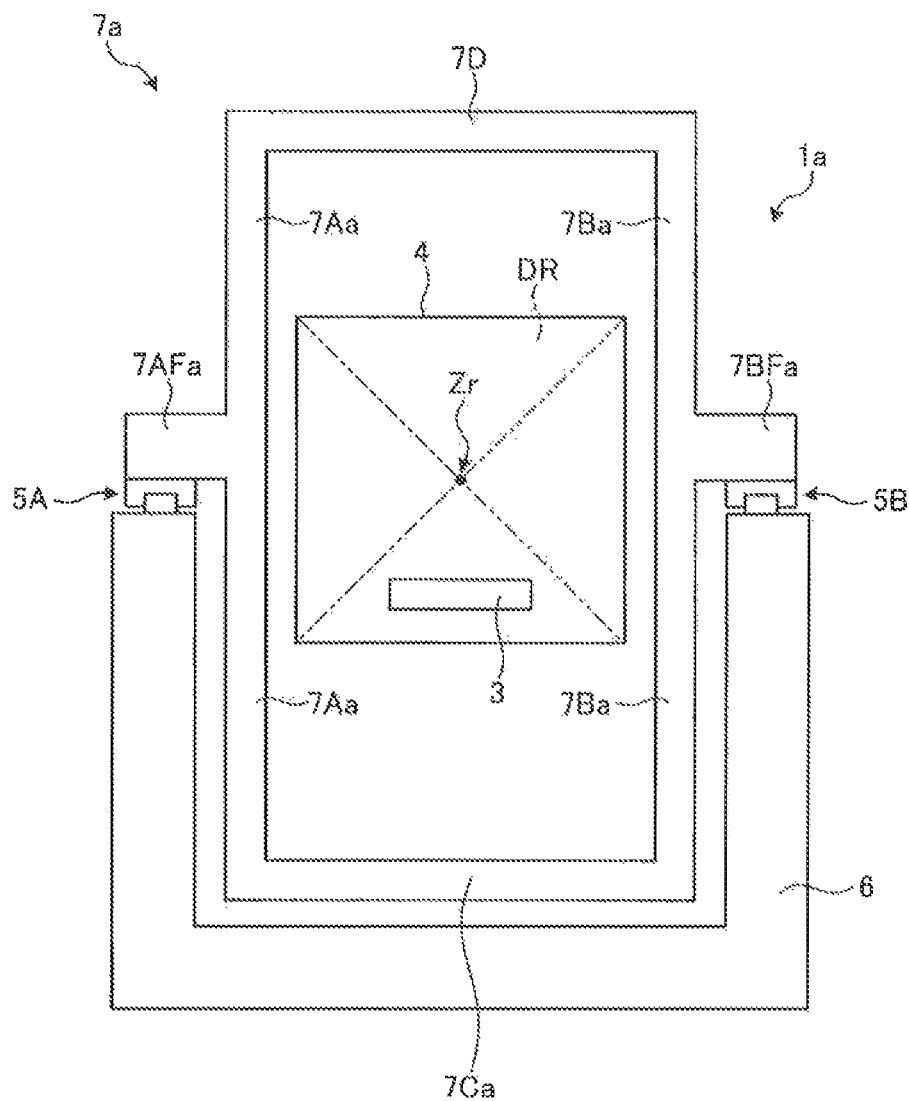
FIG. 23 is a diagram illustrating a variation on a table support body.

FIG. 23 is a diagram illustrating a variation on the table support body. This table support body 7a has a structure in which corresponding end portions of a first member 7Aa and a second member 7Ba are connected by a third member 7Ca and a fourth member 7D, respectively. In the table support body 7a, the table 3 and the detection region DR of the detector 4 are disposed within an area surrounded by the first member 7Aa, the second member 7Ba, the third member 7Ca, and the fourth member 7D. The first member 7Aa has, between both end portions thereof, a first flange portion 7AFa that extends outward. The second member 7Ba has, between both end portions thereof, a second flange portion 7BFa that extends outward. The first guide device 5A is attached to the first flange portion 7AFa, and the second guide device 5B is attached to the second flange portion 7BFa. The table support body 7a is attached to the support body 6 by the first guide device 5A and the second guide device 5B. Like the table support body 7 according to the aforementioned embodiment, in the table support body 7a according to this variation, the table 3, the table main body 3B, the first mobile member 11, the base 12, and the second mobile member 14 are attached to the first member 7Aa and the second member 7Ba by the two guide mechanisms 15 and 15.

This table support body 7a is a substantially O-shaped structure in which the first member 7Aa and the second member 7Ba are connected by the third member 7Ca and the fourth member 7D, respectively. The table support body 7 according to the aforementioned embodiment is a substantially U-shaped structure in which the first member 7A and the second member 7B are connected by the third member 7C. Due to this structural difference, the table support body 7a has an advantage of being more rigid than the table support body 7 according to the aforementioned embodiment. As a result, the table support body 7a can more effectively suppress deformation due to the loads of the table 3, the subject S, and the like, which improves the positioning accuracy of the table 3. A detection device 1c that includes the table support body 7a has improved detection accuracy.

Figure 24:
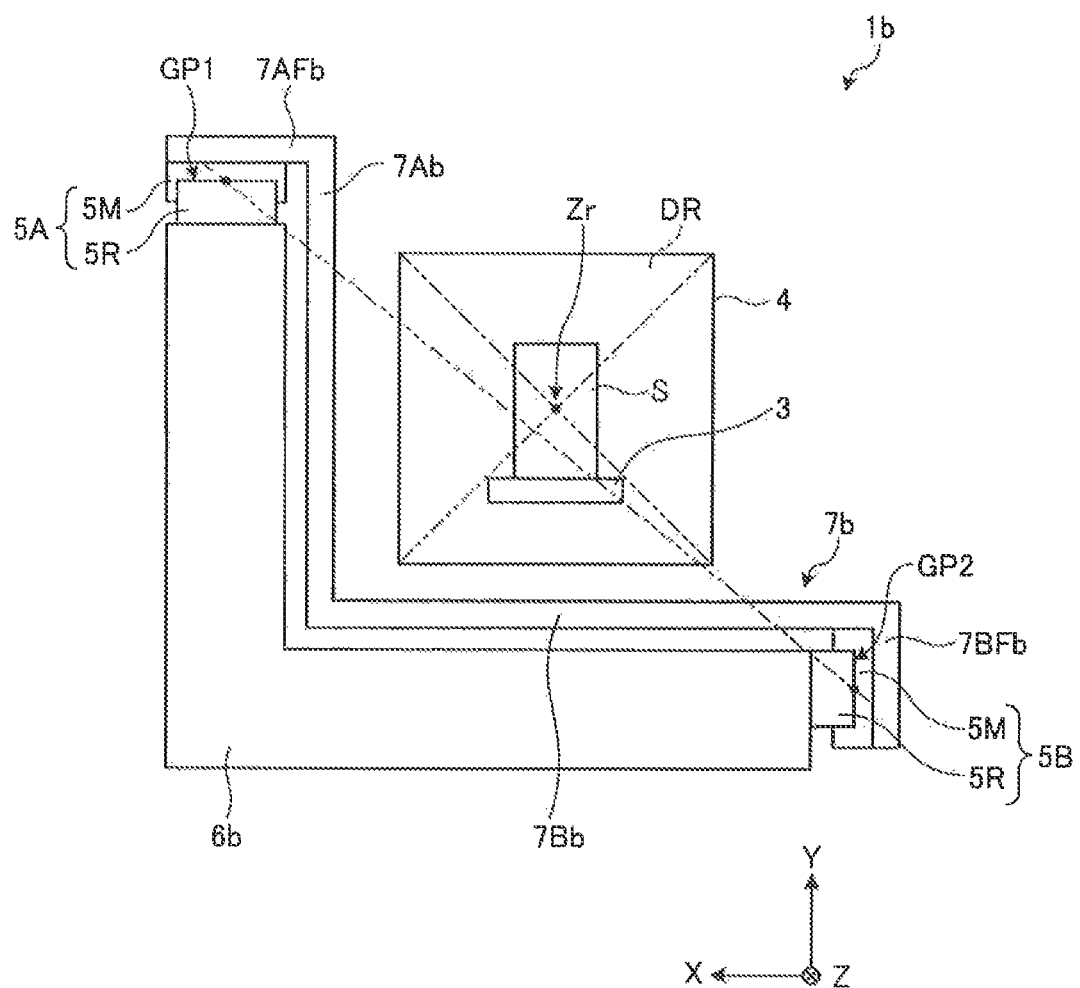
FIG. 24 is a diagram illustrating a variation on a table support body.

FIG. 24 is a diagram illustrating a variation on the table support body. This table support body 7b is a substantially L-shaped structure in which one end portion of a first member 7Ab is connected to one end portion of a second member 7Bb so that the first member 7Ab and the second member 7Bb are substantially orthogonal to each other. A first flange portion 7AFb is provided on another end of the first member 7Ab. A second flange portion 7BFb is provided on another end of the second member 7Bb. The first guide device 5A is attached to the first flange portion 7AFb, and the second guide device 5B is attached to the second flange portion 7BFb. The table support body 7b is attached to the support body 6 by the first guide device 5A and the second guide device 5B. The table 3 and the detection region DR of the detector 4 are disposed between the first member 7Ab and the second member 7Bb.

This table support body 7b is attached to the support body 6b by the two guide devices 5A and 5B. The first guide plane GP1 of the first guide device 5A attached to the first flange portion 7AFb and the second guide plane GP2 of the second guide device 5B attached to the second flange portion 7BFb are orthogonal to each other. According to the two guide devices 5A and 5B disposed in this manner, the guide plane GP is a plane that passes through the first guide plane GP1 and the second guide plane GP2 and is orthogonal to those two planes. In other words, the guide plane GP according to the present variation is a plane that passes through part of the first guide plane GP1 and part of the second guide plane GP2.

As illustrated in FIG. 24, the guide plane GP passes through the detection region DR of the detector 4. Accordingly, a detection device 1b that includes the table support body 7b can reduce positional skew in the subject S caused by the position of the guide plane GP in a direction orthogonal to the guide plane GP varying along the Z-axis direction. As a result, the detection device 1b can suppress a drop in the detection accuracy.

Figure 25:
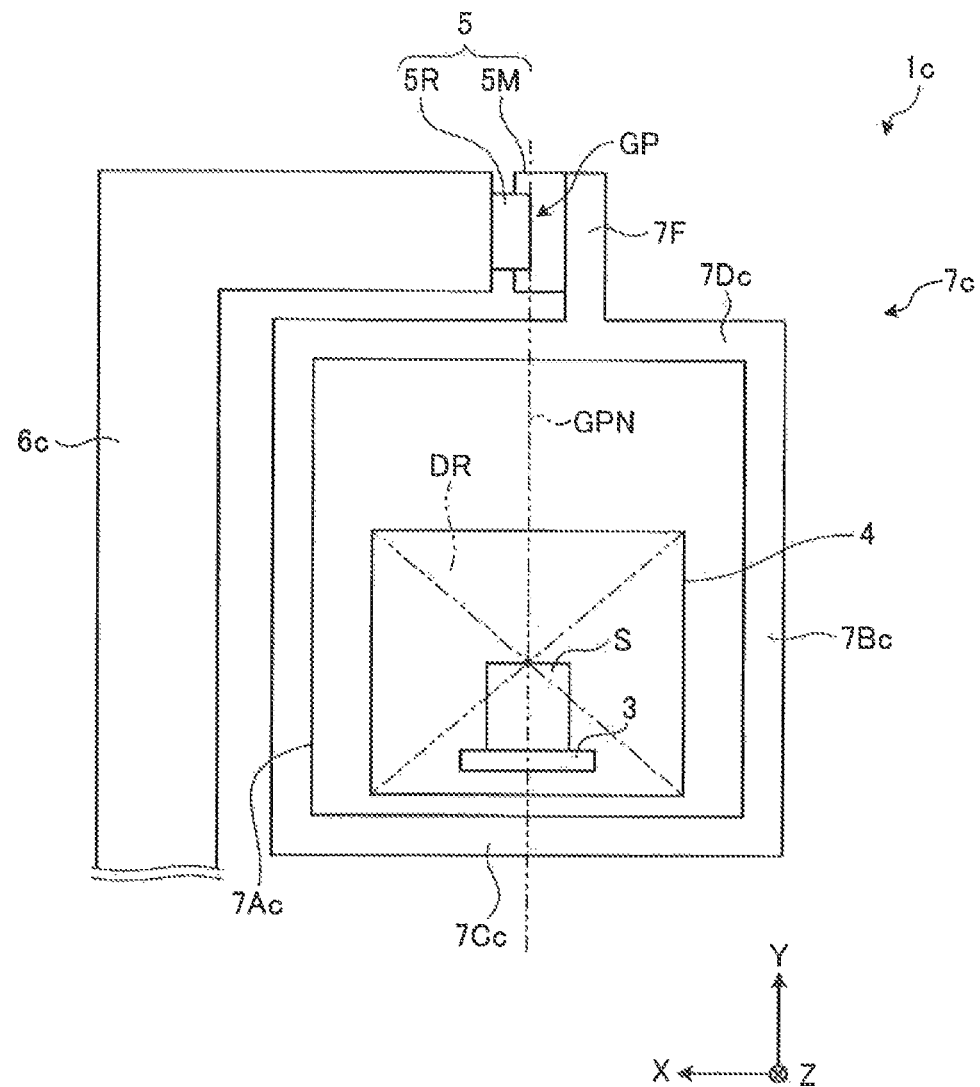
FIG. 25 is a diagram illustrating a variation on a table support body.

FIG. 25 is a diagram illustrating a variation on the table support body. In each of the aforementioned table support bodies 7, 7a, and 7b, the movement in the optical axis Zr is guided using a total of two guide devices, namely the first guide device 5A and the second guide device 5B. Movement of a table support body 7c according to the present variation in the optical axis Zr direction is guided by a single guide device 5. This table support body 7c is a substantially O-shaped structure in which a first member 7Ac, a second member 7Bc, a third member 7Cc, and a fourth member 7Dc are connected at corresponding end portions thereof, respectively. In the table support body 7c, the table 3 and the detection region DR of the detector 4 are disposed within an area surrounded by the first member 7Ac, the second member 7Bc, the third member 7Cc, and the fourth member 7Dc. The fourth member 7Dc has, between both end portions thereof, a flange portion 7F that extends outward. The guide device 5 is attached to the flange portion 7F. Like the table support body 7 according to the aforementioned embodiment, in the table support body 7c according to this variation, the table 3, the table main body 3B, the first mobile member 11, the base 12, and the second mobile member 14 are attached to the first member 7Ac and the second member 7Bc by the two guide mechanisms 15 and 15.

The rail 5R of the guide device 5 is attached to a support body 6c. The movement member 5M of the guide device 5 is attached to the flange portion 7F of the table support body 7c. The guide plane GP of the guide device 5 is a plane that is parallel to the optical axis Zr and that regulates the movement of the table 3, and is orthogonal to the X-axis in this example. A plane GPN that contains the guide plane GP and is parallel to the guide plane GP, or in other words, the guide plane GP, passes through the detection region DR of the detector 4, as illustrated in FIG. 25. Accordingly, the detection device 1c that includes the table support body 7c can reduce positional skew in the subject S caused by the position of the guide plane GP in a direction orthogonal to the guide plane GP varying along the Z-axis direction. As a result, the detection device 1c can suppress a drop in the detection accuracy. This table support body 7c is a structure in which the first member 7Ac, the second member 7Bc, the third member 7Cc, and the fourth member 7Dc are connected at the corresponding end portions thereof, respectively, and thus the rigidity thereof can be increased. As a result, the table support body 7c can more effectively suppress deformation due to the loads of the table 3, the subject S, and the like, and thus the detection device 1c that includes this table support body 7c improves the positioning accuracy of the table 3 and the detection accuracy.

Figure 26:
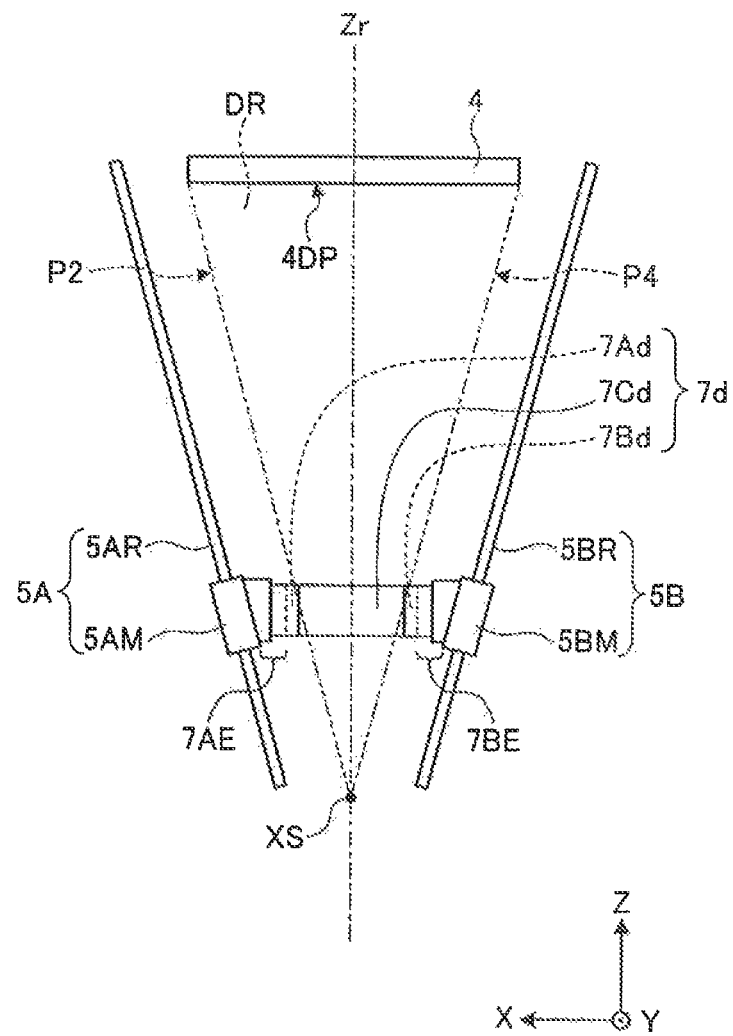
FIG. 26 is a diagram illustrating a variation on the arrangement of a first guide device and a second guide device.

FIG. 26 is a diagram illustrating a variation on the arrangement of the first guide device and the second guide device. In the aforementioned embodiment, the rail 5AR of the first guide device 5A and the rail 5BR of the second guide device 5B are disposed so that both are parallel to the optical axis Zr, as illustrated in FIG. 7. In other words, both are disposed so as to be parallel. In the present embodiment, it is sufficient for the first guide device 5A and the second guide device 5B to be disposed on either side of the optical axis Zr and outside of the detection region DR of the detector 4, and thus it is not necessary for the two to be parallel. In this example, the rail 5AR of the first guide device 5A is disposed parallel to a plane P2 that defines the detection region DR, and the rail 5BR of the second guide device 5B is disposed parallel to a plane P4 that defines the detection region DR. The detection region DR is a quadrangular cone-shaped region that takes the light-emission region XS of the X-ray source 2 as its apex and the incidence surface 4DP of the detector 4 as its base. Accordingly, a gap between the rail 5AR of the first guide device 5A and the rail 5BR of the second guide device 5B increases as the two progress from the light-emission region XS of the X-ray source 2 toward the detector 4.

In a table support body 7d, a first member 7Ad is attached to the first guide device 5A, and a second member 7Bd is attached to the second guide device 5B. The first member 7Ad and the second member 7Bd are each connected at one end portion to a third member 7Cd. Connection mechanisms 7AE and 7BE that are each capable of extending and contracting are attached between the first member 7Ad and the first guide device 5A and between the second member 7Bd and the second guide device 5B, respectively. The connection mechanisms 7AE and 7BE are mechanisms that extend when a distance between the first member 7Ad and the first guide device 5A and a distance between the second member 7Bd and the second guide device 5B increase, and contract when the stated distances decrease. The connection mechanisms 7AE and 7BE absorb changes in the stated distances resulting from the table support body 7d moving in the optical axis Zr direction. According to this structure, the table support body 7d can move in the optical axis Zr direction even in the case where the rails 5AR and 5BR are disposed so that the gap between the rail 5AR of the first guide device 5A and the rail 5BR of the second guide device 5B increases from the light-emission region XS of the X-ray source 2 toward the detector 4.

Figure 27:
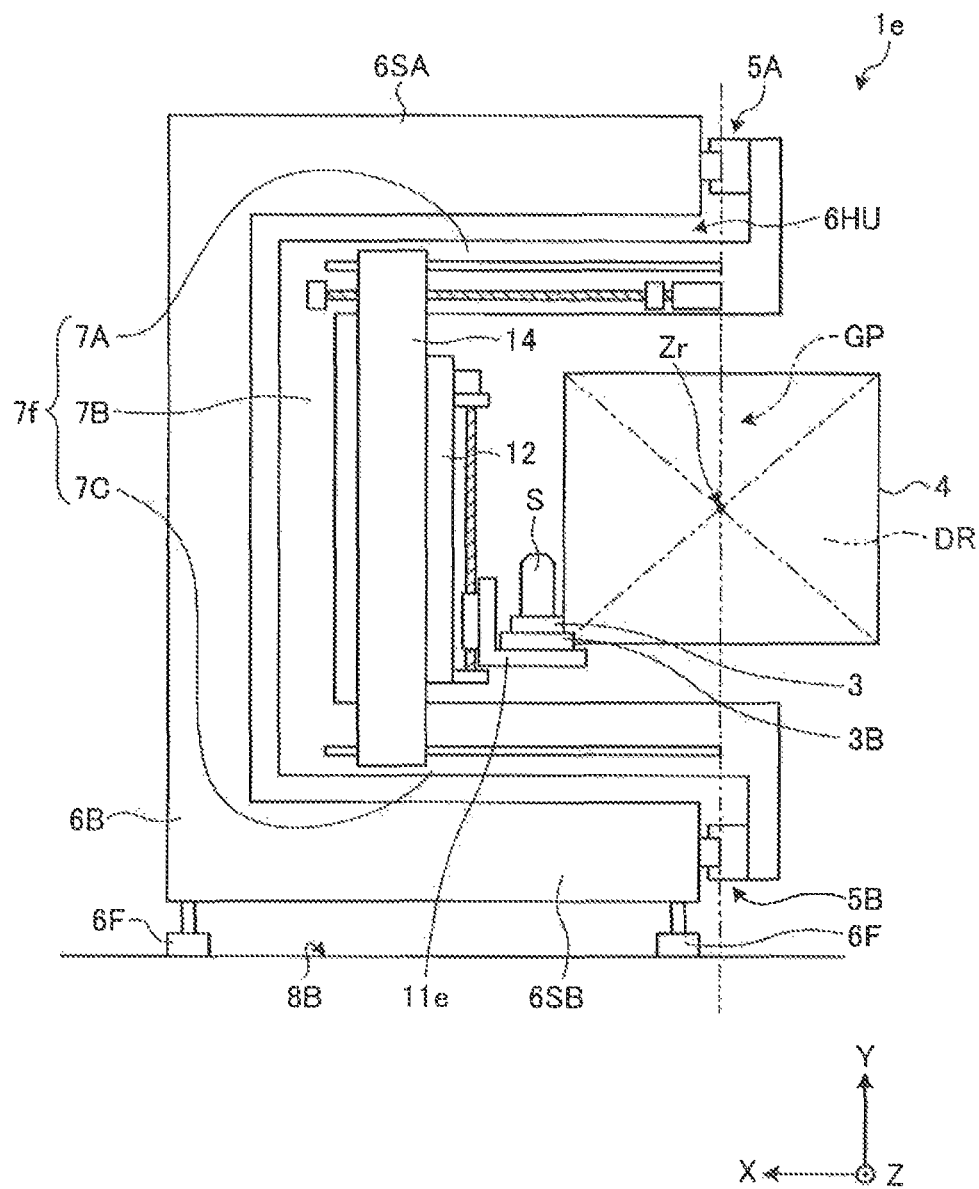
FIG. 27 is a diagram illustrating a detection device according to a variation on an embodiment.

FIG. 27 is a diagram illustrating a detection device according to a variation on the embodiment. This detection device 1e corresponds to the detection device 1 according to the embodiment being placed on its side, with the plurality of legs 6F being attached to the second side wall 6SB of the support body 6 provided in the detection device 1. The legs 6F make contact with the base portion 8B of the chamber member 8 illustrated in FIG. 1. The second side wall 6SB is disposed so as to oppose the base portion 8B of the chamber member 8. In this manner, in the detection device 1e, the second side wall 6SB faces the installation side, or in other words, the side where the base portion 8B of the chamber member 8 is located. The second side wall 6SB is positioned downward, and the first side wall 6SA that opposes the second side wall 6SB is positioned upward. Note that the plurality of legs 6F may be attached to the first side wall 6SA and the first side wall 6SA may be positioned downward.

An opening 6HU of the support body 6 is positioned to the side, or in other words, on the X-axis side. The table 3 and the table main body 3B are attached to and supported by the support body 6 using a first mobile member lie, the base 12, the second mobile member 14, the table support body 7, the first guide device 5A, and the second guide device 5B. The first member 7A and the second member 7B of the table support body 7 extend from the opening 6HU of the support body 6 toward the base portion 6B. The first mobile member 11e that supports the table 3 and the table main body 3B move in the Y-axis direction. The second mobile member 14 moves in the X-axis direction. The table support body 7 moves in the optical axis Zr direction. The guide plane GP defined by the first guide device 5A and the second guide device 5B passes through the detection region DR of the detector 4. In this manner, the detection device 1 according to the embodiment may be placed on its side, as with the detection device 1e according to the variation.

Figure 28:
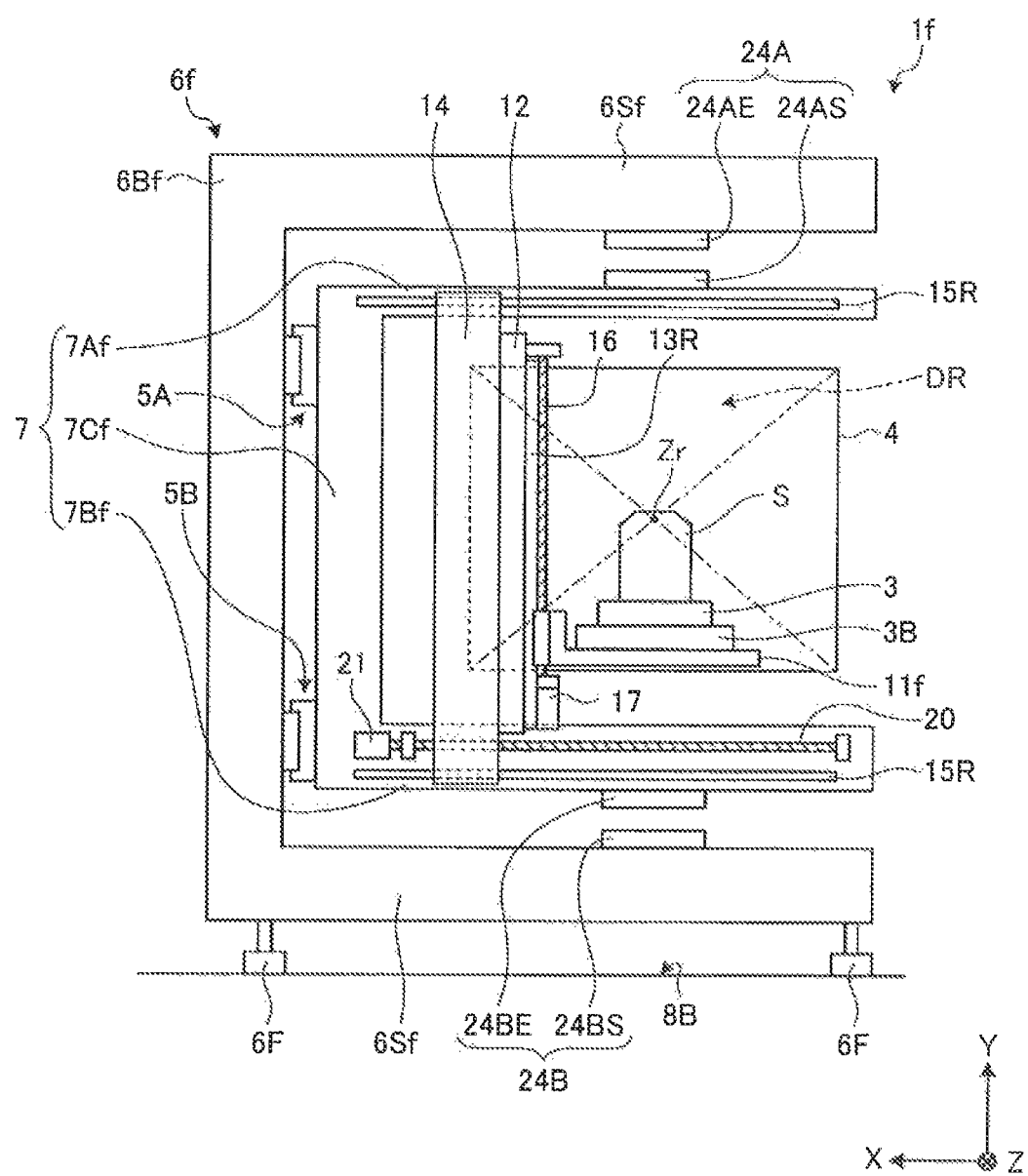
FIG. 28 is a diagram illustrating a detection device according to a variation on an embodiment.
Figure 29:
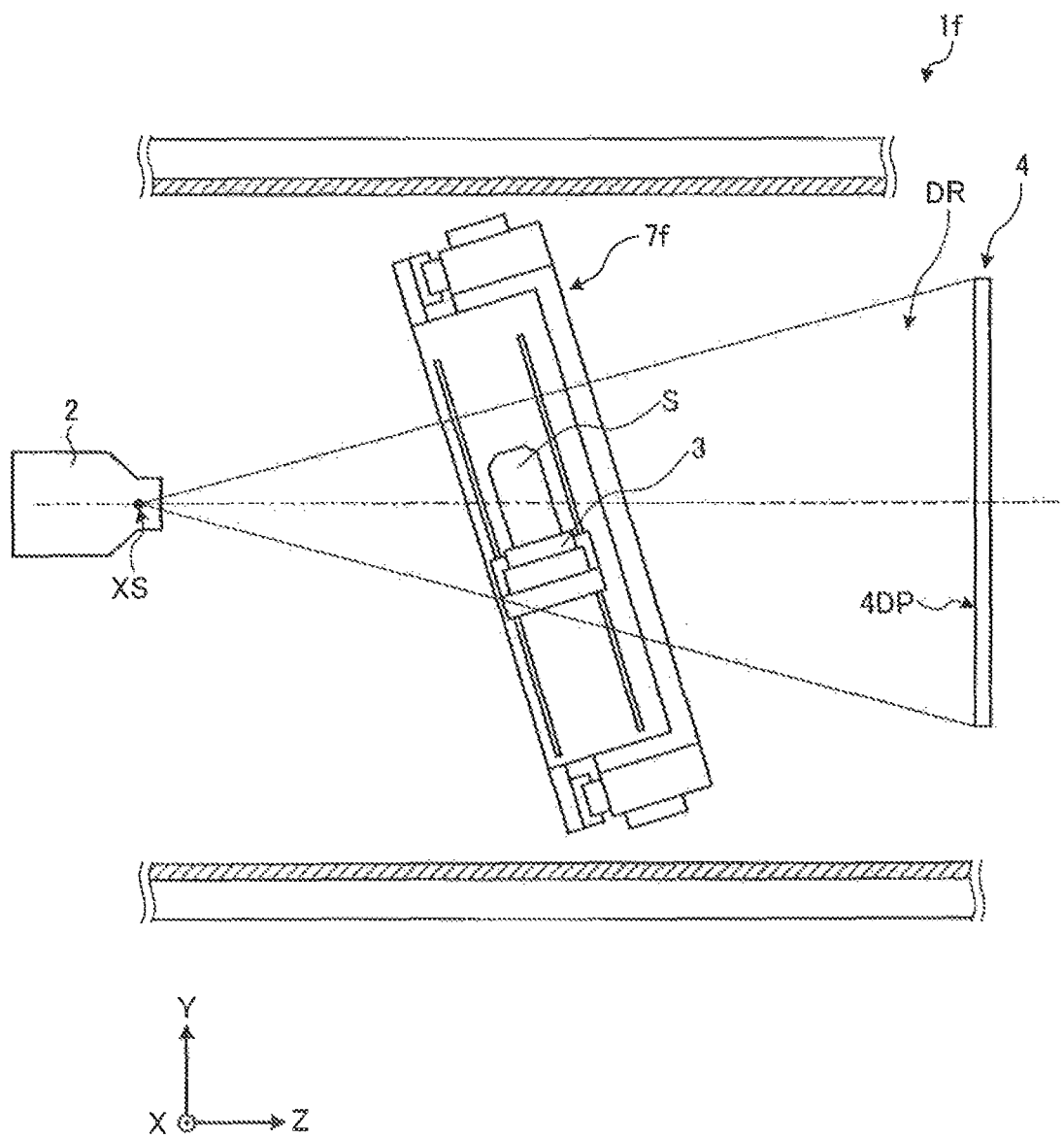
FIG. 29 is a diagram illustrating a detection device according to a variation on an embodiment.

FIGS. 28 and 29 are diagrams illustrating a detection device according to a variation on the embodiment. This detection device 1f includes a support body 6f, the table 3 that supports the subject S, a table support body 7f that supports the table 3, the detector 4, and the X-ray source 2 illustrated in FIG. 29. The support body 6f has a base portion 6Bf and a pair of side walls 6Sf and 6Sf that rise from the base portion 6Bf and oppose each other. The plurality of legs 6F are attached to one of the side walls 6Sf. The plurality of legs 6F make contact with the base portion 8B of the chamber member 8 illustrated in FIG. 1. The support body 6f supports the table 3 using the table support body 7f. The first guide device 5A and the second guide device 5B are attached to a surface of the base portion 6Bf on the side where the side walls 6Sf and 6Sf are located. The first guide device 5A and the second guide device 5B are interposed between the base portion 6Bf and the table support body 7f, and guide the movement of the table support body 7f in the optical axis Zr direction.

The table 3 and the table main body 3B are attached to a first mobile member 11f. The first mobile member 11f is supported by the base 12 using the rails 13R that serve as guide members and are attached to the base 12. The rails 13R guide movement of the first mobile member 11f in the Y-axis direction. The second mobile member 14 attached to the base 12 is supported by the table support body 7f using the pair of rails 15R and 15R serving as guide members. The pair of rails 15R and 15R guide movement of the second mobile member 14 in the X-axis direction. According to this structure, the table 3 and the table main body 3B are supported by the table support body 7 using the first mobile member 11f, the base 12, and the second mobile member 14. The table support body 7f moves in the optical axis Zr direction, and thus the table 3 also moves in the optical axis Zr direction.

The actuator 17 causes the first mobile member 11f to move in the Y-axis direction using the screw shaft 16 to which the output shaft of the actuator 17 is attached. The actuator 21 causes the second mobile member 14 to move in the X-axis direction using the screw shaft 20 to which the output shaft of the actuator 17 is attached.

The table support body 7f has a first member 7Af, a second member 7Bf, and a third member 7Cf that connects one end portion of each of the first member 7Af and the second member 7Bf. The first member 7Af, the second member 7Bf, and the third member 7Cf are all plate-shaped members. The first member 7Af and the second member 7Bf are disposed so that the plate surfaces thereof oppose each other and are substantially parallel to each other. The third member 7Cf is orthogonal to the first member 7Af and the second member 7Bf. The pair of rails 15R and 15R that guide the second mobile member 14 are attached to the first member 7Af and the second member 7Bf, respectively. The first guide device 5A and the second guide device 5B are attached to the third member 7Cf.

The first member 7Af and the second member 7Bf of the table support body 7f are disposed on either side of the optical axis Zr and outside of the detection region DR of the detector 4. The linear encoder 24A is provided between the first member 7Af and one of the side walls 6Sf. The linear encoder 24B is provided between the second member 7Bf and the other of the side walls 6Sf. The encoder head 24AE of the linear encoder 24A is attached to the first member 7Af. The linear scale 24AS is attached to a part of the one side wall 6Sf that opposes the encoder head 24AE. The encoder head 24BE of the linear encoder 24B is attached to the second member 7Bf. The linear scale 24BS is attached to a part of the other side wall 6Sf that opposes the encoder head 24BE.

The two linear encoders 24A and 24B are disposed on either side of the optical axis Zr, on the outside of the detection region DR. In other words, the two linear encoders 24A and 24B are disposed on the outside of the detection region DR and on either side of the detection region DR. The linear encoders 24A and 24B measure the movement amount of the table support body 7f relative to the support body 6f in the optical axis Zr direction. The control device 9 illustrated in FIG. 1 controls the movement amount of the table support body 7f on the basis of the movement amount of the table support body 7f measured by at least one of the linear encoder 24A and the linear encoder 24B, for example.

A tilt of the table support body 7f central to the X-axis (a tilt of the table support body 7f relative to the XZ plane) is found by using both of the two linear encoders 24A and 24B disposed outside of the detection region DR and on either side of the detection region DR, as illustrated in FIG. 29. By using measurement values from the two linear encoders 24A and 24B, the control device 9 illustrated in FIG. 1 can more accurately find positional skew of the subject S in the optical axis Zr direction caused by the tilt of the table support body 7f central to the X-axis and control the position of the table 3. As a result, the control device 9 can accurately control the position of the subject S in the optical axis Zr direction. As a result, the detection device 1f can suppress a drop in the detection accuracy.

Figure 30:
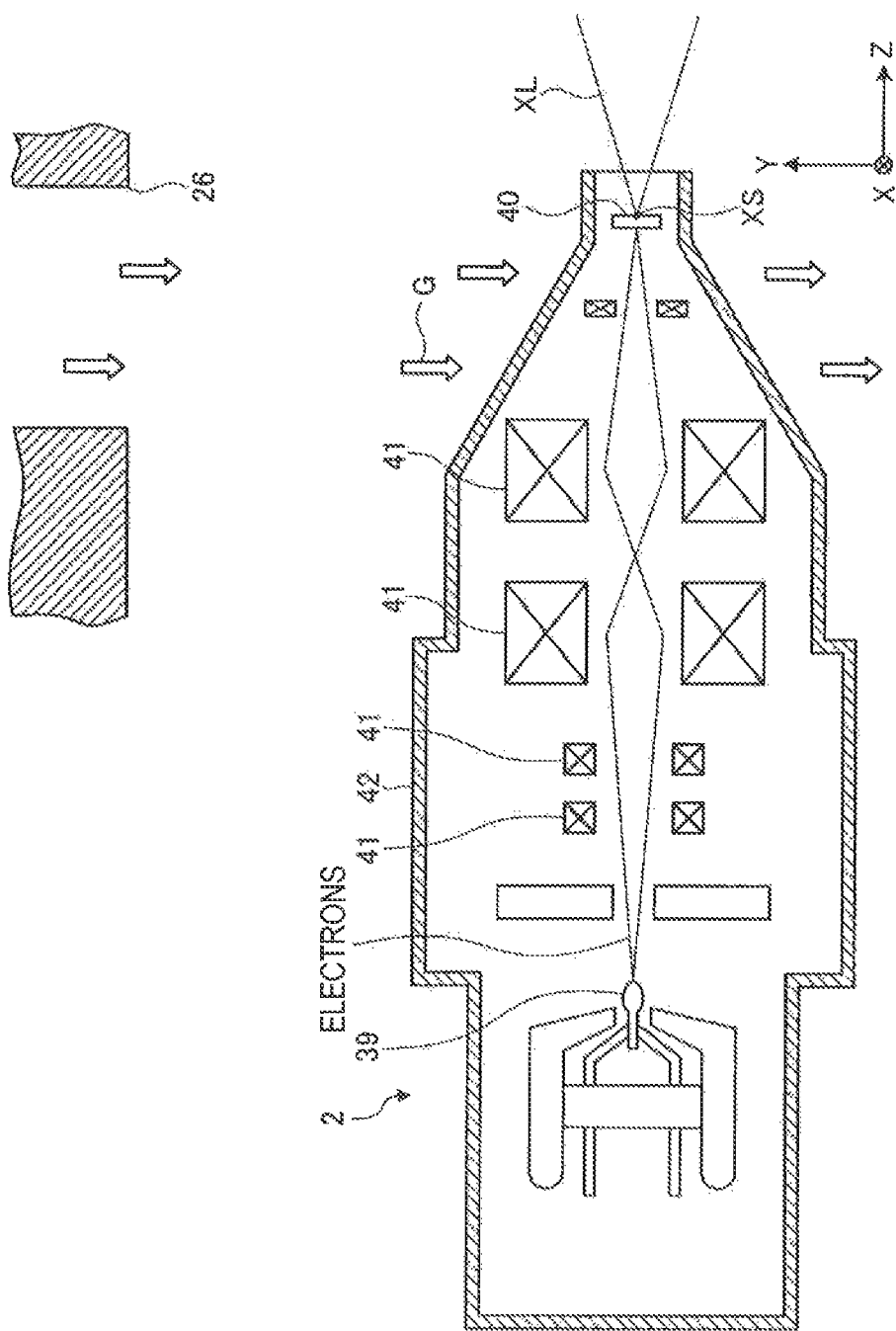
FIG. 30 is a cross-sectional view illustrating an example of an X-ray source according to an embodiment.

FIG. 30 is a cross-sectional view illustrating an example of the X-ray source according to the present embodiment. The X-ray source 2 will be described in detail next. In FIG. 30, the X-ray source 2 includes a filament 39 that emits electrons, a target 40 that emits X-rays resulting from electron collisions or electron transmission, and electron conducting members 41 that conduct the electrons to the target 40. In addition, in the present embodiment, the X-ray source 2 includes a housing 42 that houses at least some of the electron conducting members 41. In the present embodiment, the filament 39, the electron conducting members 41, and the target 40 are all housed within the housing 42.

The filament 39 contains tungsten, for example. When a current flows through the filament 39 and the filament 39 is heated by the current, electrons (thermoelectrons) are discharged from the filament 39. The shape of the filament 39 has a tapered end, and the electrons are discharged from that tapered portion. The filament 39 is wound into a coil shape. The target 40 contains tungsten, for example, and emits X-rays due to electron collisions or electron transmission. In the present embodiment, the X-ray source 2 is what is known as a transmissive type. In the present embodiment, the target 40 emits the X-rays XL due to electron transmission. A part of the target 40 that emits the X-rays XL is the light-emission region XS. Although the X-ray source 2 is a transmissive-type X-ray source in the present embodiment, the X-ray source 2 may be a reflective-type X-ray source. Furthermore, although the target 40 is fixed, the target may be mobile. For example, in FIG. 30, the target 40 may be disposed so as to be mobile in the Y-axis direction, and the position of the target 40 that is irradiated by electrons may be made variable as appropriate. Meanwhile, a rotating target system in which, for example, the target 40 rotates and the position of the target 40 that is irradiated by electrons is made variable may be employed.

For example, assuming the target 40 serves as an anode and the filament 39 serves as a cathode, when a voltage is applied between the target 40 and the filament 39, thermo-electrons jumping from the filament 39 accelerate toward the target (anode) 40 and irradiate the target 40. X-rays are emitted from the target 40 as a result. The electron conducting members 41 are disposed in at least part of the periphery of the path of the electrons from the filament 39, between the filament 39 and the target 40. The electron conducting members 41 include an electron lens such as a focusing lens, and an objective lens, or a polarizer, and conduct the electrons from the filament 39 to the target 40. The electron conducting members 41 cause electrons to collide with a partial region (an X-ray focal point) of the target 40. The dimension of the region of the target 40 where the electrons collide (a spot size) is extremely small. What is substantially a point X-ray source is formed as a result.

In the present embodiment, the temperature-controlled gas G is supplied to an outer surface of the housing 42 from the supply port 26. In the present embodiment, the supply port 26 opposes at least a part of the outer surface of the housing 42. In the present embodiment, the supply port 26 is disposed higher (on the +Y side) than the X-ray source 2 (the housing 42). The supply port 26 blows the gas G onto the outer surface of the housing 42 of the X-ray source 2 from above the X-ray source 2. In the X-ray source 2, when the target 40 is irradiated with electrons, some of the electron energy results in the X-rays XL, and some of the energy results in heat. Irradiating the target 40 with electrons causes the temperature of the target 40, the space around the target 40, and components disposed in the vicinity of the target 40 to rise.

When the temperature of the target 40 rises, the target 40 may thermally deform, the housing 42 may thermally deform, the relative positions of the filament 39 and the target 40 may change, for example. The temperature of the internal space SP in which the X-ray source 2 is disposed may change if the temperature of the X-ray source 2 including the target 40 rises. If the temperature of the X-ray source 2 including the target 40 rises, at least some of the table 3, the first mobile member 11, the base 12, the second mobile member 14, and the like may deform, the first guide device 5A and the second guide device 5B may thermally deform, the detector 4 may thermally deform, for example. If the temperature of the X-ray source 2 rises, the relative positions of the X-ray source 2 and the table 3 may change, the relative positions of the X-ray source 2 and the detector 4 may change, the relative positions of the table 3 and the detector 4 may change. In this manner, if the temperature of the X-ray source 2 changes, at least some of the members of the detection device 1 may thermally deform, the relative positions between members may change. The detection accuracy (scanning accuracy, measurement accuracy) of the detection device 1 may drop as a result.

In the present embodiment, the temperature-controlled gas G is supplied to at least part of the X-ray source 2 that produces heat, and thus at least some of the members in the internal space SP including the X-ray source 2 thermally deforming, the temperature of the internal space SP changing, the relative positions of members in the internal space SP changing are suppressed. Meanwhile, a plurality of members and devices such as the X-ray source 2, the table 3, and the detector 4 are disposed in the internal space SP, and in the present embodiment, the temperature-controlled gas G is supplied to at least part of the X-ray source 2, which, of that plurality of members, produces heat. Accordingly, of the plurality of members such as the X-ray source 2, the table 3, and the detector 4, in the internal space SP, a higher percentage of the temperature-controlled gas G reaches the X-ray source 2 than the other members. Meanwhile, a plurality of members such as the X-ray source 2, the table 3, and the detector 4 are disposed in the internal space SP, and in the present embodiment, the temperature-controlled gas G is supplied to at least part of the X-ray source 2. In the present embodiment, the temperature in the periphery of the X-ray source 2, which is a localized space within the internal space SP, can be adjusted. In addition, although a plurality of members such as the X-ray source 2, the table 3, and the detector 4 are disposed within the internal space SP, the temperature of only a part of the X-ray source 2 that the temperature-controlled gas G reaches can be adjusted, instead of supplying the temperature-controlled gas G to all of those plural members. An example of operations performed by the detection device according to the present embodiment will be described next.

Figure 31:
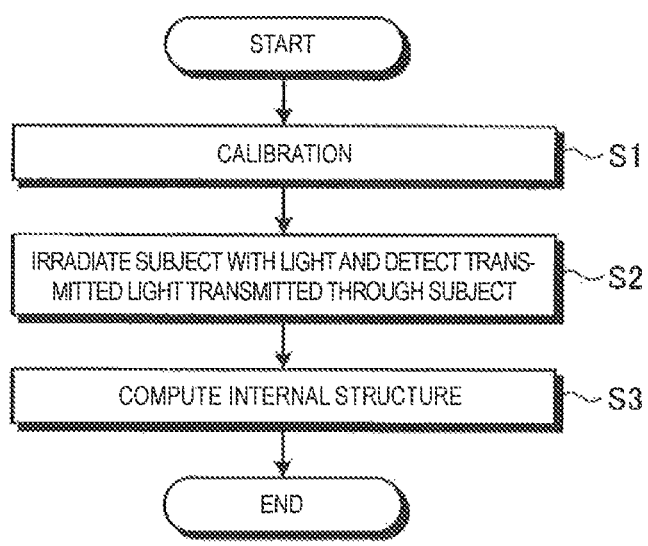
FIG. 31 is a flowchart illustrating an example of operations performed by a detection device according to an embodiment.
Figure 32:
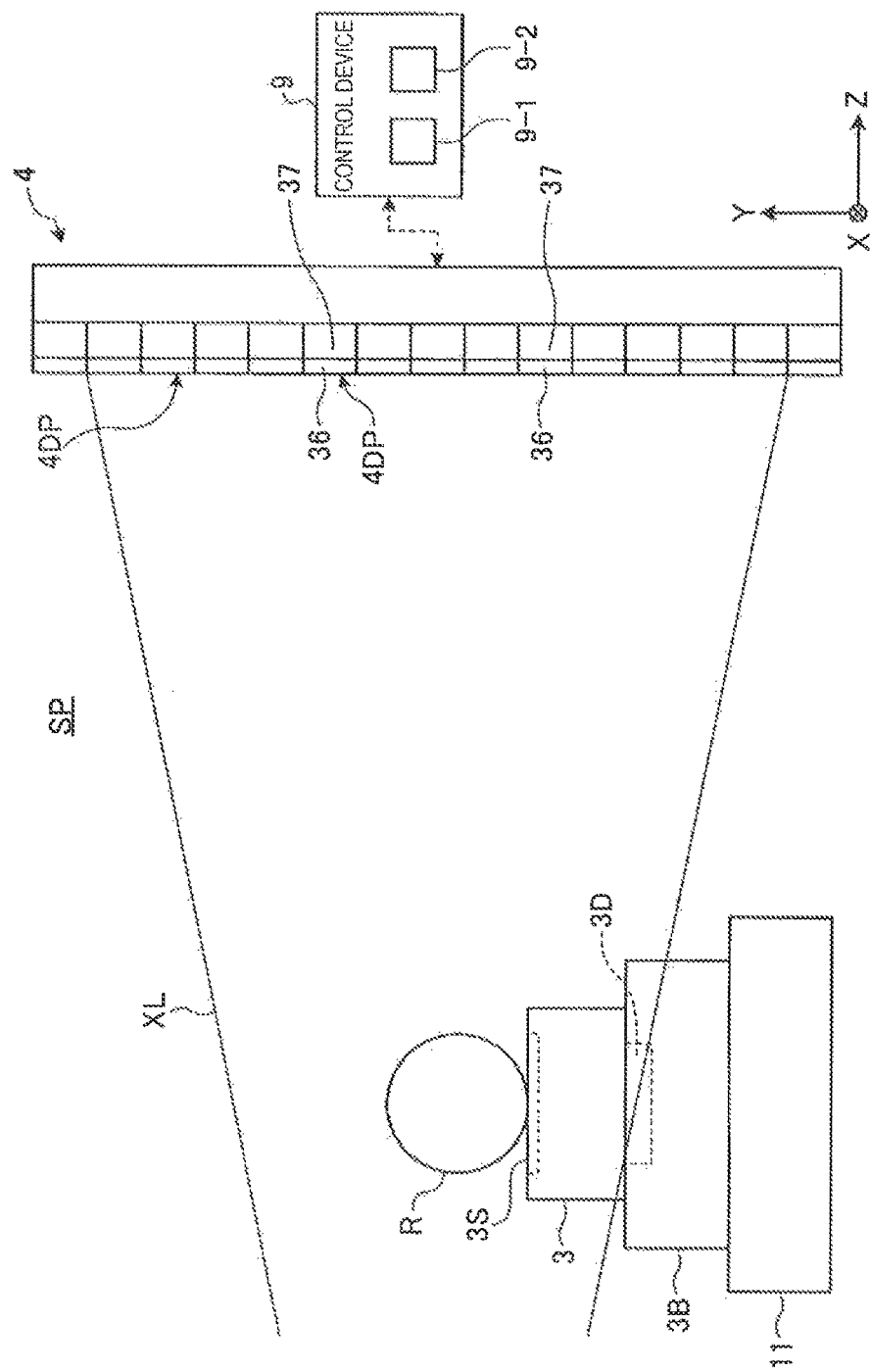
FIG. 32 is a diagram illustrating an example of operations performed by a detection device according to an embodiment.
Figure 33:
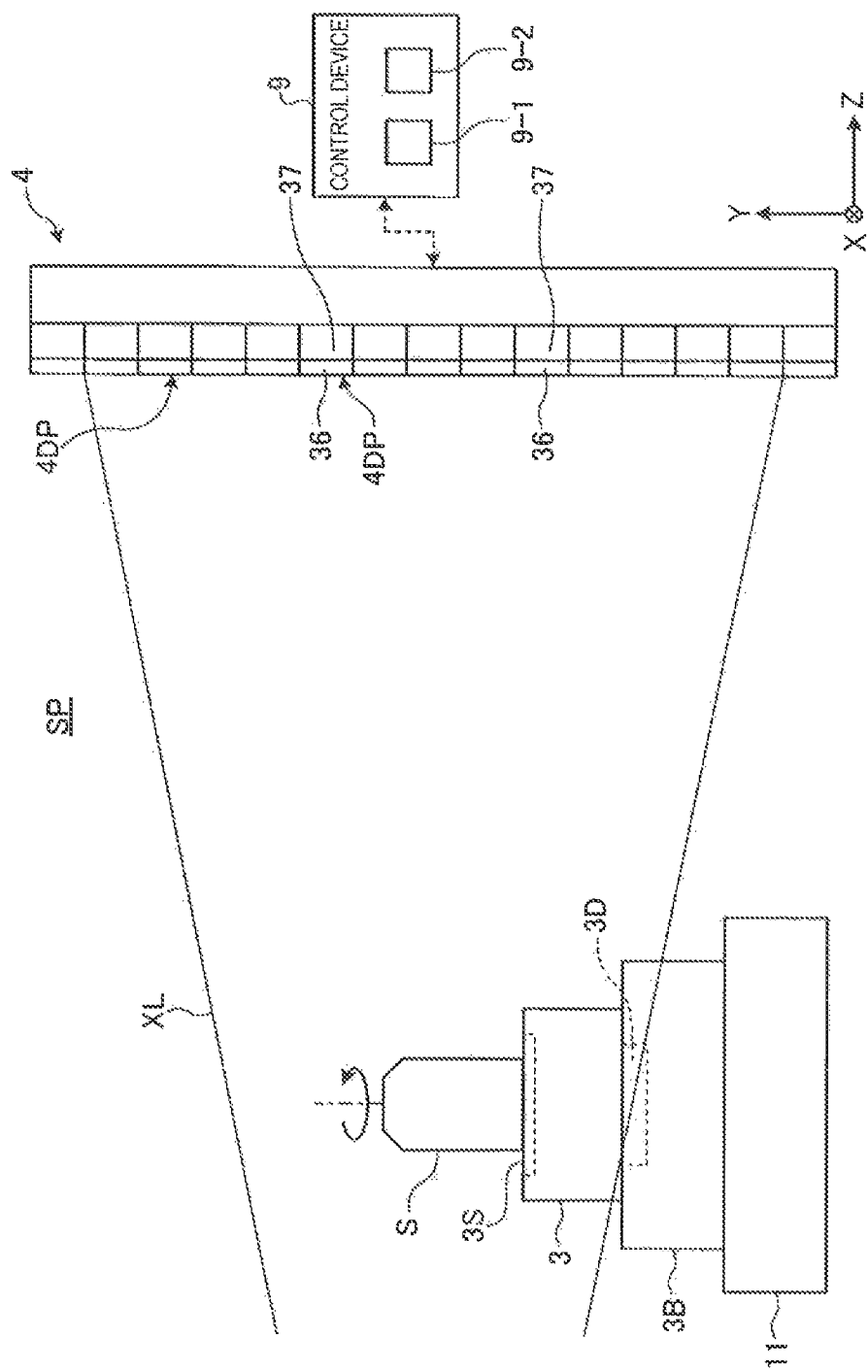
FIG. 33 is a diagram illustrating an example of operations performed by a detection device according to an embodiment.

FIG. 31 is a flowchart illustrating an example of operations performed by the detection device according to the embodiment. FIG. 32 is a diagram illustrating an example of operations performed by the detection device according to the embodiment. FIG. 33 is a diagram illustrating an example of operations performed by the detection device according to the embodiment. As indicated by the flowchart in FIG. 31, in the present embodiment, the detection device 1 is calibrated (step SA1), the subject S is irradiated with the X-rays XL and the transmitted X-rays transmitted through the subject S are detected (step SA2), and the internal structure of the subject S is computed (step SA3).

The calibration (step SA1) will be described. As illustrated in FIG. 32, in the calibration, a reference member R that is different from the subject S is supported by the table 3. In addition, in the calibration, the temperature-controlled gas G is supplied to at least part of the X-ray source 2 from the supply port 26. By supplying the temperature-controlled gas G to the X-ray source 2 from the supply port 26, the temperature of the internal space SP including the X-ray source 2 is adjusted by the gas G. In the following descriptions, the temperature of the internal space SP including the X-ray source 2, which has been adjusted by the gas G supplied from the supply port 26, will be called a predetermined temperature Ta as appropriate.

As illustrated in FIG. 32, in the present embodiment, the reference member R is a sphere. An outer shape (dimension) of the reference member R is already known. The reference member R is an object that does not easily experience thermal deformation. The reference member R is an object that at least experiences less thermal deformation than the subject S. Even if the temperature in the internal space SP changes, the outer shape (dimension) of the reference member R will not substantially change. Note that the shape of the reference member R is not limited to a sphere in the present embodiment. The control device 9 adjusts the position of the table 3 supporting the reference member R by controlling the rotational driving device 3D of the table 3 and the actuators 17, 21, and 28, while measuring the position of the table 3 using the rotary encoder 10 and the linear encoders 19, 23A, 23B, 24A, and 24B. The control device 9 adjusts the position of the table 3 so that the reference member R is disposed as a reference position Pr.

The control device 9 applies a current to the filament 39 so that X-rays are emitted from the X-ray source 2, in parallel with at least some of the supply of the gas G from the supply port 26. Upon doing so, the filament 39 is heated and electrons are discharged from the filament 39. The target 40 is irradiated with the electrons discharged from the filament 39. X-rays are emitted from the target 40 as a result. The reference member R is irradiated with the X-rays XL emitted from the X-ray source 2. Upon the reference member R being irradiated with the X-rays XL from the X-ray source 2 at the predetermined temperature Ta, the X-rays XL the reference member R is irradiated with transmit through the reference member R. The transmitted X-rays transmitted through the reference member R are incident on the incidence surface 4DP of the detector 4. The detector 4 detects the transmitted X-rays transmitted through the reference member R. At the predetermined temperature Ta, the detector 4 detects an image of the reference member R obtained on the basis of the transmitted X-rays transmitted through the reference member R. In the present embodiment, a dimension (size) of the image of the reference member R obtained at the predetermined temperature Ta is represented by a dimension Wa. The result of the detection performed by the detector 4 is outputted to the control device 9.

The control device 9 calculates the relative positions of the X-ray source 2, the reference member R, and the detector 4 on the basis of the dimension of the image of the reference member R and the dimension of the reference member R. Meanwhile, although there is only a single sphere in the present embodiment, a plurality of spheres may be used. In the case where a plurality of spheres are used, the positions of the spheres may be varied in one or both of the Y-axis direction and the Z-axis direction, for example. Furthermore, in the case where a plurality of spheres are used, the relative positions between the X-ray source 2, the reference members R, and the detector 4 may be calculated on the basis of distances between the reference members R, rather than the image of the reference member R. The calculation of the distances between the reference members R may use distances between center positions of the reference members R or distances between predetermined positions in the profiles of the reference members R.

In the present embodiment, when a temperature T in the internal space SP changes, the dimension (size) of the image obtained on the basis of the transmitted X-rays changes. The dimension of the image obtained on the basis of the transmitted X-rays is a dimension of the image obtained by the detector 4, and includes a dimension of an image formed on the incidence surface 4DP, for example. For example, when the temperature T changes, the relative positions of the X-ray source 2, the reference member R, and the detector 4 (relative positions with respect to the Z-axis direction) change. For example, in the case where the internal space SP is at the reference temperature (ideal temperature, target temperature) Tr, the dimension of an image obtained by the detector 4 on the basis of the X-rays XL with which the reference member R disposed as the reference position Pr has been irradiated is a reference dimension Wr.

In the case where the internal space SP is at a temperature TX that is different from the reference temperature Tr, for example, at least one of the X-ray source 2, the table 3, the detector 4, and the chamber member 8 may thermally deform, and the relative positions of the X-ray source 2, the reference member R supported by the table 3, and the detector 4 may change. Accordingly, even if, for example, the position of the table 3 is adjusted on the basis of measurement results from the rotary encoder 10 and the linear encoders 19, 23A, 23B, 24A, and 24B so as to dispose the reference member R at the reference position Pr, it is possible that the reference member R will not actually be disposed as the reference position Pr. To rephrase, in the case where the internal space SP is at the temperature TX, the reference member R may be disposed at a position PX that is different from the reference position Pr. Note that the position PX includes a relative position of the reference member R with respect to at least one of the X-ray source 2 and the detector 4.

Meanwhile, when the internal space SP is at the temperature TX and the relative positions of the X-ray source 2, the reference member R, and the detector 4 change, a dimension WX of the image obtained by the detector 4 will be different from the reference dimension Wr. In the present embodiment, the control device 9 includes a storage device. A relationship between the temperature T in the internal space SP, and the dimension (size) of an image of the reference member R obtained on the basis of the transmitted X-rays that, of the X-rays XL with which the reference member R has been irradiated, have transmitted through the reference member R at the temperature T, is stored in the storage device. As described earlier, the relative positions of the X-ray source 2, the reference member R, and the detector 4 change as the temperature T in the internal space SP changes. The dimension of the image obtained by the detector 4 also changes as those relative positions change. A relationship between the relative positions and the dimension of the image is also stored in the storage device. Note that the information stored in the storage device is found in advance through at least one of experiments and simulations.

By doing so, the control device 9 can calculate the relative positions of the X-ray source 2, the reference member R, and the detector 4 at the temperature T on the basis of the information stored in the storage device and the dimension of the image of the reference member R obtained by the detector 4. For example, in the case where the internal space SP is at the predetermined temperature Ta, the control device 9 can calculate the relative positions of the X-ray source 2, the reference member R, and the detector 4 at the predetermined temperature Ta on the basis of the information stored in the storage device and the dimension Wa of the image of the reference member R obtained by the detector 4.

After the calibration ends, the subject S is detected (step SA2). As illustrated in FIG. 33, the subject S is supported by the table 3 during the detection. The control device 9 controls the table 3 and disposes the subject S between the X-ray source 2 and the detector 4. In addition, in the detection, the temperature-controlled gas G is supplied to at least part of the X-ray source 2 from the supply port 26. By supplying the temperature-controlled gas G to the X-ray source 2 from the supply port 26, the temperature of the internal space SP including the X-ray source 2 is adjusted by the gas G.

The control device 9 supplies the temperature-controlled gas G from the supply port 26 to the internal space SP including the X-ray source 2 so that the internal space SP reaches the predetermined temperature Ta. The control device 9 adjusts the position of the table 3 supporting the subject S by controlling the rotational driving device 3D of the table 3 and the actuators 17, 21, and 28, while measuring the position of the table 3 using the rotary encoder 10 and the linear encoders 19, 23A, 23B, 24A, and 24B. The control device 9 applies a current to the filament 39 so that X-rays are emitted from the X-ray source 2, in parallel with at least some of the supply of the gas G from the supply port 26. Upon doing so, the filament 39 is heated and electrons are discharged from the filament 39. The target 40 is irradiated with the electrons discharged from the filament 39. X-rays are emitted from the target 40 as a result.

The subject S is irradiated with at least a portion of the X-rays XL emitted from the X-ray source 2. Upon the subject S being irradiated with the X-rays XL from the X-ray source 2 at the predetermined temperature Ta, at least a portion of the X-rays XL with which the subject S is irradiated transmit through the subject S. The transmitted X-rays transmitted through the subject S are incident on the incidence surface 4DP of the detector 4. The detector 4 detects the transmitted X-rays transmitted through the subject S. At the predetermined temperature Ta, the detector 4 detects an image of the subject S obtained on the basis of the transmitted X-rays transmitted through the subject S. In the present embodiment, a dimension (size) of the image of the subject S obtained at the predetermined temperature Ta is represented by a dimension Ws. The result of the detection performed by the detector 4 is outputted to the control device 9.

In the present embodiment, the control device 9 uses the calibration result to correct the result of detecting the transmitted X-rays which, of the X-rays XL with which the subject S has been irradiated at the predetermined temperature Ta, transmitted through the subject S. For example, the control device 9 corrects the image of the subject S obtained at the predetermined temperature Ta so that the image of the subject S obtained at the predetermined temperature Ta corresponds to an image obtained at the reference temperature Tr. For example, in the case where the dimension of the image of the subject S obtained at the predetermined temperature Ta is the dimension Ws, the control device 9 multiplies the dimension Ws by Wr/Wa, which serves as a correction value. In other words, the control device 9 executes Ws×(Wr/Wa) as a computation. Through this processing, the control device 9 can calculate the image (the dimension of the image) of the subject S at the reference temperature Tr even in the case where the actual temperature in the internal space SP is the predetermined temperature Ta.

In the present embodiment, the control device 9 irradiates the subject S with the X-rays XL from the X-ray source 2 while changing the position of the subject S in order to change the region of the subject S that is irradiated with the X-rays XL from the X-ray source 2. In other words, the control device 9 irradiates the subject S with the X-rays XL from the X-ray source 2 at each of a plurality of subject S positions, and detects the transmitted X-rays transmitted through the subject S using the detector 4. In the present embodiment, the control device 9 changes the region of the subject S irradiated with the X-rays XL from the X-ray source 2 by rotating the table 3 that supports the subject S and changing the position of the subject S relative to the X-ray source 2.

In other words, in the present embodiment, the control device 9 irradiates the subject S with the X-rays XL while rotating the table 3 that supports the subject S. The transmitted X-rays transmitted through the subject S at each position (each rotation angle) of the table 3 (X-ray transmission data) are detected by the detector 4. The detector 4 obtains the image of the subject S at each position. The control device 9 computes the internal structure of the subject S from the results of the detection performed by the detector 4 (step SA3). In the present embodiment, the control device 9 obtains the image of the subject S based on the transmitted X-rays transmitted through the subject S (the X-ray transmission data) at each position (each rotation angle) of the subject S. In other words, the control device 9 obtains a plurality of images of the subject S.

The control device 9 carries out computations on the basis of the plurality of pieces of X-ray transmission data (images) obtained by irradiating the subject S with the X-rays XL while rotating the subject S, reconstructs a tomographic image of the subject S, and obtains three-dimensional data of the internal structure (a three-dimensional structure) of the subject S. In the present embodiment, the control device 9 has an image reconstruction unit 9-1 that reconstructs the image. The image reconstruction unit 9-1 reconstructs the image using an image memory unit 9-2 that stores images obtained from the detector 4. The image obtained through the image reconstruction is once again outputted to the image memory unit 9-2. The outputted reconstructed image stored in the image memory unit 9-2 is displayed in a display, which is not illustrated. The internal structure of the subject S is computed in this manner. Accordingly, in the present embodiment, the control device 9 functions as a computing device that computes the shape of the subject S from a result of the detector 4 detecting the transmitted X-rays transmitted through the subject S. A back projection method, a filter-corrected back projection method, or a successive approximation method can be given as examples of methods for reconstructing the tomographic image of the subject. The back projection method and the filter-corrected back projection method are described in, for example, the specification of US Patent Application No. 2002/0154728. The successive approximation method, meanwhile, is described in, for example, the specification of US Patent Application No. 2010/0220908.

As described thus far, in the present embodiment, the guide plane GP that regulates the movement of the table 3 supporting the subject S passes through the detection region DR. Accordingly, the detection device 1 can suppress positional skew of the table 3 caused by changes in the position of the guide plane GP in the optical axis Zr direction, and can therefore suppress a drop in the detection accuracy. In addition, in the present embodiment, the X-ray source 2, the table 3, and the detector 4 are supported by the same support body 6. Accordingly, the detection device 1 can suppress error caused by changes in the orientations of the X-ray source 2, the table 3, and the detector 4, and can therefore suppress a drop in the detection accuracy. Furthermore, in the present embodiment, the table support body 7 is supported by the support body 6 using a dual-sided support structure, and thus warping of the table support body 7 can be suppressed. Accordingly, the detection device 1 can suppress positional skew of the table 3 supported by the table support body 7, and can therefore suppress a drop in the detection accuracy. In this manner, the present embodiment suppresses a drop in the detection accuracy of the detection device 1 by reducing causes of mechanical error in the detection device 1. Accordingly, the detection device 1 can realize accurate calibration. In addition, because the detection device 1 can realize accurate calibration and suppress a drop in the accuracy of detecting the transmitted X-rays transmitted through the subject S, the detection device 1 can obtain accurate three-dimensional data of the internal structure of the subject S (a three-dimensional structure). Accordingly, the detection device 1 is suited to precision measurement.

In addition, in the present embodiment, the temperature-controlled gas G is supplied to the X-ray source 2 from the supply port 26, and thus the temperature of the X-ray source 2 can be adjusted. Accordingly, at least part of the X-ray source 2 can be suppressed from thermally deforming. In addition, the temperature in the internal space SP can be adjusted by supplying the temperature-controlled gas G from the supply port 26, and thus the temperature in the internal space SP can be suppressed from fluctuating.

In addition, the temperature of at least some of the members and devices disposed in the internal space SP, such as the table 3, the first mobile member 11, the base 12, the second mobile member 14, and the detector 4, can be adjusted by supplying the temperature-controlled gas G from the supply port 26, and thus thermal deformation of those members and devices can be suppressed. In addition, changes in the relative positions of the X-ray source 2, the subject S 26 (the table 3), and the detector 4, for example, can be suppressed by supplying the temperature-controlled gas G from the supply port 26. Accordingly, the detection device 1 suppresses a drop in the detection accuracy. For example, the detection device 1 can accurately obtain information regarding the internal structure of the subject S.

Although the present embodiment describes varying the region of the subject S irradiated by the X-rays XL, obtaining a plurality of images of the subject S, and obtaining the three-dimensional data of the internal structure of the subject S on the basis of that plurality of images, information regarding the internal structure of the subject S may be obtained on the basis of a single image. In other words, two-dimensional data of the internal structure of the subject S may be obtained, without irradiating the subject S with the X-rays XL from different angles. An example of a procedure for measuring the shape and the like of the subject S using the detection device 1 will be described next.

Figure 34:
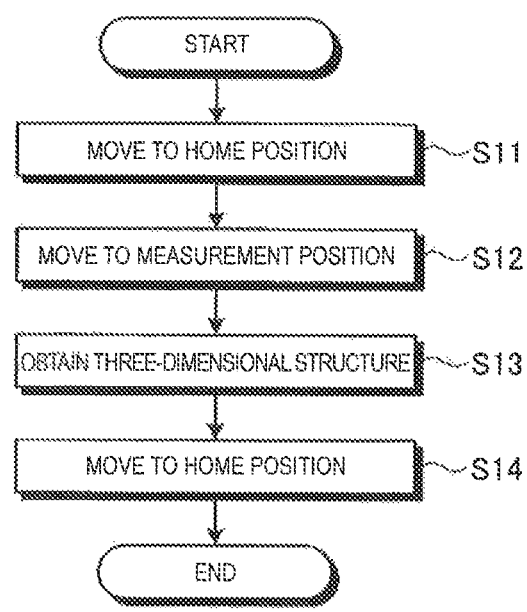
FIG. 34 is a flowchart illustrating an example of a procedure for measuring a shape and the like of a subject using a detection device according to an embodiment.
Figure 35:
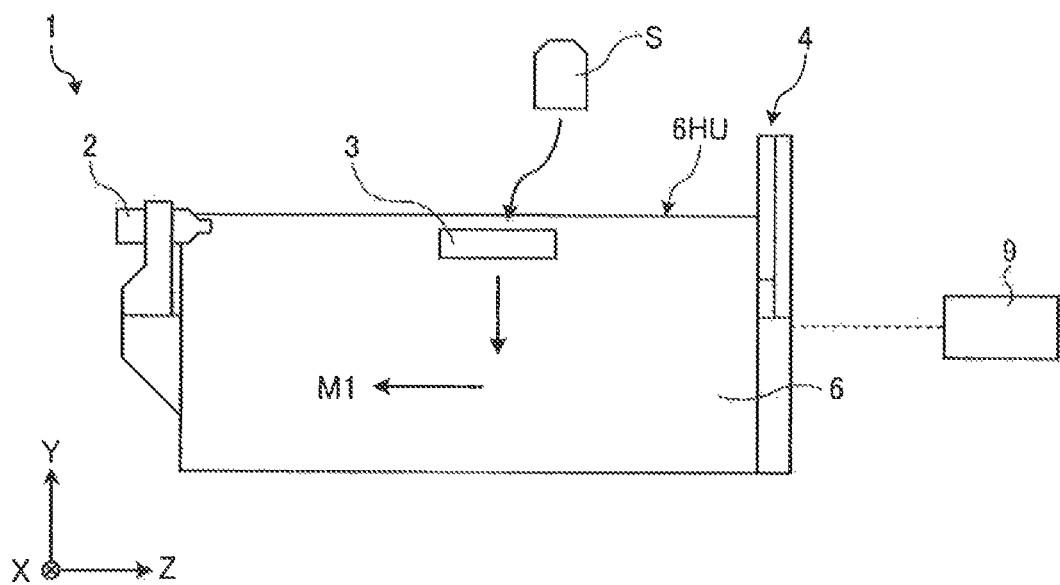
FIG. 35 is a diagram illustrating an example of a procedure for measuring a shape and the like of a subject using a detection device according to an embodiment.
Figure 36:
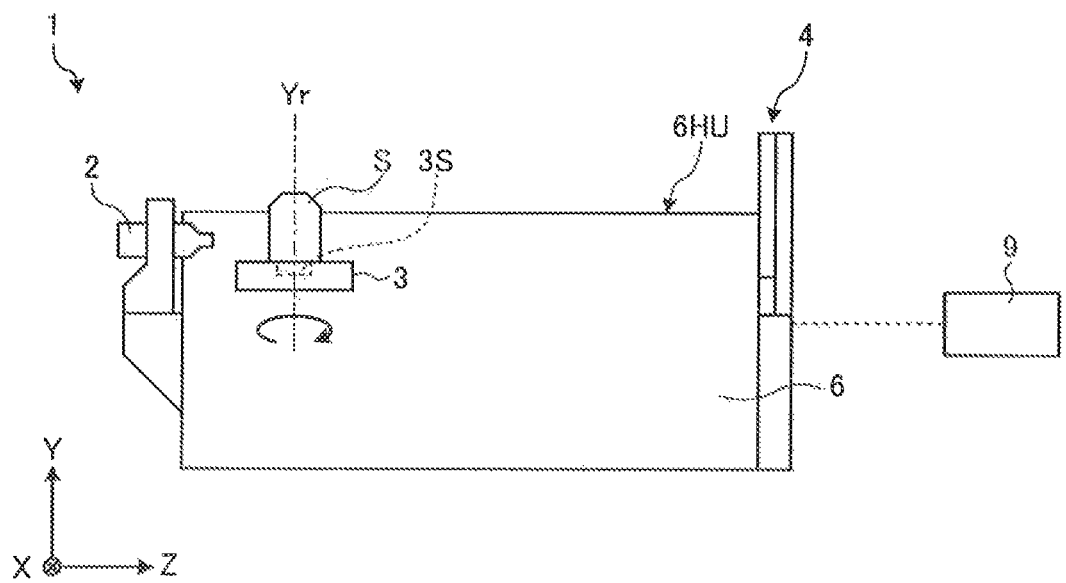
FIG. 36 is a diagram illustrating an example of a procedure for measuring a shape and the like of a subject using a detection device according to an embodiment.
Figure 37:
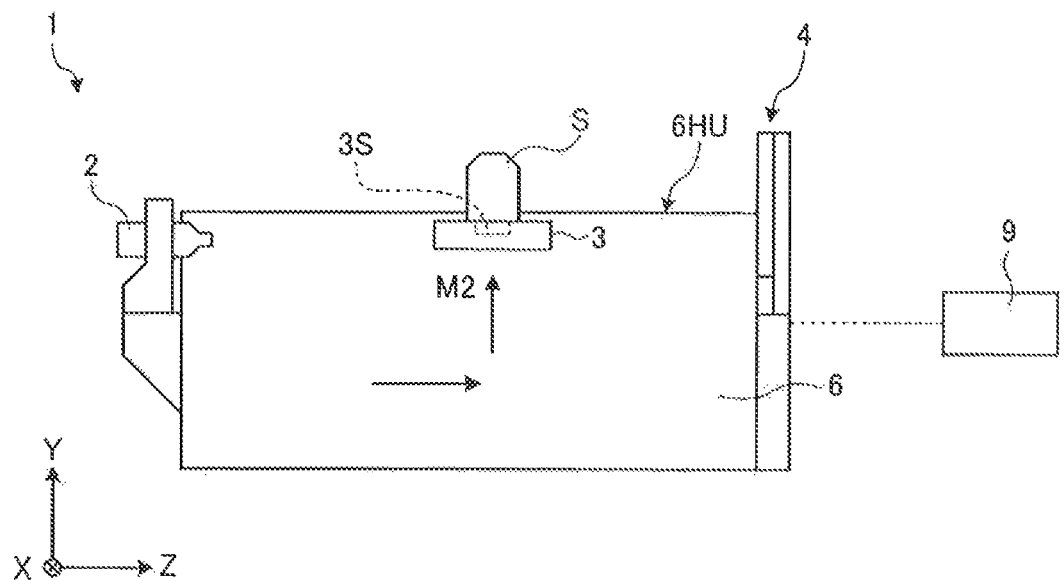
FIG. 37 is a diagram illustrating an example of a procedure for measuring a shape and the like of a subject using a detection device according to an embodiment.

FIG. 34 is a flowchart illustrating an example of a procedure for measuring the shape and the like of the subject using the detection device according to the embodiment. FIGS. 35 to 37 are diagrams illustrating an example of a procedure for measuring the shape and the like of the subject using the detection device according to an embodiment. As illustrated in FIG. 35, after the aforementioned calibration ends, the control device 9 moves the table 3 to a home position in order to measure the shape and the like of the subject S using the detection device 1 (step S11). The home position is between the X-ray source 2 and the detector 4 and in the vicinity of the opening 6HU in the support body 6. In the present embodiment, the table 3 moves to the vicinity of the opening 6HU in the support body 6 when the subject is placed on the table 3, and thus this configuration has an advantage in that it is easier for an operator of the detection device 1 to place the subject S on the table 3.

Once the subject S is placed on the table 3, the support mechanism 3S of the table 3 supports the subject S. Next, the control device 9 moves the subject S to a measurement position by moving the table 3 in at least one of the X-axis direction, the Y-axis direction, and the Z-axis direction (step S12). In the example illustrated in FIG. 35, the control device 9 moves the table 3 toward the X-ray source 2 (the direction indicated by an arrow M1 in FIG. 35). Next, the control device 9 irradiates the subject S that has been moved to the measurement position with the X-rays XL from the X-ray source 2, and detects the transmitted X-rays transmitted through the subject S using the detector 4. At this time, as described earlier, the control device 9 irradiates the subject S with the X-rays while rotating the table 3 that supports the subject S (see FIG. 36). The control device 9 obtains the image of the subject S based on the transmitted X-rays transmitted through the subject S (the X-ray transmission data) at each position (each rotation angle) of the subject S. Next, the control device 9 carries out computations on the basis of the obtained X-ray transmission data (image), reconstructs the tomographic image of the subject S, and obtains the three-dimensional data of the internal structure of the subject S (the three-dimensional structure) (step S13).

Once the three-dimensional data of the internal structure of the subject S has been obtained, the control device 9 moves the table 3 to the home position (step S14). In the present embodiment, the control device 9 moves the table 3 in the direction indicated by an arrow M2 indicated in FIG. 37. Upon the table 3 moving to the home position, the subject S ceases to be supported by the support mechanism 3S. The operator can then remove the subject S from the table 3. As described earlier, the home position is in the vicinity of the opening 6HU in the support body 6, and thus this configuration has an advantage in that it is easier for the operator to remove the subject S from the table 3.

In this manner, in the detection device 1, the subject S is placed on the table 3 and removed from the table 3 from the opening 6HU, or in other words, from between the first side wall 6SA and the second side wall 6SB on the side of the first side wall 6SA and the second side wall 6SB of the support body 6 that is opposite from the base portion 6B, illustrated in FIG. 2. The opening 6HU in the support body 6 is a space surrounded by an end portion of the first side wall 6SA, an end portion of the second side wall 6SB, and end portion of the third side wall 6SC, and an end portion of the fourth side wall 6SD, and thus has a large surface area. Accordingly, passing through the opening 6HU makes it easier to place the subject S on the table 3 and remove the subject S from the table 3.

Figure 38:
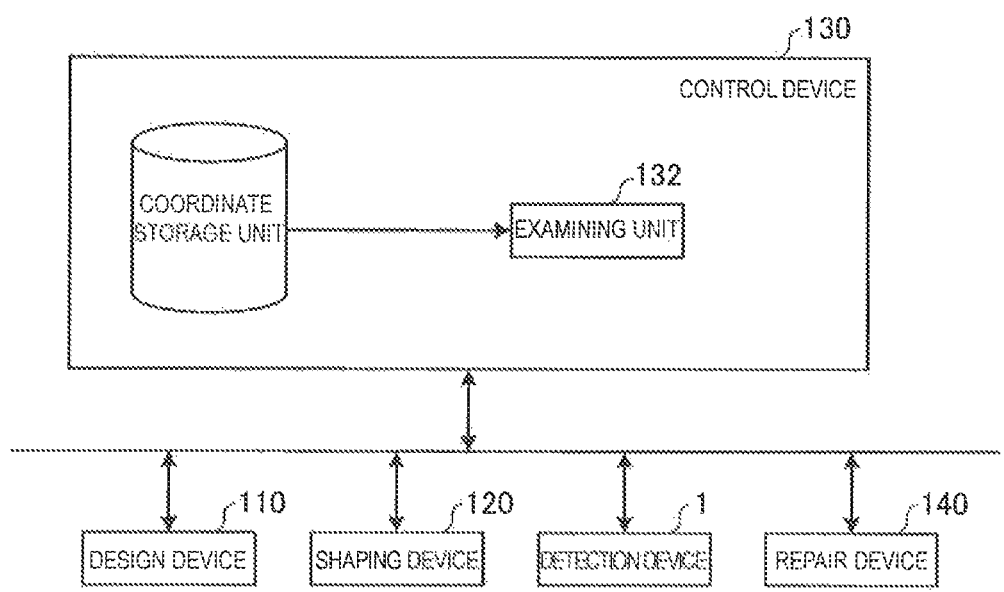
FIG. 38 is a diagram illustrating an example of a structure manufacturing system including a detection device according to an embodiment.
Figure 39:
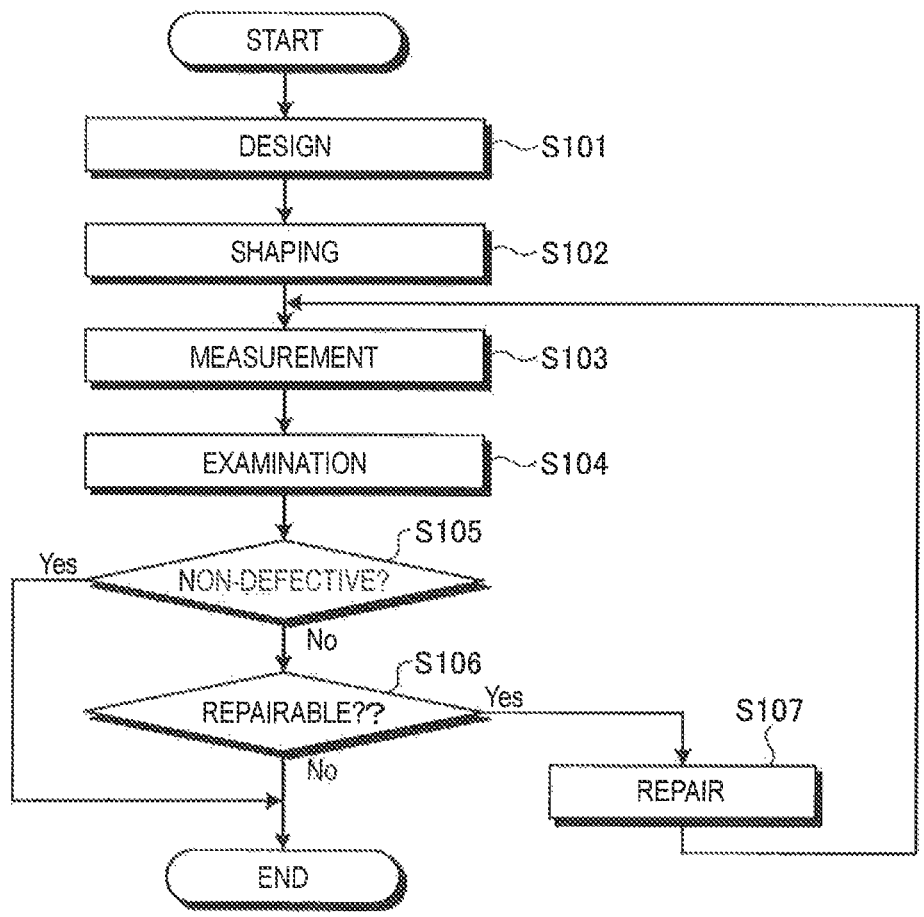
FIG. 39 is a flowchart illustrating the flow of processing performed by the structure manufacturing system.

FIG. 38 is a diagram illustrating an example of a structure manufacturing system including the detection device according to the embodiment. FIG. 39 is a flowchart illustrating the flow of processing performed by the structure manufacturing system. First, a design device 110 creates design information regarding the shape of a structure (step S101). Next, a shaping device 120 creates the aforementioned structure on the basis of the design information (step S102). Next, the detection device 1 measures coordinates regarding the shape of the structure (step S103). Next, an examining unit 132 of a control device 130 examines whether or not the structure has been created according to the design information by comparing shape information of the structure created by the detection device 1 with the aforementioned design information (step S104).

Next, the examining unit 132 of the control device 130 determines whether or not the created structure is non-defective (step S105). In the case where the created structure is non-defective (step S105, YES), the structure manufacturing system 200 ends the processing. In the case where the created structure is defective (step S105, NO), the examining unit 132 of the control device 130 determines whether or not the created structure can be repaired (step S105). In the case where the created structure can be repaired (step S106, YES), a repair device 140 reprocesses the structure (step S107) and returns to the process of step S103. In the case where the created structure cannot be repaired (step S106, NO), the structure manufacturing system 200 ends the processing. The processing of this flowchart ends thus.

The detection device 1 according to the embodiment can accurately measure the coordinates of the structure, and thus the structure manufacturing system 200 can determines whether or not the created structure is non-defective. Furthermore, the structure manufacturing system 200 can reprocess and repair the structure in the case where the structure is defective.

Although the detection device 1 includes the X-ray source in the aforementioned embodiments, the X-ray source may be a device that is outside of the detection device 1. To rephrase, the X-ray source need not constitute at least part of the detection device. In the aforementioned embodiments, the subject S is not limited to an industrial component, and may be a person instead, for example. Furthermore, in the aforementioned embodiments, the detection device 1 may be used for medical purposes. Although in the aforementioned embodiment, the X-ray source and the detection device are fixed at predetermined locations, the table is rotated, and the image of the subject S is obtained, the scanning method is not limited thereto. One of the X-ray source and the detection device may be fixed in a predetermined position, and the other may be mobile. Alternatively, both the X-ray source and the detection device may be mobile.

Figure 40:
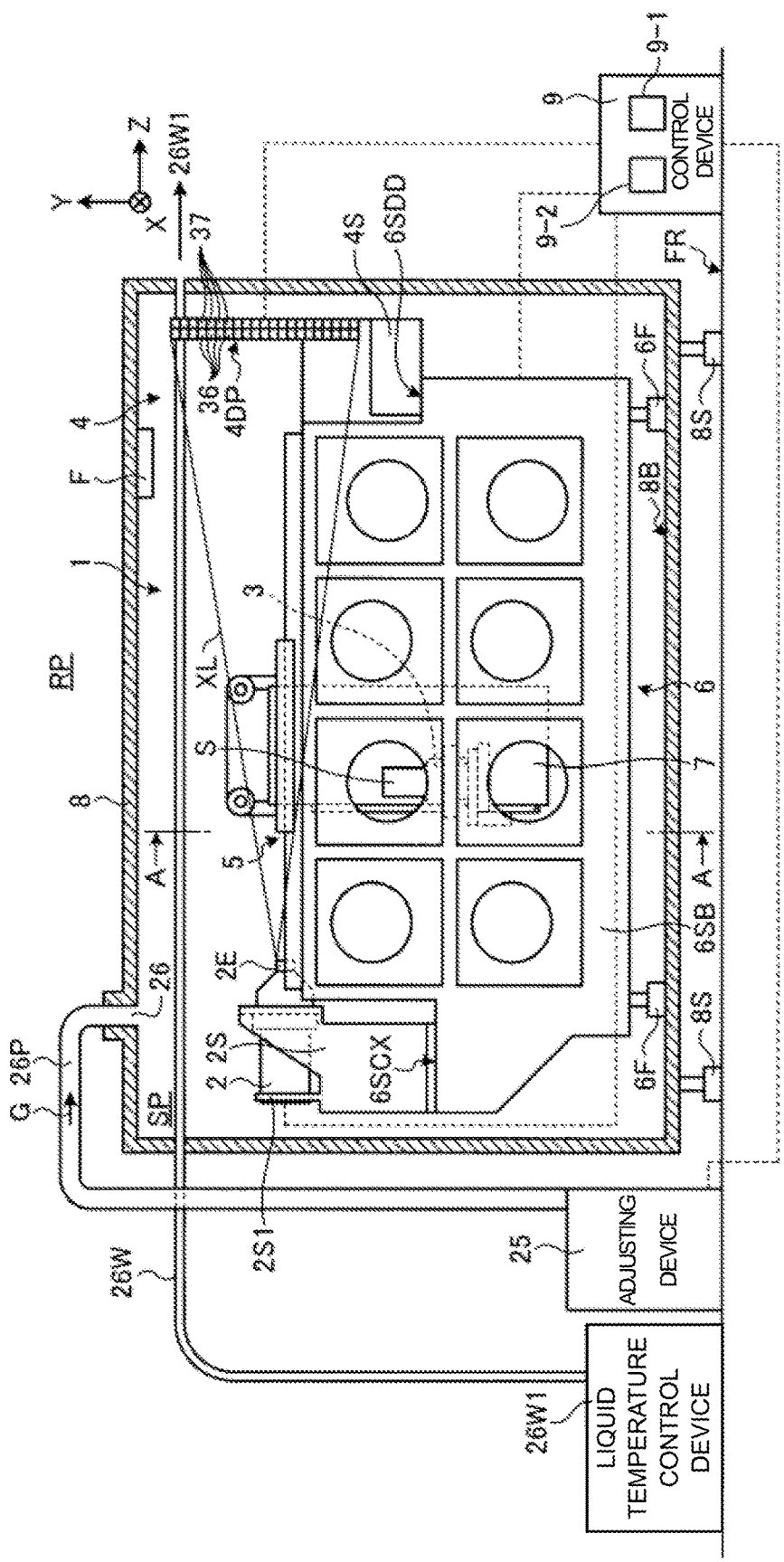
FIG. 40 is a diagram illustrating a detection device according to a variation on an embodiment.

FIG. 40 is a diagram illustrating a detection device according to a variation on the embodiment. In addition to the aforementioned respective embodiments, a method of holding the X-ray source may be a holding method such as that according to the variation illustrated in FIG. 40. Although the method of holding the X-ray source 2 in the embodiment involves holding the X-ray source 2 using the X-ray source support member 2S, an X-ray support member 2S1 may be added as well. The X-ray source 2 is supported in the vicinity of the emitting portion 2E of the X-ray source 2 and the other end of the X-ray source 2 relative to the X-ray emitting portion 2E. According to this configuration, the position of the emitting portion 2E can be suppressed from deviating from a predetermined position in the Y-axis direction illustrated in FIG. 40, for example. In addition, a member that supports the X-ray source 2 and a guide mechanism (not illustrated) may be employed as the X-ray source support member 2S1. In this case, even if, for example, the X-ray source 2 has thermally deformed due to the X-ray irradiation and the X-ray source 2 has expanded or contracted in the Z-axis direction while the X-ray support member is in a fixed state, the position at which the member that supports the X-ray source 2 is fixed can change in the Z-axis direction along the guide mechanism (not illustrated), as compared to the case where the member that supports the X-ray source 2 is fixed. Accordingly, the X-ray source 2 can be suppressed from deforming. Furthermore, a change in the direction in which the X-rays are emitted, caused by the X-ray source 2 deforming, can be suppressed.

In addition to the aforementioned respective embodiments, a method of holding the detector 4 may be a holding method such as that according to the variation illustrated in FIG. 40. Although the detector support member 4S supports the detector 4 from the rear side of the detection surface that detects the X-rays in the embodiments, a side surface of the detector may be supported by the detector support member 4S as well, as illustrated in FIG. 40. In the present embodiment, the support member 4S is provided in the same position as the first side wall 6SA in the X-axis direction. Meanwhile, in the present variation, the support member 4S is provided in the same position as the second side wall 6SB in the X-axis direction. In the present variation, the support member 4S is created from the same member as the first side wall 6SA. Meanwhile, the support member 4S may be created as an integrated part of the first side wall 6SA. According to the present variation, it is not necessary to dispose the support member 4S on the rear surface of the detector 4, or in other words, on the opposite surface from the incidence surface 4DP, and thus it is not necessary to expand the chamber member 8 in the Z-axis direction, for example.

In addition to the configurations in the aforementioned embodiments, a temperature-controlled liquid may be used in order to adjust the temperature of the internal space SP of the chamber member 8. For example, as illustrated in FIG. 40, a liquid temperature control device 26W1 introduces a liquid adjusted to a predetermined temperature into a liquid temperature control channel 26W. The liquid temperature control channel 26W is disposed in the internal space SP of the chamber member 8. The liquid temperature control channel 26W is manufactured from stainless steel, for example. By filling the interior of the liquid temperature control channel 26W with a temperature-controlled liquid (water, for example), surfaces of the liquid temperature control channel 26W in contact with the internal space SP can be set to a temperature close to that of the temperature-controlled liquid. The temperature of air within the internal space SP can be adjusted as a result of the air within the internal space SP coming into contact with those surfaces.

In this case, it is desirable for the air within the internal space SP and the liquid temperature control channel 26W to come into contact over a broad area. In the present variation, a channel having a circular cross-section is used for the liquid temperature control channel 26W, and the entire outer side of the cross-section can make contact with the air in the internal space SP. Note that the temperature of the air within the internal space SP can be adjusted to the predetermined temperature as long as at least part of the cross-section of the liquid temperature control channel 26W makes contact with the air in the internal space SP. Although there is one liquid temperature control channel 26W in the present variation, a plurality of liquid temperature control channels 26W may be provided. In the case where a plurality of such channels are provided, the liquids introduced into the respective channels may have different temperatures. In addition, a temperature sensor (not illustrated) may be provided in the internal space SP of the chamber member 8, near the X-ray source 2, for example, and the liquid temperature control device 26W1 may adjust the temperature of the liquid introduced into the liquid temperature control channel 26W on the basis of the temperature of the internal space SP of the chamber member 8 as outputted from the temperature sensor.

In the present variation, the liquid introduced into the temperature control channel 26W from the liquid temperature control device 26W1 traverses the interior of the temperature control channel 26W disposed in the external space RP, traverses the interior of the temperature control channel 26W disposed in the internal space SP, traverses the external space RP once again, and then reaches the temperature control channel 26W. After reaching the temperature control channel 26W, the liquid is adjusted to a predetermined temperature within the liquid temperature control device 26W1, and is then introduced again into the temperature control channel 26W. Although the liquid temperature control device 26W1 is disposed in the external space RP in the present variation, the liquid temperature control device 26W1 may be disposed in the internal space SP instead. In addition, although the liquid temperature control device 26W1 adjusts the temperature of the internal space SP, the same temperature control channel 26W may additionally adjust the temperature of the internal space SP having passed along the X-ray source 2, for example.

The various constituent elements in the aforementioned embodiments can be combined as desired. There are also some cases where some constituent elements are not used. The disclosures in all publications and US patents regarding the detection device and the like as cited in the foregoing embodiments and variations are hereby incorporated into this document by reference to the fullest extent allowed by law. Other embodiments, application techniques, and the like made by one skilled in the art on the basis of the foregoing embodiments are all considered to fall within the scope of the stated embodiments.

What is claimed is:

1. An X-ray device configured to irradiate a measurement object with X-rays and detect X-rays transmitted through the measurement object, the X-ray device comprising:
    an X-ray source configured to emit X-rays from a light-emission point;
    a table configured to support the measurement object;
    a detector configured to detect at least a portion of transmitted X-rays that have been emitted from the X-ray source and transmitted through the measurement object;
    a mover configured to move one of the X-ray source, the table, or the detector in a first direction as a mobile object in order to change at least one of a distance between the light-emission point and the measurement object or a distance between the light-emission point and the detector; and
    a first position detector and a second position detector, each configured to measure a position of the mobile object in the first direction,
    the first position detector and the second position detector being disposed along a second direction orthogonal to the first direction in a mobile region of the mover.

2. The X-ray device according to claim 1, wherein the first position detector and the second position detector are disposed so that an optical axis of the X-ray source is located between the first position detector and the second position detector.

3. The X-ray device according to claim 2, further comprising a first scale and a second scale, each having a pattern arranged in the first direction and being disposed in a fixed manner,
    wherein the first position detector is configured to measure a position of the mobile object in the first direction by detecting the pattern of the first scale and the second position detector is configured to measure the position of the mobile object in the first direction by detecting the pattern of the second scale.

4. The X-ray device according to claim 3, further comprising a guide plane configured to guide a movement of the mover in the first direction,
    wherein the table comprises a support surface that supports the measurement object, and
    wherein a measurement position in the first scale by the first position detector and a measurement position in the second scale by the second position detector are the same as the guide plane in a direction orthogonal to the support surface.

5. The X-ray device according to claim 4, wherein the guide plane further includes a first guide plane and a second guide plane; and
    the first guide plane and the second guide plane are disposed so that the optical axis of the X-ray source is located between the first guide plane and the second guide plane.

6. The X-ray device according to claim 1, wherein the first position detector and the second position detector are supported by the mover.

7. The X-ray device according to claim 1, wherein the first position detector and the second position detector are disposed outside of a region surrounded by a plane formed by connecting the light-emission point of the X-ray source to an outer edge of a light-receiving surface at which the detector receives the X-rays, and the light-receiving surface.

8. The X-ray device according to claim 1, comprising a control device that computes a shape of the measurement object from a result of the detector detecting the transmitted X-rays transmitted through the measurement object upon the measurement object held on the table being irradiated with X-rays by the X-ray source.

* * * * *